United States Patent [19]

Hartwell et al.

[11] Patent Number: 5,674,996
[45] Date of Patent: Oct. 7, 1997

[54] CELL CYCLE CHECKPOINT GENES

[75] Inventors: Leland H. Hartwell, Seattle, Wash.; Ted A. Weinert, Tucson, Ariz.; Sharon E. Plon, Houston, Tex.; Mark T. Groudine, Seattle, Wash.

[73] Assignees: University of Washington, Seattle, Wash.; Arizona Board of Regents on behalf of the University of Arizona, Tucson, Ariz.; Fred Hutchinson Cancer Research Center, Seattle, Wash.

[21] Appl. No.: 198,446

[22] Filed: Feb. 18, 1994

Related U.S. Application Data

[63] Continuation-in-part of PCT/US93/04458, May 12, 1993, which is a continuation-in-part of Ser. No. 884,426, May 14, 1992, abandoned, which is a continuation-in-part of Ser. No. 882,051, May 12, 1992, abandoned.

[51] Int. Cl.$^6$ ................................................. C07H 21/04
[52] U.S. Cl. ................................. 536/24.31; 536/23.5
[58] Field of Search ........................... 435/6; 536/24.5, 536/23.5, 23.51, 23.74, 24.31

[56] References Cited

PUBLICATIONS

Weinert, T.A. and L.H. Hartwell, "Cell Cycle Arrest of cdc Mutants and Specificity of the RAD9 Checkpoint," *Genetics* 134:63–80 (1993).

Millar, J.B.A. and Russell, P., "The cdc25 M–Phase Inducer: An Unconventional Protein Phosphatase," *Cell* 68:407–410 (1992).

Hunter, T. and Pines, J., "Cyclins and Cancer," *Cell* 66:1071–1074 (1991).

Koff, A. et al., "Human Cyclin E, a New Cyclin That Interacts with Two Members of the CDC2 Gene Family," *Cell* 66:1–12 (1991).

Haas, A.L. et al., "Ubiquitin Conjugation by the Yeast RAD6 and CDC34 Gene Products: Comparison to Their Putative Rabbit Homologs, E2$_{20K}$ and E2$_{32K}$," *The Journal of Biological Chemistry* 266(8):5104–5112 (1991).

Hunt, T., "Destruction's Our Delight," *Nature* 349:100–101 (1991).

Glotzer, M. et al., "Cyclin is Degraded by the Ubiquitin Pathway," *Nature* 349:132–138 (1991).

Lew, et al., *Cell* 66:1197–1206 (1991).

Igarashi, et al., *Nature* 353:80–83 (1991).

Weinert, T.A. and Hartwell, L.H., "Characterization of RAD9 of *Saccharomyces cerevisiae* and Evidence that its Function Acts Posttranslationally in Cell Cycle Arrest after DNA Damage," *Molecular and Cellular Biology* 10(12):6554–6564 (1990).

Lock, R.B. and Ross, W.E., "Inhibition of p34$^{cdc2}$ Kinase Activity by Etoposide or Irradiation as a Mechanism of G$_2$ Arrest in Chinese Hamster Ovary Cells[1]," *ExpH. and Cell Res.* 50:3761–3766 (1990).

Seufert, W. and Jentsch, S., "Ubiquitin–conjugating enzymes UBC4 and UBC5 mediate selective degradation of short–lived and abnormal proteins," *The EMBO Journal* 9(2):543–550 (1990).

Lock, et al., *Canc. Res.* 50:3767–3771 (1990).

Hartwell, L.H. and Weinert, T.A., "Checkpoints: Controls That Ensure the Order of Cell Cycle Events," *Science* 246:629–633 (1989).

Schiestl, R.H. et al., "Cloning and Sequence Analysis of the *Saccharomyces cerevisiae* RAD9 Gene and Further Evidence that Its Product Is Required for Cell Cycle Arrest Induced by DNA Damage," *Molecular and Cellular Biology* 9:1882–1896 (1989).

Goebl, M.G., et al., "The Yeast Cell Cycle Gene CDC34 Encodes a Ubiquitin–Conjugating Enzyme," *Science* 241:1331–1335 (1988).

Weinert, T.A. and Hartwell, L.H., "The RAD9 Gene Controls the Cell Cycle Response to DNA Damage in *Saccharomyces cerevisiae*," *Science* 241:317–322 (1988).

Lee, M.G. and Nurse, P., "Complementation used to clone a human homologue of the fission yeast cell cycle control gene cdc2," *Nature* 327:31–35 (1987).

Pringle, J.R. and Hartwell, L.H., "The *Saccharomyces cerevisiae* cell cycle," In: *The Molecular Biology of the Yeast Saccharomyces: Life cycle and Inheritance* (ed. J.N. Strathen et at.), Cold Spring Harbor Laboratory, Cold Spring Harbor, New York, p. 97 (1981).

Hartwell, L.H., "Three Additional Genes Required for Deoxyribonucleic Acid Synthesis in *Saccharomyces cerevisiae*," *Journal of Bacteriology* 115(3):966–974 (1973).

(List continued on next page.)

*Primary Examiner*—Scott W. Houtteman
*Attorney, Agent, or Firm*—Christensen O'Connor Johnson & Kindness PLLC

[57] ABSTRACT

Human checkpoint huCDC34, huRAD9$_{compA}$, and huRAD9$_{compB}$ cDNAs shown in SEQ ID Nos:7–9. A method for isolating a human checkpoint cDNA that is capable of restoring growth at a restrictive temperature in a yeast test cell, wherein the yeast test cell comprises a genome having a first gene that forms a DNA strand break at a restrictive temperature and a second gene that fails to induce a cell cycle arrest in response to the DNA strand break, whereby the growth of the yeast test cell is inhibited at the restrictive temperature, the method comprising the steps of: obtaining a human cDNA library comprising a plurality of human cDNA clones; inserting the human cDNA clones individually into plasmid vectors comprising a selectable marker gene; transforming a culture of the yeast test cells with the plasmid vectors from the preceding step; selecting for yeast test cells transformed with the selectable marker gene; growing the selected transformants at the restrictive temperature and isolating a candidate transformant capable of growing at the restrictive temperature; and identifying the human cDNA carried by the candidate transformant as a human checkpoint cDNA by sequencing the human cDNA carried by the candidate transformant and determining that the human cDNA is less than 50% homologous with both the first gene and the second gene. Also yeast checkpoint RAD17, RAD24, MEC1, MEC2, and MEC3 cDNAs shown in SEQ ID Nos:10–19.

1 Claim, No Drawings

PUBLICATIONS

Zheng, P. et al., "SPK1 Is an Essential S–Phase-Specific Gene of *Saccharomyces cerevisiae* That Encodes a Nuclear Serine/Threonine/Tyrosine Kinase," *Molecular and Cellular Biology* 13(9):5829–5842 (1993).

Weinert, T.A. et al., "Mitotic checkpoint genes in budding yeast and the dependence of mitosis on DNA replication and repair," In: *Genes & Development*, Cold Spring Harbor Laboratory, Cold Spring Harbor, New York, pp. 1–14 (1994).

Stern, D.F. et al., "Spk1, a New Kinase from *Saccharomyces cerevisiae*, Phosphorylates Proteins on Serine, Threonine, and Tyrosine," *Molecular and Cellular Biology* 11(2):987–1001 (1991).

Hennessy, K.M. et al., "Subcellular localization of yeast CDC46 varies with the cell cycle," *Genes & Development*, Cold Spring Harbor Laboratory, Cold Spring Harbor, New York, pp. 2252–2263 (1990).

Plon, S.E. and Groudine, M., "Defining the human cell checkpoint system," 42nd Annual Meeting of The American Society of Human Genetics, San Francisco, California, Nov. 9–13, 1992. *The American J. of Human Genetics* 51(4) Abstract No. 259 (1992).

Plon, S.E. et al., "Complementation of yeast cell–cycle checkpoint mutations by human cDNAs," Abstracts of papers presented at the 1992 Meeting on *The Cell Cycle*, May 13–17, 1992, Cold Spring Harbor Laboratory, Cold Spring Harbor, New York, p. 153 (1992).

Plon, S.E. et al., "Cloning of the human CDC34 cell cycle gene and a putative human G2 checkpoint gene by complementation in yeast," 43rd Annual Meeting of The American Society of Human Genetics, New Orleans, Louisiana, Oct. 5–9, 1993. *The American J. of Human Genetics* 53(3) Abstract No. 30 (1993).

Plon, S.E. et al., "Isolation of human cell cycle genes: CDC34 and a potential G2 checkpoint gene, CCC1," Abstracts of papers presented at the 1994 Meeting on *The Cell Cycle*, May 18–22, 1994, Cold Spring Harbor Laboratory, Cold Spring Harbor, New York, p. 221 (1994).

CELL CYCLE CHECKPOINT GENES

This application is a continuation-in-part of International Application No. PCT/US93/04458, filed May 12, 1993, which is a continuation-in-pa of Ser. No. 07/884,426, filed May 14, 1992, now abandoned, which is a continuation-in-part of Ser. No. 07/882,051, filed May 12, 1992 now abandoned.

This invention was made with government support under grant GM17709 awarded by the National Institutes of Health and grant CA57156 awarded by the Nation Cancer Institute. The government has certain rights in the invention.

FIELD OF THE INVENTION

The invention relates generally to molecular biology, genetic engineering, and recombinant techniques, and specifically to checkpoint genes and proteins and surveillance mechanisms for controlling timing of the cell cycle prior to mitosis so that DNA damage by radiation, chemicals, or drugs can be repaired.

BACKGROUND OF THE INVENTION

Cellular resistance to DNA damage and replication errors is critical to survival of cells, tissues, and organisms. Radiation induces DNA strand breaks. Failure to repair even one DNA strand break can be lethal in yeasts. Cellular resistance to DNA damage consists of separate processes for recognition of damage and repair. Control mechanisms exist for arresting the cell division cycle (cdc) until DNA repair is completed. Delay can occur in different phases of the cell cycle depending on the type of DNA damage and the stage in the cell cycle at which the damage occurs. In particular, damage resulting from DNA strand breaks caused by ionizing radiation or topoisomerase inhibitors causes delay of the cell cycle in the G2 phase before entry into mitosis. The delay may be observed as a decline in the mitotic index of human or yeast cells approximately one hour post irradiation.

Several classes of mutations in yeasts have been defined that result in deregulation of the cell cycle. Temperature-sensitive (ts) mutations in yeast cdc genes can result in death at defined points in the cell cycle when strains are shifted to the non-permissive temperature, and lethality may increase in a temperature-sensitive manner (1). More than thirty-two different cdc genes have been identified in *S. cerevisiae* (2). One such mutant, cdc9-8$^{ts}$, is a DNA ligase mutant in which the temperature-dependent increase in lethality presumably occurs because of a general failure in ligating chromosomal DNA Okazaki fragments following chromosomal DNA replication. The molecular activities of most cdc genes is largely unknown.

Recently a new class of cell cycle regulatory mutations has been identified and labeled checkpoint mutations (3). Checkpoints exist to ensure that DNA synthesis is completed before mitosis begins; that anaphase is delayed until all the chromosomes arrive on the metaphase plate; that centrosome duplication does not occur until DNA has been synthesized; and, that initiation of DNA synthesis is coordinated between different regions in a chromosome. In yeast, RAD9 is one such checkpoint gene of *S. cerevisiae* that mediates G2 delay after DNA damage. rad9 mutants have greatly increased radiation sensitivity (less than 0.1% survival at 8000 rads for rad9 yeasts vs. 30% for RAD+ yeasts) (4). Direct visualization of budding yeasts after irradiation shows that rad9 cells continue into mitosis despite potentially lethal DNA damage and die in subsequent generations. RAD9 protein is not required for DNA repair, and RAD9 is not an essential gene in the cell cycle. In the absence of DNA damage, rad9 cells display normal cell cycle kinetics but accumulate spontaneous chromosome loss at a higher rate than wild-type strains. Northern blot analyses of RNA from yeast in different parts of the cell cycle and from pre- and post-irradiated cells show a constant level of RAD9 mRNA. The yeast RAD9 gene has been cloned, and the translated open reading frame encodes 1309 amino acids that exhibit no significant homology to any other known proteins in the database (4). No human genes have been identified that mediate the G2 delay induced by DNA damage.

The simultaneous presence of both a rad9 checkpoint mutation and a cdc9-8 mutation (i.e., in a double mutant strain) substantially increases the rate of cell death when cells are shifted to the nonpermissive temperature (4). This increase in lethality is presumably due to DNA strand breaks resulting from incomplete DNA synthesis (cdc9-8) and failure to properly delay the cycle to repair the damage (rad9).

CDC34 (not to be confused with p34$^{cdc2}$) is an essential gene in yeast required for the transition from late G1 to the initiation of DNA synthesis (5). Sequence analysis and enzymatic assays support the notion that CDC34 is an E2 ubiquitin ligase. The target protein ubiquitinated by CDC34 is unknown.

While it has been possible to study checkpoint genes in yeast, few of their human counterparts have been identified and it is not presently known whether events observed in yeast will be generally applicable to cell cycles of higher eukaryotes.

SUMMARY OF THE INVENTION

A genetic protocol is disclosed to identify human checkpoint cDNAs based on increased lethality of yeast mutants having a temperature-sensitive mutation that produces damaged DNA and a checkpoint gene mutation that hinders DNA repair. The strategy utilizes the cdc9-8 yeast strain with a DNA ligase mutation (temperature sensitive for DNA damage), and the mec1 or rad9 checkpoint mutations (impaired in G2 arrest and thereby in DNA repair).

The subject screening assay uses the double mutants mec–1, cdc9-8 (ATCC No. 74155) and rad9,cdc9-8 (ATCC No. 74154 ) as yeast test cells to select and isolate human checkpoint cDNA clones that are capable of complementing or suppressing a defective yeast G2 checkpoint function. Feasibility of the assay was established in experiments that identified three novel human genes involved in human cell cycle control: huCDC34, huRAD9$_{compA}$, and huRAD9$_{compB}$.

The huCDC34 cDNA clone (clone #1; alias 171tx61) was identified as suppressing the mec–1 checkpoint mutation that renders mec1,cdc9 cells temperature sensitive for growth at 30° C. Clone #1 did not suppress the checkpoint defect in rad9,cdc9-8. The nucleotide sequence of the antisense strand of clone #1 is shown in SEQ ID NO:7 analysis revealed a surprising homology between the isolated human cDNA and the previously cloned CDC34 gene of *S. cerevisiae*. (Yeast CDC34 is a member of the E2 ubiquitin ligase family and has no significant homology with MEC1.) Human clone #1 cDNA complemented a cdc34$^{ts}$ yeast mutation, confirming its identity as a human homolog of yeast CDC34. The huCDC34 gene is expressed in multiple cell lines, and Southern blot analysis reveals evidence for a single gene that is highly conserved in higher eukaryotes. The huCDC34 gene was mapped to a telomeric region of chromosome 19p13.3, and the mouse CDC34 gene mapped to chromosome 11. The position of the huCDC34 gene in the genome has not been preserved during evolution, designating a novel region of synteny in chromosome 19.

The huRAD9$_{compA}$ cDNA clone (clone #2; alias 83tx42) was identified as suppressing the rad9 checkpoint mutation that renders rad9,cdc9 cells temperature sensitive for growth at 30° C. Clone #2 suppressed the checkpoint defect in rad9,cdc9-8 as well as mec1,cdc9-8 cells, but failed to complement the defect in the cdc9-8 cells. The nucleotide sequence of clone #2 is shown in SEQ ID NO:8. The long open reading frame (ORF) in clone #2 had no significant homology to any previously described protein. The phenotype of huRAD9$_{compA}$ appears to be a slowing of the cell cycle during S phase to allow more time for DNA repair.

The huRAD9$_{compB}$ cDNA clone (clone #3; alias 171tx23) was identified as suppressing the mec–1 checkpoint mutation that renders mec–1,cdc9 cells temperature sensitive for growth at 30° C. Clone #3 suppressed the checkpoint defect in rad9,cdc9-8 or mec1,cdc9-8 cells, but not in cdc9-8 cells. Clone #3 was capable of conferring radiation resistance upon a single mutant mec1 or rad9 cell. The nucleotide sequence of clone #3 is shown in SEQ ID NO:9. The ORF in clone #3 had no significant homology to any previously described protein. The phenotype of clone #3 suggests that it may act in a G2 arrest pathway that is either downstream of, or independent from, both RAD9 and MEC 1.

These results demonstrate the success of the subject protocol for selecting and isolating novel human cDNAs that are active in regulating the human cell division cycle.

SEQ IDS:7–9 depict the disclosed huCDC34, huRAD9$_{compA}$, and huRAD9$_{compB}$ cDNAS, respectively.

SEQ IDS:10, 12, 14, 16, and 18 depict the disclosed RAD17, RAD24, MEC1, MEC2, and MEC3 cDNAs, respectively.

DETAILED DESCRIPTION OF THE PREFERRED EMBODIMENT

Methods are disclosed for selecting and isolating human cDNAs responsible for radiation sensitivity and resistance. The methods are based on selecting human cDNAs that complement or suppress checkpoint mutations in yeast cells. The strategy involves using yeast double mutants that are: 1) conditional for DNA damage (e.g., as the result of a DNA ligase mutation); and, 2) mutant for a cell cycle checkpoint function that is necessary to repair damaged DNA (e.g., a G2 checkpoint where arrest allows DNA repair).

Prior to conducting the experiments described below, it was not known whether human checkpoint genes could exert their actions in yeast. While certain other cdc genes had been shown to be capable of crossing over between yeast and man, it was reasoned that critical checkpoint functions could be species specific and highly evolved to fit the functions of a yeast or human cell. Expression of a human checkpoint cDNA in a double mutant yeast cell might either go unnoticed, because the human protein could be incapable of rescuing the double lethal mutation, or it might even prove lethal when in a yeast background. Considering the improbable nature of any effect, a screen assay was developed for screening hundreds of thousands of transformants. Remarkably, in the first series of experiments, a single active clone (clone#1) was identified out of a total of 200,000 transformants. Sequence analysis revealed significant homology of the human cDNA to the CDC34 gene of S. cerevisiae. Clone #1 human cDNA efficiently complements a yeast cdc34 mutation, identifying it as a human homolog of yeast CDC34. The result of this assay was particularly unexpected since all previous reports linked the function of yeast CDC34 to events in the late G1 phase of the cell cycle prior to entry into S phase. Interestingly, the limited sequence homology between yeast and man was not sufficient for yeast cDNA to identify human CDC34. (S. Plon, unpublished.)

As used herein, "checkpoint" is intended to mean a timepoint in the cell cycle of a eukaryotic cell at which progression to mitosis may be arrested if the cell contains chromosomal DNA with one or more strand breaks. Illustrative methods by which DNA strand breaks may be introduced into chromosomal DNA include DNA ligase mutations, topoisomerase mutations, X-irradiation, gamma-irradiation, and treatment with drugs (e.g., hydroxyurea), or treatment with chemotherapeutic agents, e.g., 5-fluorouracil, ectopside, and the like.

"Checkpoint gene" is intended to mean a gene whose expression (i.e., as RNA or protein) is capable of arresting a cell cycle at a checkpoint in a eukaryotic cell having chromosomal DNA with one or more strand breaks, but not in a eukaryotic cell having native chromosomal DNA, i.e., without DNA strand breaks. The checkpoint gene is capable of conferring upon a eukaryotic cell increased capacity to protect against potentially lethal damage, meaning that the subject eukaryotic cell has an increased capacity for arresting cell mitosis when chromosomal DNA is damaged, e.g., by drugs or radiation. Illustrative examples of eukaryotic checkpoint genes include RAD-9, MEC–1, RAD17, RAD24, MEC–2, and MEC–3. The mec1, mec2, and mec3 genes were identified in S. cerevisiae as mutations that are also deficient for G2 arrest after DNA strand breaks. See Example 4 and SEQ IDS:10–19.

By convention, and as followed herein, terms in capitalized italics refer to the wild-type gene; lowercase italics refer to mutants of the gene; and capitalized nonitalics refer to proteins encoded by the wild-type gene.

"Complementation" is used herein as a genetic term intended to mean that the subject genetic element is homologous to a mutant genetic element such that when introduced into a cell it rescues the cell from the effects of the mutation. For example, MEC–1 DNA rescues the rescues the mec–1 defect in a mec–1,cdc9-8 cell (and RAD9 rescues the rad9 defect in a rad9,cdc9-8 cell) through a process herein referred to as complementation, and the MEC–1 (or RAD9) DNA so capable is referred to as a "complementing cDNA." Similarly, huCDC34 is homologous with yeast CDC34 and able to complement the mutation in single (or double mutant) cells, e.g., single mutant cells of yeast strain cdc34.

"Suppression," "suppress," "suppressing," and "suppressed" are used herein as genetic terms intended to mean rescue of a mutant phenotype by a non-homologous genetic element that circumvents the effects of mutation. For example, human CDC34 is not homologous with mec–1, (i.e., no significant homology detectable by computer-assisted alignment and sequence comparison), and yet huCDC34 is capable of rescuing the mec–1 defect in a mec–1,cdc9-8 cell. Similarly, human RAD9$_{compA}$ is not homologous with RAD9 and yet it is capable of rescuing the rad9 defect in a rad9,cdc9-8 cell by suppressing the mutant checkpoint rad9 function.

"G2 arrest" is intended to mean arrest in the interval of the cell cycle following DNA replication and before mitosis. Illustrative examples of ways in which a cell cycle may be arrested in G2 include X-irradiation, gamma-irradiation, ectopside, and other physical and chemical agents.

A highly sensitive and selective yeast temperature-sensitive selection assay system has now been developed for identifying and isolating mammalian checkpoint genes operative in compensating for a defective G2 checkpoint function. The checkpoint genes so identified are operative in G1 arrest and/or G2 arrest. Using this assay human cDNA clones have been identified and isolated that encode human checkpoint proteins that are functionally active in correcting defects resulting from mutations in yeast checkpoint genes. Three representative human checkpoint cDNA clones which suppress for a defective G2 checkpoint function in a yeast mutant have been identified by this process.

An exemplary method for isolating and selecting human checkpoint cDNA clones that suppress a checkpoint mutation in a double mutant yeast test cell is conveniently conducted using the following steps. First, a double mutant test cell is constructed with a mutation in gene #1 that is "conditionally" responsible for DNA damage, and a mutation in gene #2 that causes a growing cell to fail to arrest the cell cycle at a checkpoint where a native (wild-type) cell would arrest if DNA damage was present. The mutation in gene #1 is thus made potentially lethal by the additional mutation in gene #2. "Conditionally," as used herein, is intended to mean that if the mutation in gene #1 is silent the cells grow normally, but when the mutation is induced to become active at a restrictive condition the cells undergo DNA damage. "Restrictive conditions" include, for example, shifting the temperature from a permissive to a restrictive temperature, or adding an inducer or activator that promotes expression of the DNA damage phenotype of the mutant of gene #1. Yeast double mutant test cells are constructed by mating the respective single mutants of gene #1 and gene #2 and by then selecting recombinants, e.g., using selectable markers. The yeast double mutant test cell has the following desirable phenotypic properties: under permissive conditions the cell grows, but when shifted to restrictive conditions DNA damage results; the mutation in gene #2 prevents cell cycle arresting to repair the damage, and chromosomal aberrations result. Preferably, the double mutant yeast test cells fail to grow under the restrictive conditions, and most preferably the double mutant test cells die when the restrictive conditions are imposed. Illustrative examples of double mutant test cells are provided by mec-1,cdc9-8 and rad9,cdc9-8. In both of the latter test cells the mutation in gene #1 is provided by cdc9, which is conditionally lethal at a restrictive temperature; and the mutation in gene #2 is a mec-1 or rad9 mutation capable of preventing G2 arrest in response to DNA damage. There are multiple cdc9 alleles; one preferred allele is provided by the cdc9-8$^{ts}$ strain. rad9 yeast mutants lack a functional RAD9 protein that is essential in yeast at a G2 checkpoint. The mec1,cdc9-8 or rad9,cdc9-8 double mutant test cells die more rapidly at 36° C. than RAD9,cdc9-8 or MEC1,cdc9-8, respectively. The latter two different illustrative double mutant yeast strains have been deposited: rad9,cdc9-8 cells as ATCC No. 74154; and mec-1,cdc8-9 cells as ATCC No. 74155.

Second, pooled human cDNA is inserted into a plasmid vector having a selectable marker under the control of a yeast promoter, and the vector is introduced into cultures of the yeast double mutant test cells, e.g., using lithium acetate transfection. Transformants are selected as individual colonies (based on marker expression and temperature), but en masse on microbiological culture plates. Next, tests are conducted to determine the plasmid dependence of the phenotypic expression (e.g., plasmid-dependent growth). In this case the yeast cells are "cured" of the plasmid and then tested for phenotype (e.g., viability or growth). The latter test results are used to ensure that the phenotype selected (e.g., growth or viability) in the transformant is dependent upon the presence of the human cDNA in a plasmid DNA, and not on some other random genetic event. In the illustrative examples it was necessary to isolate about 200,000 transformants so that sufficient transformants would be available for selection of the rare suppressor human cDNA clones.

Third, transformants from step 2 are tested to isolate the few colonies whose phenotype (e.g., viability or cell growth) is not conditioned by the activity of gene #1 (made lethal by the effects of gene #2). In this case the few transformants that are capable of growth have been rescued through the action of a human cDNA that either complements or suppresses gene #1 or gene #2. For example, with cdc9-8$^{ts}$ the conditional nature of the double mutant test cells is conveniently determined by assaying cell viability as a function of temperature. The rad9,cdc9-8 cells have a phenotype of rapid death at the restrictive temperature and less than 1 in 1000 of the human cDNA transformants survived the shift from the permissive temperature (23° C.) to the restrictive temperature (30° C.). "Suppression" of the double mutant yeast test cell phenotype (e.g., lack of growth and particularly lethality in this example) is intended to mean that the subject human checkpoint DNA increases expression of the phenotype (e.g., viability) of the rad9,cdc9-8$^{ts}$ double mutant without complementing either the rad9 gene or the cdc9-8 gene, with "complementation" requiring genotypic homology in order to rescue the phenotype.

Fourth, clones isolated under restrictive conditions are considered to be candidate clones for human checkpoint DNAs. Candidate clones are subjected to further phenotypic and nucleotide sequencing analysis to confirm their identity as human checkpoint clones. Three common methods (illustrated in the Examples, below) can be used to distinguish complementing cDNA clones from clones that exert their effects in the double mutant test cells via suppression:

First, cell viability of transformants may be compared with that of double mutant test cells, vector-transformed control cells, and double mutant test cells transformed by the native (wild-type) gene. The comparisons are conducted under different restrictive conditions (e.g., at different temperatures, such as 37° C., 34° C., or 30° C. for rad9, cdc9-8 cells). In the illustrative examples presented below, when complementing huCDC34 DNA (or the yeast MEC–1 gene) was introduced into a cdc34 cell (or mec–1 cell) the mutant acquired the growth characteristics of the native wild-type CDC34 or MEC–1 transformed cells. In contrast, human cDNAs exerting their effects on the double mutant test cells through suppression, rather than complementation, can exhibit distinctive differences in these comparative tests.

Second, growth rates of human transformants may be compared at different restrictive conditions with growth rates of vector-transformed control cells, and double mutant test cells transformed by the native gene. In this case the homolog should theoretically provide greater phenotypic expression than the suppressor cDNA; however, those skilled in the art will recognize that phenotypic expression of genes can be undependable.

Third, confirmation that a human cDNA acts by suppression, rather than complementation, is provided by sequencing the cDNA in the screened transformant (i.e., in the plasmid DNA from the transformant) and determining that the cDNA does not have a nucleotide sequence homologous with either gene #1 or gene #2. In all cases, complementing human cDNA clones are those that have a nucleotide sequence more than 35% and preferably more than 50% homologous with gene #1 (e.g., cdc9-8) or gene #2 (e.g., rad9 or mec–1). The three human checkpoint genes isolated are capable of correcting the deleterious effects of a mutant yeast checkpoint gene. While all three clones could correct the defect either by supplying the missing gene product (e.g., complementing with a homologous human gene product), or by substituting the missing yeast mutant checkpoint function with a different phenotypically compensating function (e.g., suppression), only the latter suppression has been observed. All three of the human cDNA clones isolated acted by suppression, and not complementation: i.e., clone #1, huCDC34 SEQ ID NO:7, suppressed the defect in mec1,cdc9-8; clone #2, huRAD9$_{compA}$ SEQ ID:8, suppressed the defect in rad9,cdc9-8 and mec1,cdc9-8 (and is not homologous to RAD9); and clone #3, huRAD9$_{compB}$ SEQ ID:9, suppressed the defect in mec1, cdc9-8 (and is not homologous to MEC–1).

Pursuant to the present disclosure, novel checkpoints for DNA repair may be identified through a variety of methods commonly known and used in the art. Similarly, methods are available for selecting novel checkpoint mutants.

DNA repair can result from DNA strand breaks induced by a variety of treatments, e.g., irradiation treatment with chemical agents or errors during DNA replication. Thus, DNA replication mutants are also useful (in place of DNA repair mutants) as sources of cells for constructing the subject double mutant test cells. Representative examples of DNA replication mutants include cdc2,cdc17, and cdc13. Other examples are described in Weinert et al., Genetics 134: 63–80, 1993.

The rad9,cdc9 and mec–1,cdc8-9 cells are also useful for identifying and isolating other novel human checkpoint genes, e.g., "huX", "huY", and "huZ", that suppress mutant checkpoint functions. These novel human checkpoint genes are, in turn, used to clone mouse genes "moX", "moY", and "moZ" from which mutant genes "mo$^x$", "mo$^y$", and "mo$^z$" may be constructed (e.g., by site-directed mutagenesis and screening for a defective "mo$^x$", "mo$^y$", and "mo$^z$" checkpoint function in the assay with the rad9,cdc9 or mec–1,cdc 9 cells). The mutant DNAs are in turn useful for constructing mutant murine cell lines (i.e., defective in a checkpoint function) in which DNA strand breakage can be induced, e.g., by radiation or drugs. The latter murine cells with DNA damage and a mutant checkpoint gene are useful for screening to identify novel human compensatory genes, e.g., "huA", "huB", and "huC". These genes may include human homologs of the native moX, moY, or moZ genes, and/or nonhomologous human genes that suppress moX, moY, or moZ without supplying the missing gene product per se. Those skilled in the art will recognize that this process of the invention is useful for identifying natural inhibitors, cofactors, accessory proteins, and dominant negative and positive regulatory genes affecting expression (e.g., genes that encode enzyme inhibitors of X, Y, or Z, dominant negative or positive transcriptional regulators, and accessory proteins, such as cyclins, that modify the function of a checkpoint gene product in the cell cycle). It is considered highly likely that novel tumor suppressor genes (e.g., similar to Rb, the retinoblastoma gene) will be included in the latter group of genes.

The subject human checkpoint DNAs that are isolated through the practice of the methods of the invention are useful in constructing stable test cell lines of yeast, E. coli, and mammalian cells that have the subject checkpoint DNAs stably integrated in their genomes. The latter test cells may be used for screening chemicals, candidate drugs, radiation, etc., for their effects on checkpoint gene expression. The subject human checkpoint genes are also useful for altering sensitivity of a cell to radiation- or drug-induced DNA damage. Increasing sensitivity of tumor cells to chemotherapeutic drugs and radiation may be desirable, i.e., to increase the lethality of low-dose radiation or a therapeutic drug. Conversely, decreasing sensitivity of patient bone marrow cells to the drugs or radiation may be highly advantageous, and the effect may be obtained by modifying the activity of a checkpoint gene product. For example, overexpression of a native (i.e., genetic wild-type; nonmutant) checkpoint gene in a cell may increase cellular resistance to DNA damage. In this case, the increased resistance may be achieved by introducing additional copies of the subject genes into a cell. While not wishing to be limited by any particular mechanism, overexpression of the subject checkpoint may confer increased resistance to DNA strand-breaking drugs, by enhancing cellular functions for: surveillance to determine if DNA is broken (i.e., a noncheckpoint gene); stopping or delaying mitosis so that DNA can be repaired (i.e., a checkpoint gene); and promoting DNA repair mechanisms (i.e., a noncheckpoint gene). Methods are provided herein for experimentally discriminating among these three alternatives.

In another illustrative example, decreasing expression of a human checkpoint gene in a cell (e.g., by introducing antisense embodiments of a checkpoint gene into the cell, or by introducing dominant negative modulators) may increase radiation sensitivity of the cell.

In another illustrative example, overexpression of a checkpoint gene in a malignant cell may be used to uncouple the downstream uncontrolled growth induced by an oncogene- or growth factor-mediated signal transduction pathway. Over-expression of a human checkpoint gene in a cell may be accomplished using drugs that activate the promoter of the checkpoint gene, or by using gene therapy vital vectors to introduce and alter expression of the human checkpoint gene in the target cell.

The invention also provides for diagnostic screening of cells, such as in tumor biopsy samples, to determine the level of checkpoint gene expression and rearrangement as an indicator of sensitivity of the (tumor) cells to DNA damage by radiation or chemotherapeutic drugs. Other uses of the subject checkpoint genes include gene therapy to increase radiation resistance of bone marrow cells (i.e., prior to transplantation into recipients who may need additional radiation or drug therapy; e.g., AIDS patients with malignant lymphoma). Assays are also contemplated for identifying chromosomal rearrangement of human checkpoint genes, e.g., in tumor cells and genetic deficiency diseases. Examples are provided of how FISH (fluorescence in situ hybridization) was used to map the far telomeric region of human chromosome 19p13.3. Since telomeric regions in chromosomes (teleosomes) are subject to frequent rearrangement from incomplete DNA replication and telomerase terminal extension, it is thought highly likely that mapping rearrangements of human checkpoint genes may be useful diagnostically for identifying the underlying cause of gene rearrangements in cancer predisposition syndromes and for identifying targets for gene therapy.

EXAMPLE 1

Cloning of a MEC$_{comp}$ and Identification as CDC34

In order for the cloning scheme to be successful, a cDNA source containing an intact checkpoint mechanism was required. The U118 glioblastoma cell line fulfilled this requirement, as shown by the results of experiments in which the cells were exposed to graded doses of cesium-137 gamma irradiation. Twenty-four hours after exposure of a logarithmically growing culture to 900 cGy, there was a clear accumulation of cells in G2 when compared to unirradiated controls.

A cdc9-8,rad9::HIS3,leu2 strain (9085-8-3) was constructed in order to select for RAD9 genes. rad9::HIS3 signifies a deletion mutant of the RAD9 gene by insertion of the HIS3 gene. This type of mutation has a very low reversion frequency. Phenotypic growth characteristics of double mutant yeast test cells and the single mutant cdc9-8 cells are shown in Tables 1 and 2, below.

TABLE 1

Temperature dependence of growth of mutant strains of S. cerevisiae.

| STRAIN | TEMPERATURE* | | |
|---|---|---|---|
| | 23° C. | 30° C. | 34° C. |
| cdc9-8,RAD+ | +++ | ++ | − |
| cdc9-8,rad9 | +++ | − | − |
| CDC+,rad9 | +++ | +++ | +++ |

*Log phase liquid cultures grown at 23° C. were diluted and spread onto plates containing rich media, after which the plates were incubated at the indicated temperatures for three days. Growth is scored as +++, large colonies, ++, small colonies, −, no colonies/no growth.

TABLE 2

Temperature dependence of viability of mutant strains of S. cerevisiae.

| STRAIN | TEMPERATURE* | | | |
|---|---|---|---|---|
| | 23° C. | 30° C. | 34° C. | 36° C. |
| mec1,cdc9-8 | 100% | <0.01% | ND | ND |
| rad9,cdc9-8 | 100% | <0.1% | ND | ND |
| cdc9-8 | 100% | 100% | 10% | <0.10% |

*Percent viable cells after 3–5 days.
ND, not determined.

We also obtained a cdc9-8,mec1-A401,leu2 strain (171-10-2) for selection of MEC1 function. No deletion mutant of mec1 was available. The mec1-A401 allele is a radiation-sensitive mec1 allele that has effects similar to the rad9 mutation on the growth of cdc9-8.

The experimental design was as follows. Log phase cultures of the yeast test strains grown at 23° C. were made competent for transformation by the lithium acetate method. Transformation of the strains was performed with the ADANS vector (control) or DNA from the pooled cDNA library. The transformed yeast was spread on plates with leucine-deficient media at 23° C. for 20–24 hours to select for those yeast which had taken up the DNA and allow expression of the cDNA insert. The plates were then transferred to a 30° C. incubator and allowed to grow for five to seven days.

Control experiments in which the cdc9-8,rad9::HIS3,leu2 strain was transformed with the ADANS vector alone showed that only one in ten thousand LEU+ cells would grow at 30° C. under these conditions. The background rate (number of cells growing at 30° C. after transformation with the vector alone) for the cdc9-8, mec1-A401,leu2 strain was one in five to ten thousand and somewhat more variable.

A series of transformations of the cDNA library into the two test strains were performed. Any colonies that grew within five to seven days at 30° C. were streaked out for single colonies, and plasmid dependence for growth at 30° C. was determined. This was accomplished by growing the transformants nonselectively in liquid culture (rich media at 23° C.) and then plating on rich media to allow spontaneous loss of the plasmid. Replica plating to minus leucine or rich plates at 30° C. demonstrated whether growth at 30° C. required the presence of the plasmid. Plasmid dependence was confirmed by isolating the plasmid from the yeast transformant, amplifying the DNA in E. coli, and retransforming the original yeast strains and selecting for growth at 30° C.

After screening approximately two hundred thousand cDNAs for complementation of the mec1,cdc9-8 strain, there were 15 primary transformants, only one of which (named 171tx6) showed plasmid dependence for growth at 30° C. Transformation of the cdc9-8, mec1 strain with 171tx6 DNA revealed that approximately 20–30% of the LEU+ colonies grew at 30° C. compared to a control of less than 0.1%. Transformation with a plasmid containing the authentic yeast MEC1 gene under its own promoter resulted in nearly 100% viability at 30° C. However, the selection scheme could potentially select for human DNA ligase cDNAs, which can complement the mutant yeast DNA ligase. Transformation of a cdc9-8,MEC+ strain did not show any evidence that 171tx6 was complementing the ligase mutation directly (e.g., the maximum permissive temperature was still 30° C.). The growth phenotype of transformants having the 171tx6 DNA, or subclone 171tx61 DNA, are shown in Table 3 below.

TABLE 3

Suppression of a lethal growth phenotype in S. cerevisiae mutants by transformation with huCDC34 (171tx61).

| CELLS | VECTOR | TEMPERATURE* | |
|---|---|---|---|
| | | 23° C. | 30° C. |
| mec1,cdc9-8 | control ADANS | + | − |
| | 171tx6 | + | + |
| | 171tx61 | + | + |
| rad9,cdc9-8 | control ADANS | + | − |
| | 171tx61 | + | + |

*Growth, determined by colony assays similar to those presented in Table 1;
+, growth;
−, no growth.

Due to the manner in which the library was constructed, there were three unique cDNA inserts in the 171tx6 clone. Each was subcloned into the ADANS vector, and only one of these cDNAs was active (171tx61) in the complementation assay. Sequence analysis of the 171tx61 cDNA insert revealed a striking homology between 171tx61 and the yeast cell cycle gene CDC34, with a 50% perfect conservation of amino acids in the 110 amino acid conserved core. A lesser homology to other members of this family of proteins was also observed. This family of proteins encodes the ubiquitin ligase E2 enzymes that are an integral part of the complex that targets ubiquitin to cellular proteins. Other members of the E2 family include RAD6, UBC4, and UBC5. 171tx61 did not show any homology to the yeast mec1 gene. Southern blot analysis with this cDNA as probe revealed substantial cross-species hybridization between human, mouse, chicken and Drosophila DNA, and a pattern suggesting only a single gene (data not shown). In addition, a single 1.8 kb transcript has been detected in several cell lines by Northern blot analysis (data not shown).

Interestingly, the human 171tx61 nucleotide sequence terminates prior to the carboxy-terminal region of the yeast CDC34 gene and prior to an Asp rich region that was thought essential for CDC34 protein and in particular ubiquitin conjugating activity. Since huCDC34 protein appears functional in yeast, the results suggest that the COOH terminus is not requisite for enzymatic activity.

In order to determine if 171tx61 was the human homologue of CDC34, we obtained a cdc34 temperature-sensitive yeast strain from Breck Byers. Transformation of this strain with 1 71tx61 revealed almost 100% complementation of the cdc34 mutation, allowing rapid growth of the temperature-sensitive strain at 37° C. See Table 4.

TABLE 4

Complementation of growth of an of S. cerevisiae cdc34 mutant by transformation with huCDC34

| | TEMPERATURE* | |
|---|---|---|
| VECTOR | 30° C. | 37° C. |
| control ADANS | + | − |
| 171tx61 | + | + |

*Growth, determined by colony assays similar to those presented in Table 1;
+, growth;
−, no growth.

Complementation of the cdc34 mutation by the 171tx61 cDNA appeared specific for the CDC34 member of the E2 family, as it did not complement the radiation sensitivity of a rad6 mutant strain. Thus, we consider 171tx61 the human homolog of cdc34 and renamed it huCDC34. Complementation of the mec1-A401 mutation was unique to the human CDC34. Expression of the S. cerevisiae CDC34 gene from the ADANS expression vector showed no complementation or suppression of the lethal phenotype in mec1,cdc9-8 (e.g., growth at 30° C.) (data not shown). Ubiquitin conjugating enzymes were not previously thought to function at checkpoints in the G2 phase of the cell cycle.

The mechanisms by which overexpression of the huCDC34 protein results in the complementation of the mec1-A401,cdc9 strain are presently under investigation. A current hypothesis is that overexpression of CDC34 results in a slowing of the normal cell cycle, in particular a lengthening of late S or G2 phase(s) allowing the mutant cdc9 more time to function. Consistent with this hypothesis, the doubling time of the mec1 strain containing the ADANS control vector was 120 minutes, while that strain containing the huCDC34 had a doubling time of 160 minutes. (Comparing doubling times is a method by which certain complementing and suppressing human cDNA clones may be distinguished from one another.)

The sequence of the 1374 basepair tx61 cDNA encoded one long open reading frame of 298 amino acids, which was in frame with the first 14 amino acids of the ADH gene resulting in a fusion protein. Surprisingly, analysis of the translated sequence with the PATMAT homology program revealed a high degree of homology to the S. cerevisiae cell cycle gene CDC34 and several other members of the ubiquitin ligase (UBC) family. There is 50% perfect homology between tx61 and CDC34 in the 108 amino acids flanking the active site cysteine. Multiple alignment analysis of tx61 with CDC34 (UBC3), RAD6 (UBC2), and UBC5 revealed that the human tx61 is most closely related to yeast CDC34, and yeast CDC34 is more related to tx61, than the other yeast members of the family. For example, there is an insertion in the CDC34 (12 amino acids) and tx61 (13 amino acids) proteins between the two highly conserved regions surrounding the active site, which is not found in most other members of the family. In addition, they share a highly acidic carboxy terminal end that distinguishes a subgroup of the UBC genes (CDC34 and RAD6) from the other UBC genes. The wheat germ UBC7 gene is also very homologous to tx61 but does not have the acidic carboxy terminal end. Interestingly, the human 171tx61 nucleotide sequence terminates prior to the carboxy-terminal region of the yeast CDC34 gene, and prior to an Asp rich region that was thought essential for CDC34 protein and in particular ubiquitin conjugase activity. Since huCDC34 protein appears functional in yeast the results suggest that the COOH terminus of huCDC34 protein is not requisite for ubiquitin conjugase enzymatic activity.

Southern blot analysis using the human CDC34 cDNA as a probe revealed specific hybridization to one or a few bands in human, mouse, and hamster genomic DNA. A polymorphic pattern was observed with this probe in different normal human genomic samples confirming utility as an RFLP chromosomal marker. Hybridization to chicken genomic DNA was also detected, as was weak hybridization to Drosophila melanogaster DNA, but not to any lower species including S. cerevisiae.

Northern blot analysis of several human cancer cell lines reveals hybridization to a unique band of approximately 1.4 kb in length, suggesting that the tx61 cDNA was nearly full length. Poly A+ RNA from two human neuroblastoma cell lines (SK-M-KCNR and SK-N-AS) and multiple hematopoeitic tumor cell lines was assayed. Human CDC34 was expressed in all of these lines as expected for a cell cycle regulatory gene, and quantitation revealed only two to fourfold differences among these lines. In addition, RNA from SMS-KCNR cells, which have differentiated and exited the cell cycle after treatment with retinoic acid, showed no decrease in the expression level of huCDC34 mRNA. SK-N-AS cells that are resistant to retinoic acid also show no decrease in huCDC34 mRNA expression after treatment with retinoic acid. Thus, no evidence for decreased transcription of human CDC34 was found when cells were not cycling.

To further characterize the human CDC34 gene, two overlapping genomic cosmid DNA clones (34cos2 and 34cos4) were isolated that are homologous to the human CDC34 cDNA. The cosmid clones were identified by screening a human placental cosmid library. That these cosmids represented the human CDC34 gene, and not some other gene, was confirmed by comparison of the restriction map of the cosmids and genomic DNA when probed with the CDC34 cDNA.

Hybridization by fluorescence in situ hybridization (FISH) with cosmid 34cos2 showed positive results in 41 of 42 metaphase human lymphocyte cells examined. The FISH signals were localized to chromosomes 19 at band p13.3 and in the telomeric end of band 19p13.3. One metaphase cell had signals on only one chromosome 19. Hybridization with cosmid 34cos4 demonstrated signals on both chromosome 19 homologs in 38 of 40 metaphase cells examined, and on only one chromosome 19 homolog in the other 2 cells. The signals from 34cos4 were also located at the very telomeric end of band 19p 13.3 and were indistinguishable from the signals generated from hybridization with 34cos2. There was no significant hybridization to any other human chromosomes.

An independent confirmation of this chromosomal localization was obtained by Southern blot analysis of human hamster somatic cell hybrids containing a single normal human chromosome 19. Hybridization with the human CDC34 cDNA revealed hybridization to the same bands in total human genomic DNA and the chromosome 19 hybrid.

Human CDC34 cDNA has also been used to map the location of the homologous gene in the mouse genome: the location is at chromosome 11D by RFLP analysis of interspecific crosses using four different polymorphisms. This region of mouse 11 is highly syntenic to human chromosome 17q. Given these results, the genomic DNA from a human chromosome 17 mouse somatic cell hybrid was also probed with the human CDC34 cDNA, but no hybridization signal was detected (other than that expected for the mouse genome).

The finding that the human homolog of the yeast protein CDC34 complements a mec1 mutation was surprising. The cdc34 mutation causes cells to arrest at the G1/S boundary after the activity of START. The arrested cells accumulate multiple buds but do not initiate DNA synthesis. There has been no reason to suspect that CDC34 plays a role in any phase of the cell cycle other than G1, and, given the essential nature of CDC34 at G1/S, there was no reason to look for an effect of a cdc34 mutation on a G2 checkpoint.

One question from the above results was whether the yeast CDC34 protein (rather than human) might have a compensating effect on the mec1,cdc9-8 strain similar to that of huCDC34. Initial attempts at compensation used a plasmid containing the S. cerevisiae CDC34 gene under its own promoter showed no compensatory effect on the double mutant cells. To overexpress the yeast CDC34 gene in a manner similar to the experiment with the huCDC34, a fragment of the yeast CDC34 gene was subcloned that contained the entire open reading frame downstream from an ADH promoter in an ADANS vector. This construct, scCDC34, efficiently complemented the cdc34ts mutation but very surprisingly had no effect on the mec1,cdc9 strain for growth at 30° C. in numerous experiments.

Further studies were conducted to characterize the interaction of the huCDC34 DNA with the phenotype expressed by the mec1 mutant. One model considered that the effect of overexpressing huCDC34 in the mec1,cdc9 strain might be nonspecific, e.g., a slowing of the cell cycle by huCDC34 that allows enough time for the mutant DNA ligase to work. To address this hypothesis, the doubling times of logarithmically growing cultures of mec1 strains were measured at 30° C. in the presence of plasmids. The doubling time was prolonged approximately 30%, i.e., from 2 hours with the control vector to 2 hours and 20 minutes with the huCDC34, but FACS analysis of propidium iodide stained yeast cells did not show significant differences in DNA content between the control vector transformed and huCDC34 transformed cells. Thus, it was reasoned that if slowing the cell cycle by only 20 minutes was sufficient to suppress for the mec1, cdc9-8 defects, then one might expect that an even less noticeable effect would be seen if cells were arrested for a longer period of time. As a test model, it was found that raising the temperature of a mec1,cdc9-8 strain to 37° C. resulted in rapid lethality with less than 0.1% viability after 6 hours, while a MEC+,cdc9-8 strain showed much slower loss of viability, i.e., 5% loss in viability after 6 hours. When huCDC34 transformants were tested in this assay system, it was found, unexpectedly, that huCDC34 partially restored viability to the mutant mec–1,cdc9-8 background, even after 6 hours at elevated temperature. Thus, a nonspecific slowing did not appear responsible for the compensatory effects of huCDC34.

Interestingly, expression of the huCDC34 gene does not suppress for the other two phenotypes of a mec1 strain, namely, radiation sensitivity and hydroxyurea sensitivity. Comparison of transformants, double mutants, and DNA-repair mutants for effects of drugs or irradiation on the cell cycle is another method by which complementing human cDNA clones may be distinguished from compensating cDNA clones by virtue of phenotypic similarities and differences, respectively. The survival curves are superposable for a mec1 strain transformed with a control vector or the huCDC34 DNA and then exposed to graded doses of radiation. In contrast, a mec1 strain carrying a MEC1 plasmid or a wild type strain with the control vector are radiation resistant. Similarly, transformation with huCDC34 DNA had no effect on hydroxyurea sensitivity (mec1 strains are unique among the known G2 checkpoint mutations in their exquisite hydroxyurea sensitivity).

The following results support the concept that the effect of the huCDC34 gene on the mec1 phenotype is specific: huCDC34 DNA does not suppress for a rad9,cdc9-8 strain at 30° C. or a MEC+,cdc9-8 strain at 34° C.; and, transformation with the huCDC34 DNA decreases the lethaiity of a mec1,cdc9-8 strain even after 6 hours at the nonpermissive temperature. Surprisingly, the yeast CDC34 gene does not have the effects that huCDC34 has on the mec1 strain. Even when overexpressed there is no effect of yeast CDC34 on the mec1,cdc9 8 strain at 30° C. By way of explanation, perhaps the huCDC34 protein is less specific than its yeast counterpart and it is able to ubiquitinate a cyclin during the G2 phase of the cell cycle. In this manner the huCDC34 protein may delay the cell cycle and suppress the lethal phenotype in the mec1,cdc9-8 cells.

It was also found that although the huCDC34 gene had a significant effect on the cdc9 mutant (defective in DNA ligase), it had no effect on radiation sensitivity or hydroxyurea sensitivity of a mec1 strain. Two additional human checkpoint cDNAs were isolated ($RAD9_{compA}$ and $RAD9_{compB}$); see Example 2 below. It is proposed that yeast possesses separate mechanisms for creating the cdc9 checkpoint and the radiation checkpoint, although both pathways must utilize MEC1 and RAD9.

The G1 target(s) of yeast CDC34 is unknown. A possible S or G2 target of human CDC34 is one of the B-type cyclins, CLB1-6, of S. cerevisiae that contains a ubiquitin targeting signal. Several of these cyclins have been found to be expressed at a high level in both the S and G2 phases of the cell cycle.

The data maps the location of CDC34 to the far telomeric region of the short arm of human chromosome 19. The telomeric location of this cell cycle gene in humans is intriguing given the role of telomeric shortening in cellular senescence. A recent model of senescence proposes that repression of essential genes found near the telomere occurs by a change in chromatin structure as telomeres shorten. It is instructive to determine how close to the 19p telomere the human CDC34 is located, as well as the expression of this gene in cells that are nearing senescence.

In contrast to the human mapping data, mapping of this gene in the mouse places it in a nontelomeric position on chromosome 11D. This region maps to a long region of synteny on human chromosome 17q, but we do not find any evidence for a CDC34 homolog on human chromosome 17; thus CDC34 defines a new region of homology between mouse chromosome 11 and human chromosome 19.

This is the first human homolog identified of the group of genes (CDC34, CDC4, and CDC53) required for the late G1 to S transition in budding yeast. Absence of any one of these functions results in cell cycle arrest before DNA synthesis is initiated and the formation of multiple pseudobuds. Identification of the components of the G1 to S transition in human cells will be essential for defining how the initiation of DNA synthesis is regulated and the mechanisms that control the G1/S transition after DNA damage.

EXAMPLE 2

Isolation of Human Genes huRAD9$_{compA}$ and huRAD9$_{compB}$

A fundamental aspect of radiation resistance is the capacity of cells to detect DNA damage and delay entry into mitosis for a time sufficient to repair the damage. Failure of this mechanism results in unrepaired DNA damage and cell death during mitosis. Both the RAD9 and MEC-1 genes play an integral role in the DNA repair surveillance mechanism, and isolation of human CDC34 as a compensatory cDNA clone for the MEC1 yeast gene is described above. The experiments described below were designed to identify and investigate human cDNA clones complementing or compensating for the function of the yeast RAD9 gene in mediating radiation resistance.

Human RAD9$_{compA}$:

In an attempt to clone compensating and complementing RAD9 cDNAs, approximately 300,000 LEU+ human cDNA transformants of the rad9,cdc9-8 strain were screened. Forty-five transformants were identified that grew at 30° C. These forty-five transformants were evaluated to determine the plasmid dependence of their growth, as described in the materials and methods below. One transformant (named 83tx42) was identified that showed plasmid dependence for growth at 30° C. When the plasmid was isolated and retransformed into the rad9,cdc9-8,leu2 strain, approximately 10% of the colonies grew at 30° C. compared to less than 0.1% of the control transfectants. Interestingly, when 83tx42 was transformed into the mec1,cdc9-8 strain, the cells showed similar levels of growth at 30° C. as 83tx42 in a rad9,cdc9-8 strain. Conversely, 83tx42 had no effect on the cdc9-8,RAD+,MEC+ strain suggesting that it did not directly complement the ligase mutation. 83tx42 contains an approximately 2 kb cDNA insert. Since the cDNA suppressed for the defects of rad9 in the cdc9-8, rad9 strain it was termed huRAD9$_{compA}$. The nucleotide sequence of huRAD9$_{compA}$ is shown in SEQ ID:8.

Human RAD9$_{compB}$:

In an attempt to identify additional clones compensating and complementing cDNAs, approximately 100,000 LEU+ human cDNA transformants of the mec1,cdc9-8 strain were screened. Twenty transformants were identified that grew at 30° C. These transformants were evaluated to determine the plasmid dependence of their growth (as described in the materials and methods below). One transformant (named 171tx23) was identified that showed plasmid dependence for growth at 30° C. When the plasmid was isolated and retransformed into the mec1,cdc9-8,leu2 strain, approximately 20% of the colonies grew at 30° C. compared to less than 0.1% of the control transfectants. Interestingly, when 171tx23 was transformed into the cdc9-8 strain, the cells showed similar levels of growth at 30° C. as in a mec1, cdc9-8 strain (Table 5, below). Conversely, 171tx23 had no effect on the cdc9 strain, suggesting that it did not directly complement the ligase mutation. 117tx23 contains an approximately 1.6 kb cDNA insert.

TABLE 5

Suppression of a lethal growth phenotype in S. cerevisiae mutants by transformation with huCDC$_{compB}$(171tx23).

| CELLS | VECTOR | TEMPERATURE* | |
|---|---|---|---|
| | | 23° C. | 30° C. |
| mec1,cdc9-8 | control ADANS | + | − |
| | tx23 | + | + |
| | MEC-1 | + | + |
| rad9,cdc9-8 | control ADANS | + | − |
| | tx23 | + | + |
| | RAD9 | + | + |

*Growth, determined by colony assays similar to those presented in Table 1; +, growth; −, no growth.

The nucleotide sequence of 117tx23 is shown in SEQ ID:9. Clone #3 cDNA confers radiation resistance upon both the mec-1 and rad9 transformants. For this experiment, the mec1 or rad9,117tx23 transformants were exposed to 20 Grey or 60 Grey of X-irradiation; ADANS vector transformed mec1 or rad9 cells were used as controls. The clone #3 117tx23 transformed mec-1 or rad9 cells showed 20-fold greater survival after three days of culture.

EXAMPLE 3

Regulation of Human Cell Cycle Genes

Antibodies to the huCDC34 fusion protein were prepared, and antibodies to RAD9$_{compA}$ may be prepared by a similar method. To produce antibodies, the respective cDNAs were subcloned into prokaryotic GST expression vectors designed to produce large quantities of the protein in E. coli. The recombinant fusion proteins were used for immunization of rabbits for production of polyclonal antisera. Rabbits showing a positive ELISA response to the fusion protein were boosted with thrombin-treated fusion protein. (The GST region of the fusion protein is thrombin sensitive.) Anti-huCDC34 had an endpoint ELISA titer of $10^4$. Antibodies are useful in assays evaluating the level of expression of the RAD9 and MEC–1 genes at the protein level. For instance, antisera to huCDC34 and huRAD9$_{compA}$ is useful in Western blot and immunoprecipitation analyses with protein extracts of mammalian cell lines. Such experiments provide information regarding expression of these genes and how post-translational modification, e.g., phosphorylation and glycosylation, may alter expression. In particular, expression assays may be performed in cells before and after irradiation to monitor for changes in the levels of proteins and how changes in checkpoint gene expression correlate with radiation sensitivity or resistance of cells.

To address whether increased expression (overexpression) of a checkpoint gene in a mammalian cell may increase the radiation resistance of the cell, huRAD9$_{compB}$ cDNA was inserted into the pLXSN retroviral vector. The huRAD9$_{compB}$ DNA is under the control of the MuLVLTR promoter. The vector is useful for monitoring changes in G2 arrest and radiation sensitivity of retroviral vector transduced mammalian cells, as compared to that of control pLXN vector transduced control cells.

To show that huRAD9$_{compB}$ plays an important role in radiation sensitivity, hurad9$_{compB}$ mutant mammalian cells are constructed and the mutation is correlated with increased sensitivity of the cells to graded doses of radiation.

Negative selection, i.e., for down-regulation or negative-regulators of RAD9, huCDC34, huRAD9$_{compA}$, or huRAD9$_{compB}$ function, is accomplished in a yeast screening assay. For example, cdc13-1 is a temperature-sensitive *S. cerevisiae* cell cycle mutant that causes arrest late in G2 if cells with the mutant genotype are shifted to the restrictive temperature. The maximum permissive temperature for cdc13, i.e., the temperature that still allows colonies to form in a yeast with normal RAD9 function, is 25° C. However, in cdc13 strains in which RAD9 is also deleted the maximum restrictive temperature increases to 28° C. (Presumably, at 28° C. RAD9 acts on problems due to the cdc13 mutation and arrests the cells in G2.) In the absence of RAD9, the cells continue to cycle and the cdc13 damage does not make the cells nonviable. Above 28° C., the cdc13 RAD+ or rad9 strains do not grow. The result of this effect is that one can select against RAD9 function by growing a cdc13,RAD+ strain at 28° C. and isolating colonies that can grow at 28° C. Although the difference between the restrictive and permissive temperatures is only three degrees, it has been found that less than one per thousand cdc13,RAD+ cells will grow at 28° C., as contrasted with growth of almost 100% of cdc13,rad9 cells. Using such negative selection, two methods are possible for isolating dominant cDNAs that negatively regulate RAD9. The first is to randomly mutate the plasmid containing the yeast RAD9 cDNA. The pool of mutagenized plasmids is transformed into the cdc13,leu2, RAD+ strain and selected for growth at 28° C. The plasmid from any colony that grows at 28° C. is isolated and retested in the same assay. Sequence analysis of active clones is performed to determine what mutation has occurred. The mutant RAD9 gene is then transfected into wild-type yeast and the changes in radiation sensitivity and G2 arrest determined. The goal is to find a mutant RAD9 that can interfere with the function of a normal RAD9 and increase radiation sensitivity. Dominant negative mutants can act by binding the normal protein and forming nonfunctional heterodimers if the protein is normally a homodimer, or by directly interacting with the normal target of the RAD9 gene.

An alternative approach is to directly mutate a huCDC34, huRAD9$_{compA}$, huRAD9$_{compB}$, or huRAD9 gene and then to transform the cdc13,leu2,RAD+ strain with pooled cDNAs from a library and select for growth at 28° C. This method allows selection of unique clones which, when overexpressed, may interfere with the function of one or more of the four human cDNAs. Similarly, clones isolated in this manner can be sequenced and tested for their effect on radiation resistance and G2 arrest in wild-type yeast.

Any RAD9 or cDNA clone that has a dominant negative effect on radiation sensitivity in yeast may be subcloned into a mammalian expression vector and transfected into cell lines with moderate to high radioresistance, such as HeLa S3 and U118. Stable lines in which the transfected genes are highly expressed may be isolated along with cell lines containing vector controls, and the radiation sensitivity of the cell lines may be determined and compared. Given that deletion of the RAD9 gene in yeasts does not affect viability, it is expected that transfectants will be viable. Changes in cell survival after irradiation and G2 arrest are determined. The goal is to create molecules that actively decrease radiation resistance of tumor cells by interfering with the normal checkpoint function. These molecules represent unique reagents that can decrease radiation resistance in vivo and may have therapeutic efficacy.

Materials and Methods

Assay Strategy:

A simple genetic assay was developed for selecting human checkpoint genes by complementation of defined yeast mutations. In addition to radiation sensitivity, the presence of a checkpoint mutation increases the lethality of several temperature-sensitive cell cycle mutations. The presence of either a rad9 or mec1 mutation decreases the maximum permissive temperature (from 30° C. to 25° C.) of a strain with a DNA ligase mutation (cdc9-8). Presumably, the increased lethality of the checkpoint mutation is a consequence of cells with multiple DNA strand breaks entering mitosis. Thus, after transformation with a human cDNA library, selection for growth at 30° C. of a mec1, cdc9-8, or rad9,cdc9-8 strain will allow selection for cDNAs that suppress for or complement the MEC1, RAD9, or CDC9 function.

Human cDNA Library:

A human cDNA library was obtained in which the yeast expression vector ADANS contained an ADH promoter and first 14 amino acids of the ADH gene flanking the human cDNA insert and the promoter was followed by a LEU2 selectable marker gene. The source of cDNA was the human glioblastoma U118 cell line, which maintains an intact G2 arrest mechanism after irradiation.

Transformation of cdc9-8,mec-1:

Logarithmically growing cultures of a mec1,cdc9-8,leu2 strain were transformed with DNA from the cDNA library using the lithium acetate method. The cultures were plated and selected for growth on leucine-deficient media at 30° C. Five days after transformation of the mec1,cdc9-8 strain with the control ADANS vector less than 0.1% of LEU$^+$ transformants formed a colony at 30° C. Transformation with the human tx6 cDNA or its subclone, tx61, resulted in 10–20% viability of LEU+ transformants at 30° C.; for comparison, transformation with the authentic MEC1 gene results in near 100% viability at 30° C.

Yeast and Bacterial Strains:

The *S. cerevisiae* strains described in these experiments were congenic with A364a. Sources of the strains are indicated: 171-10-2 (MATa, cdc9-8, mec1-A401, leu2, ura3, ade2 ade3, trp1- T. Weinert), 9085-1-8-3 (MATα, cdc9-8, rad9::HIS3, leu2, ura3, trp1), 9085-1-10-4 (MATα, cdc9-8, leu2, his3), SJ1098-3d (MATa, cdc34-2, leu2-3, ura3, trp1- B. Byers). All bacterial transformations were performed in the SURE strain (Stratagene, La Jolla, Calif). DNAs: A human placental cosmid library in pWE15 was obtained. The S.c. CDC34 plasmid was constructed by subcloning a PCR amplified 1.0 kb piece of the CDC34 gene downstream of the HindIII site in the ADANS plasmid. The MEC1 and RAD9 plasmids were provided by T. Weinert. Somatic cell hybrid DNAs were obtained from the Coriell Cell Repository (Camden, N.J.). Both the human chromosome 19 hybrid (GM10449, #5HL9-4) and the human chromosome 17 hybrid (GM10498, #MN-22.6) contain greater than 90% of cells with a single human chromosome, and the chromosome 19 hybrid was negative by Southern blot analysis for a known chromosome 17 marker. The sequence of both strands of the cDNA insert was determined by dideoxy sequencing using Sequenase 2.0 (US Biochemical, Cleveland, Ohio).

Yeast Transformation:

Logarithmic cultures of the indicated strain were transformed according to a modification of the method of Schiestl and Gietz (6), in which the DNA and 50% PEG solution are added directly to the yeast in lithium acetate without any preincubation. Plasmid DNA from yeast was extracted by glass bead disruption and transformed into *E. coli* by electroporation (Bio Rad, Hercules, CA). Plasmid DNA from a single colony was retransformed into the parent yeast strain to check for plasmid dependence.

Northern and Southern Analysis:

Total genomic DNA was restricted according to the manufacturer's recommendations and separated on 0.7% agarose gels with TBE buffer. Transfer to GeneScreen Plus and hybridization was performed according to manufacturer's recommendations (NEN, Boston, Mass.). The most stringent wash was 0.2× SSC plus 1% SDS at 65° C. The human CDC34 probe was a 784 bp PCR product labeled by random oligonucleotide-primed synthesis (Boehringer Mannheim, Indianapolis, Ind.). The oligonucleotides used to generate the PCR product are 5'-AACACCTACTACGAGGGCGGC-3', complementary to SEQ ID NO:7, nucleotides 1019–1040, and 5'-GCCCGTCCACCGAGCCCCGAG-3' identical to SEQ ID NO:7, nucleotides 256–276. Poly A+ RNA, a gift of Carol Thiele, was separated on 1% agarose, formaldehyde gels, and also transferred to GeneScreen Plus membrane. The filter was sequentially hybridized with the human CDC34 PCR probe and a rat GADPH cDNA. Quantitation of the hybridization signal on the Northern blot was performed by direct phosphorimaging of the hybridized filter (Molecular Dynamics, Sunnyvale, Calif.).

Fluorescent In Situ Hybridization:

As described previously (7), posthybridization washes were performed at 42° C. and 50° C. for 34cos2 and 34cos4, respectively.

EXAMPLE 4

Description for Yeast Checkpoint Control Genes

We have cloned and sequenced five new genes that are necessary for the G2/M checkpoint control. See SEQ ID NOS: 1–6, and 10–19. These genes, RAD17, RAD24, MEC1, MEC2, and MEC3 are responsible for recognizing if the cell has suffered DNA damage in the form of radiation or chemical damage or if the cell has failed to complete DNA replication because of chemical inhibition or intrinsic error. Upon recognizing damage or failure these genes are responsible for inhibiting mitosis. The purpose of this checkpoint control is that it preserves the viability of the cell and the integrity of the genome by providing the cell time to repair these insults prior to undertaking mitosis. These genes are potentially useful in developing cancer chemotherapeutic agents, cancer chemoprevention agents, and environmental toxicology tests. The genes can be used to produce proteins that can then be screened for chemical agents that would interfere with checkpoint controls. Such tests could be carried out in vitro or in vivo. Also the cloned genes can be used to develop yeast strains in which these genes are deleted and such yeast strains can then be used to find the homologous human genes (according to the procedures described above). The deleted yeast strains can also be used as hosts for the homologous human genes in which agents that inhibit the human gene products are being sought.

The ultimate goal of detecting agents that interfere with these checkpoint genes is as follows. In cancer chemotherapy such inhibitors would be expected to enormously enhance the efficacy of the commonly used chemotherapeutic agents and permit their use at much lower and less toxic doses. In cancer chemoprevention, agents that enhance a checkpoint control function could be given to patients in order to slow or prevent the evolution of tumor cells to more malignant forms. In environmental toxicology, one would screen for agents that inhibit checkpoint controls because such agents would be potentially carcinogenic.

Those skilled in the art will recognize that this process of the invention is useful for identifying natural inhibitors, cofactors, accessory proteins, and dominant negative and positive regulatory genes affecting expression (e.g. genes that encode protein inhibitors of checkpoint genes, dominant negative or positive transcriptional regulators, and accessory proteins such as cyclins that modify the function of a checkpoint gene product).

CITATIONS

1. Pringle, J. R. and Hartwell, L. H. 1981. The *Saccharomyces cerevisiae* cell cycle. In: *The Molecular Biology of the Yeast Saccharomyces: Life cycle and inheritance* (ed. J. N. Strathen et al.) Cold Spring Harbor Laboratory, Cold Spring Harbor, N.Y., p. 97.

2. Hartwell, L. H., 1973. *J. Bacteriology* 115:966–974.

3. Hartwell, L. H. and T. A. Weinert. 1989. Checkpoints: Controls that ensure the order of cell cycle events. *Science* 246:629–634.

4. Weinert, T. A. and L. H. Hartwell. 1988. The RAD9 gene controls the cell cycle response to DNA damage in *Saccharomyces cerevisiae. Science* 241:317–322.

5. Goebl, M. G., Yochem, J., Jentsch, S., McGrath, J. P. Varsharsky, A. and Byers, B. 1988. The yeast cell cycle gene CDC34 encodes a ubiquitin-conjugating enzyme. *Science* 241:1331–1335.

6. Schiestl, R. H. and Giets, R. H. 1989. High efficiency transformation of intact yeast cells using single stranded nucleic acids as a carrier. *Curr. Genet.* 16:339–346.

7. Chance, P. F., Alderson, M. K., Leppig, K. A., Lensch, M. W., Matsunami, N., Smith, B. et al. 1993. DNA deletion associated with hereditary neuropathy with liability to pressure palsies. *Cell* 72:143–152.

The embodiments of the invention in which an exclusive property or privilege is claimed are defined as follows:

1. A nucleotide sequence capable of hybridizing under stringent conditions with the huCDC34 nucleotide sequence of SEQ ID NO:7.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 1023 base pairs
        ( B ) TYPE: nucleic acid
        ( C ) STRANDEDNESS: single
        ( D ) TOPOLOGY: linear ( i i ) MOLECULE TYPE: cDNA to mRNA ( A ) DESCRIPTION: yeast RAD17 cDNA ( i i i ) HYPOTHETICAL: NO ( i v ) ANTI-SENSE: NO ( v i ) ORIGINAL SOURCE:
    ( A ) ORGANISM: Saccharomyces cerevisiae ( x i ) SEQUENCE DESCRIPTION: SEQ ID NO:1:

| | | | | | | |
|---|---|---|---|---|---|---|
| AGCAGGAATT | GGTAACGCCA | GGTTTTCCCG | ATCAGACGTT | GTAAAACAGG | CCAGTGAATT | 60 |
| GTAATACGAC | TCACTATAGG | GCGAATTGGG | TACCGGGCCC | CCCCTCGAGG | TCGACGGTAT | 120 |
| CGATAAGCTT | GATATCGAAT | TCCTGCAGCC | CCTAAAATGC | CATTTGTTCA | AATGGATCAA | 180 |
| ATTTCCCAAT | TTTTATCATT | TTCGAGAAAA | TATGGTGTGC | CTGAAGATGA | ACTGTTTCAG | 240 |
| ACAATTGATC | TTTTTGAGAA | AAAGGATCCT | GCCATTGTTT | TCCAAACGTT | GAAGTCACTA | 300 |
| TCTCGTTACG | CCAACAAAAA | ACATACAGAT | AGATTTCCAG | TTCTAGGACC | ACAACTGTCA | 360 |
| ACAAAGAAGC | CAAGACCCCC | GGTTAAGTCT | AAACCAAAAC | ATCTACAAGA | TGGTACTGGA | 420 |
| TGGAGCACTT | TTGAATACGG | TTATATGAAA | GGTGCATCTC | AGGCTACTGA | AGGAGTGGTG | 480 |
| TTAGGACAAC | GGAGAGATAT | AGTTTAGAGA | ATTATTATTA | ACACTTTCTC | TGGCAGAAAT | 540 |
| TGATAAATAA | ACATTTAAGA | ACCCTATATA | CGCAACCAAA | GTTCCTTTGA | TATATTTTAG | 600 |
| TTTTCCATCA | AAGTTTTCCT | ACATAAACAC | TAAGGTGGCT | AGAGACGCGT | AACAAAAGTT | 660 |
| AACGTTACCG | GTAAAAATGT | GATTATACAA | ATCAATCTCA | CAGAACGGTG | TGGAAACAAA | 720 |
| GTAGTTGAAG | GATTTCAACT | ATGCGAATCA | ACAGTGAGCT | AGCGAACAAG | TTTTCTGCCT | 780 |
| CAACGGTGCA | CTTAGAACAT | ATCACAACTG | CTTTAAGTTG | TTTAACACCT | TTTGGTTCTA | 840 |
| AAGACGATGT | GCTTATATTC | ATTGATGCTG | ATGGGCTGTC | ATTTGTCAGG | GAGAATAATC | 900 |
| ATGTGATAAA | AATCCAACTA | CTGTTATCTC | GGGAGCTATT | TATGTCTTAT | TCGTATAGAA | 960 |
| ATGAAACTGA | GGATCACATG | AAACTTTGTG | TAAAAATAAA | TCATATCTTA | GATAGCGTTA | 1020 |
| GCG | | | | | | 1023 |

( 2 ) INFORMATION FOR SEQ ID NO:2:

( i ) SEQUENCE CHARACTERISTICS:
        ( A ) LENGTH: 1021 base pairs
        ( B ) TYPE: nucleic acid
        ( C ) STRANDEDNESS: single
        ( D ) TOPOLOGY: linear ( i i ) MOLECULE TYPE: cDNA to mRNA
        ( A ) DESCRIPTION: yeast RAD24 cDNA ( i i i ) HYPOTHETICAL: NO ( i v ) ANTI-SENSE: NO ( v i ) ORIGINAL SOURCE:
        ( A ) ORGANISM: Saccharomyces cerevisiae ( x i ) SEQUENCE DESCRIPTION: SEQ ID NO:2:

| | | | | | | |
|---|---|---|---|---|---|---|
| GATCTTTTCC | TTTCGCTCTT | CAATATTACC | ATCCTCATTT | TCCTCATTTT | CTTCAATTGT | 60 |
| CTGATGAATA | TATCAGCAGT | TCCAATAATA | AGATCATGGG | GTATATCATT | GCCTAAAACT | 120 |
| TCTGTAACCC | ACTGCAAAAT | CTGCTCGTAA | GTTCGACAT | TTGAGGGATC | CTTTGGATAA | 180 |
| TAATGTAACC | TGAAATCGGA | GGAAGAATTC | AAAATGGTGT | TATGCTGCTG | AATTTTTTC | 240 |
| AATGATGCGC | TCTTTCCAGT | TTTTTCAACG | GCTACATCAT | TTTCTTTTAG | TCCTTTATTA | 300 |
| ATGTTATTGC | ACAGGCCCTG | TCCCATATCC | TTAGCACTAA | TTCTACCACT | CATGGATTTT | 360 |

-continued

```
GGTTGTGATA TTTCCGCATC CCTTTGAGGA TTTGGCTGGT ATTCATAAAG CGTTTATCAA    420
CTTTCAACAC CTTATTGGAC ATCTCATCAT AACGATAAAT TTCTCTAATT TTTTGGCCT     480
TATCCTTCGT TCATGCTCA GTCATTTTTA ATAACGAAGG CTCACGGTAA ATCTTCCAAA     540
GCAATTACTT ATATTTACCT TCACCTTATT TTACTCAAGA TTATCTCTAT TAGTGTATTA    600
TTCCTTTATA GTAGACATAG CTTTAGTAGC ATAAATTTTT AATATTCTCG TAAAGAGCGA    660
CAATATTCAA TATTAGATCG TCAAAGAAGC AAACACGCAT TGATATCTGA GAGATCATCA    720
CAATGCGTTA ATAGTACTTG ATTCAACACC ACTAATTATC AAGTTGTTC  CTGTCTGAAT    780
GATATGGATA GTACGAATTT GAACAAACGG CCCTTATTAC AATATAGTCT CAGTTCATTG    840
GGCTCGCAAA TAACAAAATG GAGCTCATCT AGACCGACTT CGCCAGTTCG TAAGGCGAGA    900
AGCACTGAAA ATGACTTTCT TTCCAAGCAA GATACGTCTA GTATCCTCCC AAGTATCAAC    960
GACGACGGCG GTGAACAGTG GTACGAAAAG TTCAAGCCCA ATTGTTTGGA GCAAGTGGCC   1020
A                                                                  1021
```

(2) INFORMATION FOR SEQ ID NO:3:

(i) SEQUENCE CHARACTERISTICS:
        (A) LENGTH: 1022 base pairs
        (B) TYPE: nucleic acid
        (C) STRANDEDNESS: single
        (D) TOPOLOGY: linear (ii) MOLECULE TYPE: cDNA to mRNA
        (A) DESCRIPTION: yeast MEC1 cDNA (iii) HYPOTHETICAL: NO (iv) ANTI-SENSE: NO (vi) ORIGINAL SOURCE:
        (A) ORGANISM: Saccharomyces cerevisiae (xi) SEQUENCE DESCRIPTION: SEQ ID NO:3:

```
ATAAGCTTAC TGACCAAGAA AGAGCACGCG TGTTGGAGTT TCAAGATTCC ATTCACTATT     60
CTCCGCGGTA CTCAGACGAT AACTATGAGT ACAGGCATGT GATGTTACCT AAGGCCATGC    120
TAAAAGTTAT CCCATCTGAT TACTTCAATT CGGAAGTGGG GACCCTGCGT ATATTAACAG    180
AAGACGAATG GAGAGGCCTC GGCATCACAC AGTCTTTGGG GTGGGAACAT TATGAATGCC    240
ATGCGCCAGA ACTACACATT TTGCTATTCA AAAGGCCGCT GAACTACGAG GCCGAGCTGA    300
GGGCAGCGAC CGCTGCTGCT CAACAGCAAC AGCAACAGCA GCAACAGCAG CAACAACAAC    360
AACAGCAACA TCAAACACAA TCGATTTCGA ACGATATGCA AGTTCCACCC CAAATCTCCT    420
AGCTTTGATA TACTCTAATT ACTGAAATTG AATTCCTTTT CAAGGCTCCA TAACTATATG    480
GAGCATACTA TGTACTTATC ATAATAAAGA ATAAACAAAC AAGCAAACAA AAAAAAAAA     540
AACTATGGAT CATAGTTTTC ACCAACAAGC ATTAGAATAC AAATAAAATT TATATAGTGA    600
ATATCCTTCA AATAAATTTC TTCTTTCCCT TATAAATCAA ATAGATGGAA CGCACGCTCC    660
AAAACTAGTC AACTAGAAAA AATACCCGC  CGACGGACAA TTTTGAAGAG AGATGATTAA    720
TGAAGACAAA GTGAGGCTGG ACAACAAGAA CGACATACAC CGCGTAAAGG CCCACAAGAC    780
TGCATGGAAT CACACGTCAA ATATCTTGAC GAATTGATAT TGGCAATAAA AGACCTGAAC    840
TCGGGGGTGG ATTCAAAGGT GCAGATTAAA AAAGTGCCCA CGGATCCATC TTCTTCTCAG    900
GAGTACGCCA AGAGTTTAAG ATCCTGAACA CCCTCATAAG AAACCTAAAA GATCAAAGAA    960
GGAACAATAT CATGAAAAAT GATACTATAT TTTCGAAAAC AGTTCCGCC  CTTGCCTTAT   1020
TG                                                                1022
```

( 2 ) INFORMATION FOR SEQ ID NO:4:

( i ) SEQUENCE CHARACTERISTICS:
        ( A ) LENGTH: 1023 amino acids
        ( B ) TYPE: amino acid
        ( C ) STRANDEDNESS: single
        ( D ) TOPOLOGY: linear ( i i ) MOLECULE TYPE: protein
        ( A ) DESCRIPTION: yeast MEC1 protein ( i i i ) HYPOTHETICAL: NO ( v i ) ORIGINAL SOURCE:
        ( A ) ORGANISM: Saccharomyces cerevisiae ( x i ) SEQUENCE DESCRIPTION: SEQ ID NO:4:

```
Met Glu Ser His Val Lys Tyr Leu Asp Glu Leu Ile Leu Ala Ile Lys
 1               5                  10                  15
Asp Leu Asn Ser Gly Val Asp Ser Lys Val Gln Ile Lys Lys Val Pro
             20                  25                  30
Thr Asp Pro Ser Ser Ser Gln Glu Tyr Ala Lys Ser Leu Lys Ile Leu
         35                  40                  45
Asn Thr Leu Ile Arg Asn Leu Lys Asp Gln Arg Arg Asn Asn Ile Met
 50                  55                  60
Lys Asn Asp Thr Ile Phe Ser Lys Thr Val Ser Ala Leu Ala Leu Leu
 65                  70                  75                  80
Leu Glu Tyr Asn Pro Phe Leu Leu Val Met Lys Asp Ser Asn Gly Asn
                 85                  90                  95
Phe Glu Ile Gln Arg Leu Ile Asp Asp Phe Leu Asn Ile Ser Val Leu
             100                 105                 110
Asn Tyr Asp Asn Tyr His Arg Ile Trp Phe Met Arg Arg Lys Leu Gly
         115                 120                 125
Ser Trp Cys Lys Ala Cys Val Glu Phe Tyr Gly Lys Pro Ala Lys Phe
 130                 135                 140
Gln Leu Thr Ala His Phe Glu Asn Thr Met Asn Leu Tyr Glu Gln Ala
 145                 150                 155                 160
Leu Thr Glu Val Leu Leu Gly Lys Thr Glu Leu Leu Lys Phe Tyr Asp
                 165                 170                 175
Thr Leu Lys Gly Leu Tyr Ile Leu Leu Tyr Trp Phe Thr Ser Glu Tyr
             180                 185                 190
Ser Thr Phe Gly Asn Ser Ile Ala Phe Leu Asp Ser Ser Leu Gly Phe
         195                 200                 205
Thr Lys Phe Asp Phe Asn Phe Gln Arg Leu Ile Arg Ile Val Leu Tyr
 210                 215                 220
Val Phe Asp Ser Cys Glu Leu Ala Ala Leu Glu Tyr Ala Glu Ile Gln
 225                 230                 235                 240
Leu Lys Tyr Ile Ser Leu Val Val Asp Tyr Val Cys Asn Arg Thr Ile
                 245                 250                 255
Ser Thr Ala Leu Asp Ala Pro Ala Leu Val Cys Cys Glu Gln Leu Lys
             260                 265                 270
Phe Val Leu Thr Thr Met His His Phe Leu Asp Asn Lys Tyr Gly Leu
         275                 280                 285
Leu Asp Asn Asp Pro Thr Met Ala Lys Gly Ile Leu Arg Leu Tyr Ser
 290                 295                 300
Leu Cys Ile Ser Asn Asp Phe Ser Lys Cys Phe Val Asp His Phe Pro
 305                 310                 315                 320
```

| | | | | | | | | | | | | | | |
|---|---|---|---|---|---|---|---|---|---|---|---|---|---|---|
|Ile|Asp|Gln|Trp|Ala<br>325|Asp|Phe|Ser|Gln|Ser<br>330|Glu|His|Phe|Pro|Phe<br>335|Thr|
|Gln|Leu|Thr|Asn<br>340|Lys|Ala|Leu|Ser|Ile<br>345|Val|Tyr|Phe|Asp|Leu<br>350|Lys|Arg|
|Arg|Ser|Leu<br>355|Pro|Val|Glu|Ala|Leu<br>360|Lys|Tyr|Asp|Asn|Lys<br>365|Phe|Asn|Ile|
|Trp|Val<br>370|Tyr|Gln|Ser|Glu|Pro<br>375|Asp|Ser|Ser|Leu|Lys<br>380|Asn|Val|Thr|Ser|
|Pro<br>385|Phe|Asp|Asp|Arg|Tyr<br>390|Lys|Gln|Leu|Glu|Lys<br>395|Leu|Arg|Leu|Leu|Val<br>400|
|Leu|Lys|Lys|Phe|Asn<br>405|Lys|Thr|Glu|Arg|Gly<br>410|Thr|Leu|Leu|Lys|Tyr<br>415|Arg|
|Val|Asn|Gln|Leu<br>420|Ser|Pro|Gly|Phe|Phe<br>425|Gln|Arg|Ala|Gly|Asn<br>430|Asp|Phe|
|Lys|Leu|Ile<br>435|Leu|Asn|Glu|Ala|Ser<br>440|Val|Ser|Ile|Gln|Thr<br>445|Cys|Phe|Lys|
|Thr|Asn<br>450|Asn|Ile|Thr|Arg|Leu<br>455|Thr|Ser|Trp|Thr|Val<br>460|Ile|Leu|Gly|Arg|
|Leu<br>465|Ala|Cys|Leu|Glu|Ser<br>470|Glu|Lys|Phe|Ser|Gly<br>475|Thr|Leu|Pro|Asn|Ser<br>480|
|Thr|Lys|Asp|Met|Asp<br>485|Asn|Trp|Tyr|Val|Cys<br>490|His|Leu|Cys|Asp|Ile|Glu<br>495|
|Lys|Thr|Gly|Asn<br>500|Pro|Phe|Val|Arg|Ile|Asn<br>505|Pro|Asn|Arg|Pro<br>510|Glu|Ala|
|Ala|Gly|Lys<br>515|Ser|Glu|Ile|Phe|Arg<br>520|Ile|Leu|His|Ser|Asn<br>525|Phe|Leu|Ser|
|His|Pro<br>530|Asn|Ile|Asp|Glu|Phe<br>535|Ser|Glu|Ser|Leu|Leu<br>540|Ser|Gly|Ile|Leu|
|Phe<br>545|Ser|Leu|His|Arg|Ile<br>550|Phe|Ser|His|Phe|Gln<br>555|Pro|Pro|Lys|Leu|Thr<br>560|
|Asp|Gly|Asn|Gly|Gln<br>565|Ile|Asn|Lys|Ser|Phe<br>570|Lys|Leu|Val|Gln|Lys<br>575|Cys|
|Phe|Met|Asn|Ser<br>580|Asn|Arg|Tyr|Leu|Arg<br>585|Leu|Leu|Ser|Thr|Arg<br>590|Ile|Ile|
|Pro|Leu|Phe<br>595|Asn|Ile|Ser|Asp|Ser<br>600|His|Asn|Ser|Glu|Asp<br>605|Glu|His|Thr|
|Ala|Thr<br>610|Leu|Ile|Lys|Phe|Leu<br>615|Gln|Ser|Gln|Lys|Leu<br>620|Pro|Val|Val|Lys|
|Glu<br>625|Asn|Leu|Val|Ile|Ala<br>630|Trp|Thr|Gln|Leu|Thr<br>635|Leu|Thr|Thr|Ser|Asn<br>640|
|Asp|Val|Phe|Asp|Thr<br>645|Leu|Leu|Leu|Lys|Leu<br>650|Ile|Asp|Ile|Phe|Asn<br>655|Ser|
|Asp|Asp|Tyr|Ser<br>660|Leu|Arg|Ile|Met|Met<br>665|Thr|Leu|Gln|Ile|Lys<br>670|Asn|Met|
|Ala|Lys|Ile<br>675|Leu|Lys|Lys|Thr|Pro<br>680|Tyr|Gln|Leu|Leu|Ser<br>685|Pro|Ile|Leu|
|Pro|Val<br>690|Leu|Leu|Arg|Gln|Leu<br>695|Gly|Lys|Asn|Leu|Val<br>700|Glu|Arg|Lys|Val|
|Gly<br>705|Phe|Gln|Asn|Leu|Ile<br>710|Glu|Leu|Leu|Gly|Tyr<br>715|Pro|Ser|Lys|Thr|Ile<br>720|
|Leu|Asp|Ile|Phe|Gln<br>725|Arg|Tyr|Ile|Ile|Pro<br>730|Tyr|Ala|Ile|Ile|Gln<br>735|Tyr|
|Lys|Ser|Asp|Val<br>740|Leu|Ser|Glu|Ile|Ala|Lys<br>745|Ile|Met|Cys|Asp|Gly<br>750|Asp|

| | | | | | | | | | | | | | | |
|---|---|---|---|---|---|---|---|---|---|---|---|---|---|---|
| Thr | Ser | Leu 755 | Ile | Asn | Gln | Met | Lys 760 | Val | Asn | Leu | Leu 765 | Lys | Asn | Ser |
| Arg | Gln 770 | Ile | Phe | Ala | Val 775 | Ala | Leu | Val | Lys | His | Gly 780 | Leu | Phe | Ser | Leu |
| Asp 785 | Ile | Leu | Glu | Thr | Leu 790 | Phe | Leu | Asn | Arg | Ala 795 | Pro | Thr | Phe | Asp | Lys 800 |
| Gly | Tyr | Ile | Thr | Ala 805 | Tyr | Leu | Pro | Asp | Tyr 810 | Lys | Thr | Leu | Ala | Glu 815 | Ile |
| Thr | Lys | Leu | Tyr 820 | Lys | Asn | Ser | Val | Thr 825 | Lys | Asp | Ala | Ser | Asp 830 | Ser | Glu |
| Asn | Ala | Asn 835 | Met | Ile | Leu | Cys | Ser 840 | Leu | Arg | Phe | Leu | Ile 845 | Thr | Asn | Phe |
| Glu | Lys 850 | Asp | Lys | Arg | His | Gly 855 | Ser | Lys | Tyr | Lys | Asn 860 | Ile | Asn | Asn | Trp |
| Thr 865 | Asp | Asp | Gln | Glu | Gln 870 | Ala | Phe | Gln | Lys | Lys 875 | Leu | Gln | Asp | Asn | Ile 880 |
| Leu | Gly | Ile | Phe | Gln 885 | Val | Phe | Ser | Ser | Asp 890 | Ile | His | Asp | Val | Glu 895 | Gly |
| Arg | Thr | Thr | Tyr 900 | Tyr | Glu | Lys | Leu | Arg 905 | Val | Ile | Asn | Gly | Ile 910 | Ser | Phe |
| Leu | Ile | Ile 915 | Tyr | Ala | Pro | Lys | Lys 920 | Ser | Ile | Ile | Ser | Ala 925 | Leu | Ala | Gln |
| Ile | Ser 930 | Ile | Cys | Leu | Gln | Thr 935 | Gly | Leu | Gly | Leu | Lys 940 | Glu | Val | Arg | Tyr |
| Glu 945 | Ala | Phe | Arg | Cys | Trp 950 | His | Leu | Leu | Val | Arg 955 | His | Leu | Asn | Asp | Glu 960 |
| Glu | Leu | Ser | Thr | Val 965 | Ile | Asp | Ser | Leu | Ile 970 | Ala | Phe | Ile | Leu | Gln 975 | Lys |
| Trp | Ser | Glu | Phe 980 | Asn | Gly | Lys | Leu | Arg 985 | Asn | Ile | Val | Tyr | Ser 990 | Ile | Leu |
| Asp | Thr | Leu 995 | Ile | Lys | Glu | Lys | Ser 1000 | Asp | Leu | Ile | Leu | Lys 1005 | Leu | Lys | Pro |
| Tyr | Thr | Thr 1010 | Leu | Ala | Leu | Val 1015 | Gly | Lys | Pro | Glu | Leu 1020 | Gly | Ile | Leu |

( 2 ) INFORMATION FOR SEQ ID NO:5:

( i ) SEQUENCE CHARACTERISTICS:
( A ) LENGTH: 1019 base pairs
( B ) TYPE: nucleic acid
( C ) STRANDEDNESS: single
( D ) TOPOLOGY: linear ( i i ) MOLECULE TYPE: cDNA to mRNA
( A ) DESCRIPTION: yeast MEC2 cDNA ( i i i ) HYPOTHETICAL: NO ( i v ) ANTI-SENSE: NO ( v i ) ORIGINAL SOURCE:
( A ) ORGANISM: Saccharomyces cerevisiae ( x i ) SEQUENCE DESCRIPTION: SEQ ID NO:5:

```
AGAAAAGATA GTGTTACACA ACATCAACTA AAAATGGAAA ATATTACACA ACCCACACAG        60
CAATCCACGC AGGCTACTCA AAGGTTTTTG ATTGAGAAGT TTCTCAAGA ACAGATCGGC       120
GAAAACATTG TGTGCAGGGT CATTTGTACC ACGGGTCAAA TTCCCATCCG AGATTTGTCA      180
GCTGATATTT CACAAGTGCT TAAGGAAAAA CGATCCATAA AGAAAGTTTG GACATTTGGT      240
```

-continued

```
AGAAACCCAG CCTGTGACTA TCATTTAGGA AACATTTCAA GACTGTCAAA TAAGCATTTC        300
CAAATACTAC TAGGAGAAGA CGGTAACCTT TTATTGAATG ACATTTCCAC TAATGGGACC        360
TGGTTAAATG GGCAAAAAGT CGAGAAGAAC AGCAATCAGT TACTGTCTCA AGGTGATGAA        420
ATAACCGTTG GTGTAGGCGT GGAATCAGAT ATTTTATCTC TGGTCATTTT CATAAACGAC        480
AAATTTAAGC AGTGCCTCGA GCAGAACAAA GTTGATCGCA TAAGATCTAA CCTGAAAAAT        540
ACCTCTAAAA TAGCTTCTCC TGGTCTTACA TCATCTACTG CATCATCAAT GGTGGCCAAC        600
AAGACTGGTA TTTTAAGGA TTTTCGATT ATTGACGAAG TGGTGGGCCA GGGTGCATTT          660
GCCACAGTAA AGAAAGCCAT TGAAAGAACT ACTGGGAAAA CATTCGCGGT GAAGATTATA        720
AGTAAACGCA AAGTAATAGG CAATATGGAT GGTGTGACAA GAGAGTTAGA AGTATTGCAA        780
AAGCTCAATC ATCCAAGGAT AGTACGATTG AAAGGATTTT ATGAAGATAC TGAGAGTTAT        840
TATATGGTGA TGGAGTTCGT TTCTGGTGGT GACTTAATGG ATTTTGTTGC TGCTCATGGT        900
GCGGTTGGAG AAGATGCTGG GAGGGAGATA TCCAGGCAGA TACTCACAGC AATAAAATAC        960
ATTCACTCTA TGGGCATCAG CCATCGTGAC CTAAAGCCCG ATAATATTCT TATTGAACA       1019
```

( 2 ) INFORMATION FOR SEQ ID NO:6:

( i ) SEQUENCE CHARACTERISTICS:
        ( A ) LENGTH: 821 amino acids
        ( B ) TYPE: amino acid
        ( C ) STRANDEDNESS: single
        ( D ) TOPOLOGY: linear ( i i ) MOLECULE TYPE: protein
        ( A ) DESCRIPTION: yeast MEC2 protein ( x i ) SEQUENCE DESCRIPTION: SEQ ID NO:6:

```
Met Glu Asn Ile Thr Gln Pro Thr Gln Gln Ser Thr Gln Ala Thr Gln
 1               5                  10                  15

Arg Phe Leu Ile Glu Lys Phe Ser Gln Glu Gln Ile Gly Glu Asn Ile
             20                  25                  30

Val Cys Arg Val Ile Cys Thr Thr Gly Gln Ile Pro Ile Arg Asp Leu
         35                  40                  45

Ser Ala Asp Ile Ser Gln Val Leu Lys Glu Lys Arg Ser Ile Lys Lys
     50                  55                  60

Val Trp Thr Phe Gly Arg Asn Pro Ala Cys Asp Tyr His Leu Gly Asn
 65                  70                  75                  80

Ile Ser Arg Leu Ser Asn Lys His Phe Gln Ile Leu Leu Gly Glu Asp
                 85                  90                  95

Gly Asn Leu Leu Leu Asn Asp Ile Ser Thr Asn Gly Thr Trp Leu Asn
             100                 105                 110

Gly Gln Lys Val Glu Lys Asn Ser Asn Gln Leu Leu Ser Gln Gly Asp
         115                 120                 125

Glu Ile Thr Val Gly Val Gly Val Glu Ser Asp Ile Leu Ser Leu Val
     130                 135                 140

Ile Phe Ile Asn Asp Lys Phe Lys Gln Cys Leu Glu Gln Asn Lys Val
 145                 150                 155                 160

Asp Arg Ile Arg Ser Asn Leu Lys Asn Thr Ser Lys Ile Ala Ser Pro
                 165                 170                 175

Gly Leu Thr Ser Ser Thr Ala Ser Ser Met Val Ala Asn Lys Thr Gly
             180                 185                 190

Ile Phe Lys Asp Phe Ser Ile Ile Asp Glu Val Val Gly Gln Gly Ala
         195                 200                 205
```

| | | | | | | | | | | | | | | |
|---|---|---|---|---|---|---|---|---|---|---|---|---|---|---|
| Phe | Ala | Thr | Val | Lys | Lys | Ala | Ile | Glu | Arg | Thr | Thr | Gly | Lys | Thr | Phe |
| | 210 | | | | 215 | | | | | 220 | | | | | |
| Ala | Val | Lys | Ile | Ile | Ser | Lys | Arg | Lys | Val | Ile | Gly | Asn | Met | Asp | Gly |
| 225 | | | | | 230 | | | | | 235 | | | | | 240 |
| Val | Thr | Arg | Glu | Leu | Glu | Val | Leu | Gln | Lys | Leu | Asn | His | Pro | Arg | Ile |
| | | | | 245 | | | | | 250 | | | | | 255 | |
| Val | Arg | Leu | Lys | Gly | Phe | Tyr | Glu | Asp | Thr | Glu | Ser | Tyr | Tyr | Met | Val |
| | | | 260 | | | | | 265 | | | | | 270 | | |
| Met | Glu | Phe | Val | Ser | Gly | Gly | Asp | Leu | Met | Asp | Phe | Val | Ala | Ala | His |
| | | 275 | | | | | 280 | | | | | 285 | | | |
| Gly | Ala | Val | Gly | Glu | Asp | Ala | Gly | Arg | Glu | Ile | Ser | Arg | Gln | Ile | Leu |
| | 290 | | | | | 295 | | | | | 300 | | | | |
| Thr | Ala | Ile | Lys | Tyr | Ile | His | Ser | Met | Gly | Ile | Ser | His | Arg | Asp | Leu |
| 305 | | | | | 310 | | | | | 315 | | | | | 320 |
| Lys | Pro | Asp | Asn | Ile | Leu | Ile | Glu | Gln | Asp | Pro | Val | Leu | Val | Lys |
| | | | | 325 | | | | | 330 | | | | | 335 |
| Ile | Thr | Asp | Phe | Gly | Leu | Ala | Lys | Val | Gln | Gly | Asn | Gly | Ser | Phe | Met |
| | | | 340 | | | | | 345 | | | | | 350 | | |
| Lys | Thr | Phe | Cys | Gly | Thr | Leu | Ala | Tyr | Val | Ala | Pro | Glu | Val | Ile | Arg |
| | | 355 | | | | | 360 | | | | | 365 | | | |
| Gly | Lys | Asp | Thr | Ser | Val | Ser | Pro | Asp | Glu | Tyr | Glu | Glu | Arg | Asn | Glu |
| | 370 | | | | | 375 | | | | | 380 | | | | |
| Tyr | Ser | Ser | Leu | Val | Asp | Met | Trp | Ser | Met | Gly | Cys | Leu | Val | Tyr | Val |
| 385 | | | | | 390 | | | | | 395 | | | | | 400 |
| Ile | Leu | Thr | Gly | His | Leu | Pro | Phe | Ser | Gly | Ser | Thr | Gln | Asp | Gln | Leu |
| | | | | 405 | | | | | 410 | | | | | 415 | |
| Tyr | Lys | Gln | Ile | Gly | Arg | Gly | Ser | Tyr | His | Glu | Gly | Pro | Leu | Lys | Asp |
| | | | 420 | | | | | 425 | | | | | 430 | | |
| Phe | Arg | Ile | Ser | Glu | Glu | Ala | Arg | Asp | Phe | Ile | Asp | Ser | Leu | Leu | Gln |
| | | 435 | | | | | 440 | | | | | 445 | | | |
| Val | Asp | Pro | Asn | Asn | Arg | Ser | Thr | Ala | Ala | Lys | Ala | Leu | Asn | His | Pro |
| | 450 | | | | | 455 | | | | | 460 | | | | |
| Trp | Ile | Lys | Met | Ser | Pro | Leu | Gly | Ser | Gln | Ser | Tyr | Gly | Asp | Phe | Ser |
| 465 | | | | | 470 | | | | | 475 | | | | | 480 |
| Gln | Ile | Ser | Leu | Ser | Gln | Ser | Leu | Ser | Gln | Gln | Lys | Leu | Leu | Glu | Asn |
| | | | | 485 | | | | | 490 | | | | | 495 | |
| Met | Asp | Asp | Ala | Gln | Tyr | Glu | Phe | Val | Lys | Ala | Gln | Arg | Lys | Leu | Gln |
| | | | 500 | | | | | 505 | | | | | 510 | | |
| Met | Glu | Gln | Gln | Leu | Gln | Glu | Gln | Asp | Gln | Glu | Asp | Gln | Asp | Gly | Lys |
| | | 515 | | | | | 520 | | | | | 525 | | | |
| Ile | Gln | Gly | Phe | Lys | Ile | Pro | Ala | His | Ala | Pro | Ile | Arg | Tyr | Thr | Gln |
| | 530 | | | | | 535 | | | | | 540 | | | | |
| Pro | Lys | Ser | Ile | Glu | Ala | Glu | Thr | Arg | Glu | Gln | Lys | Leu | Leu | His | Ser |
| 545 | | | | | 550 | | | | | 555 | | | | | 560 |
| Asn | Asn | Thr | Glu | Asn | Val | Lys | Ser | Ser | Lys | Lys | Gly | Asn | Gly | Arg |
| | | | | 565 | | | | | 570 | | | | | 575 |
| Phe | Leu | Thr | Leu | Lys | Pro | Leu | Pro | Asp | Ser | Ile | Ile | Gln | Glu | Ser | Leu |
| | | | 580 | | | | | 585 | | | | | 590 | | |
| Glu | Ile | Gln | Gln | Gly | Val | Asn | Pro | Phe | Phe | Ile | Gly | Arg | Ser | Glu | Asp |
| | | 595 | | | | | 600 | | | | | 605 | | | |
| Cys | Asn | Cys | Lys | Ile | Glu | Asp | Asn | Arg | Leu | Ser | Arg | Val | His | Cys | Phe |
| 610 | | | | | 615 | | | | | 620 | | | | | |
| Ile | Phe | Lys | Lys | Arg | His | Ala | Val | Gly | Lys | Ser | Met | Tyr | Glu | Ser | Pro |
| 625 | | | | | 630 | | | | | 635 | | | | | 640 |

|     |     |     |     |     |     |     |     |     |     |     |     |     |     |     |
| --- | --- | --- | --- | --- | --- | --- | --- | --- | --- | --- | --- | --- | --- | --- |
| Ala | Gln | Gly | Leu | Asp 645 | Asp | Ile | Trp | Tyr | Cys 650 | His | Thr | Gly | Thr | Asn Val 655 |
| Ser | Tyr | Leu | Asn 660 | Asn | Asn | Arg | Met | Ile 665 | Gln | Gly | Thr | Lys | Phe 670 | Leu Leu |
| Gln | Asp | Gly 675 | Asp | Glu | Ile | Lys | Ile 680 | Ile | Trp | Asp | Lys | Asn 685 | Asn | Lys Phe |
| Val | Ile 690 | Gly | Phe | Lys | Val 695 | Glu | Ile | Asn | Asp | Thr 700 | Thr | Gly | Leu | Phe Asn |
| Glu 705 | Gly | Leu | Gly | Met | Leu 710 | Gln | Glu | Gln | Arg | Val 715 | Val | Leu | Lys | Gln Thr 720 |
| Ala | Glu | Glu | Lys | Asp 725 | Leu | Val | Lys | Lys | Leu 730 | Thr | Gln | Met | Met | Ala Ala 735 |
| Gln | Arg | Ala | Asn 740 | Gln | Pro | Ser | Ala | Ser 745 | Ser | Ser | Ser | Met | Ser 750 | Ala Lys |
| Lys | Pro | Pro 755 | Val | Ser | Asp | Thr | Asn 760 | Asn | Asn | Gly | Asn | Asn 765 | Ser | Val Leu |
| Asn | Asp 770 | Leu | Val | Glu | Ser | Pro 775 | Ile | Asn | Ala | Asn | Thr 780 | Gly | Asn | Ile Leu |
| Lys 785 | Arg | Ile | His | Ser | Val 790 | Ser | Leu | Ser | Gln | Ser 795 | Gln | Ile | Asp | Pro Ser 800 |
| Lys | Lys | Val | Lys | Arg 805 | Ala | Lys | Leu | Asp | Gln 810 | Thr | Ser | Lys | Gly | Pro Glu 815 |
| Asn | Leu | Gln | Phe 820 | Ser |     |     |     |     |     |     |     |     |     |     |

( 2 ) INFORMATION FOR SEQ ID NO:7:

( i ) SEQUENCE CHARACTERISTICS:
        ( A ) LENGTH: 1313 base pairs
        ( B ) TYPE: nucleic acid
        ( C ) STRANDEDNESS: single
        ( D ) TOPOLOGY: linear ( i i ) MOLECULE TYPE: cDNA to mRNA
        ( A ) DESCRIPTION: human CDC34 cDNA ( i i i ) HYPOTHETICAL: NO ( i v ) ANTI-SENSE: YES ( v i ) ORIGINAL SOURCE:
        ( A ) ORGANISM: Homo sapiens ( x i ) SEQUENCE DESCRIPTION: SEQ ID NO:7:

```
ATTGGTGAAT CCGTCCACTC AGTGCTGGAC GTGGCTCCAG GACCTGGAGC TGACAGGCAG      60
GACCGGGCCC CTCGGACCGC TACACCTGGG CCTCCCAGGC TGGTAGTGTC AGGAAACGGC     120
CCCCCGNNCA CGTTCCCAGC AGCGCCCCCG TGGCTCCTCC GGGGTGCGGC CAGTCCGGAA     180
GCTGGGGGAC CCCGGTAGAA GTCGGGCTCA GCTCCCTCC CGAGGGGACA GGTGGGCCGG      240
CCGCTCCCAC CCTGGGCCCG TCCACCGAGC CCGAGTGAC GTGAGTGGCG GTGGGGCAGC      300
CCCTCTTCTC TGAAGCACGT GAAACCCAG AACAGACATG GGAGGGAGA AAAAGCCAAA       360
ACGAAACAAC CAGAGGAGAC GGGGACCAGC ACAAAACCTC CGTGAGGTAG TCTGTCGTCT     420
AAGGAGCCAC GGGTCCGGCC CTAGTGAGGT AAACTCGGCA AGTTTATTCT GGTGGTGTCA    480
GGACTCCTCC GTGCCAGAGT CATCCTCATC GTCCCCGAAG CAGCTGTCGG CCTCCTCCTC    540
CACCTCGCCG TCTCGTAGTA GTCGTCGTAG AAGAGGTCTG AGCCCTCGTC GGGCGCCGGC    600
GCCTTGGTCT TCACGCAGTA CTCGGCCAGC GTGGTGGGCA CCTTCACGCC GTCACGCTCC    660
```

5,674,996

37

38

-continued

| GCGTCCACCT | TGGTCCCCAG | GACCTGCTTC | CGGATGATGT | CTGTGTACTC | CCGATCCTTC | 720 |
| CCCTTGCTCT | CTTTCCACTT | CCTGTACATC | ACGGAGGCGT | CCACGTTTGC | GGGCGAGAAG | 780 |
| GTGTTGGGCT | CGTTCAGGAG | GGAGATCACA | CTCAGGAGAA | TGGTCCTGAC | GTTCTGCGTG | 840 |
| GGGTTCCACC | TCTCTGAGGG | CAGCTCCCCG | CTCTGGGGGT | CGTCCACCGG | CGGGTGGAGG | 900 |
| ATGGAGATAC | ACACGTCCCC | CGTCTCGTAG | ATGTTAGGGT | GCCACATCTT | GGTCAGGAAC | 960 |
| CGAAAGGCTG | GTGGAGAGTA | TGGGTAGTCG | ATGGGGAACT | TGAGGCGCGC | CTTGAAGTAG | 1020 |
| CCGCCCTCGT | AGTAGGTGTT | GGGGGGCCCG | AAAATGGCCA | CCTCCCAGTT | GTATAGATCG | 1080 |
| CCCTCGTCCA | CCAGTGTCAC | GCGGAATCCC | TCGACCGGCT | CTTCCTGCAG | CCCCTTGAGC | 1140 |
| TCCAGCAGCA | GCGCCTTCTG | CGAGCTGGGC | ACTAGCGGCC | GAGCCATGGC | GGCGGCGGAG | 1200 |
| GGGCCCGGGG | TCGGAGCAGC | GCGNGGCCGC | GCGACCACCG | CGAGTTCGCG | AGACGGGCCG | 1260 |
| GGCCGCGCAC | CGTCCGGGGG | GGAGCCACCG | GGGCCGCCGC | CTGCCTCCTC | CTC | 1313 |

( 2 ) INFORMATION FOR SEQ ID NO:8:

( i ) SEQUENCE CHARACTERISTICS:
        ( A ) LENGTH: 1896 base pairs
        ( B ) TYPE: nucleic acid
        ( C ) STRANDEDNESS: single
        ( D ) TOPOLOGY: linear ( i i ) MOLECULE TYPE: cDNA to mRNA
        ( A ) DESCRIPTION: human RAD9compA cDNA ( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:8:

| ATTGTTCTAT | TGATGGCAGG | TAATCATCAC | TCTTCACTAG | CTGAGCATTC | GGTCCACTAA | 60 |
| CCTGAGTCAT | ATCCGGCACT | GGTTTCTCTA | GAAAGGGNTC | CGACGGGGAA | TGCTGATGCA | 120 |
| CAGGCACTTT | CTGCGGGGTG | TTCTGGGGTG | ATGGGTGGAG | CTGTGCCCAA | GGCTGGTGAT | 180 |
| GAGGGTGTGG | AGGTGAAGAC | TGGTGGTGCA | AGCCCGGGTG | AGGCTGCAGT | GGAGGACAGG | 240 |
| TTGGAACTGC | TGAAAAGATG | GCTGTTGACC | AGGATGTTGT | TGGCCAGGTA | TCAGTCGTTC | 300 |
| CTGGATTGCT | TGTGGGTCTC | CAAGGCCAAC | ACCAGGACAA | CCATTTGGCC | TCATGTGCCC | 360 |
| AGTCAATTCC | CTTGGTGCCG | AGGACATGCC | TATAAATGGA | CGAGACTGCT | GCATGTTTCT | 420 |
| GGGGCCCATA | TTCCTCTGTC | CGATTCCCAT | GGCACCAGGG | GGCTGGTGAG | ATGGCTGAGG | 480 |
| ATGGGGCATA | TTTGGATAAC | TGCCAACTTC | CATTGGTATC | CCAGCACTTC | CCGGCCTGAC | 540 |
| TTGTGGAGGA | GGAGTGCCTG | CTGGATTACT | CATTGCTTTC | ATGGGTGACA | TGGGAGGTGG | 600 |
| AGAGGCATAA | GTTCCCTGAG | GCTGTGAAGG | ATGCATAGTT | TGTGTGTTCA | TTTGGTTAAG | 660 |
| TGAGCCACTG | GGGTGGATGG | GCTGCTGGTG | CATTAGTCCT | TGACCACTGT | TTGATGGGAA | 720 |
| TCCTACAGCA | TTGGGGTATC | TTGGTACGGA | CTGATTCATT | GGAGTATTAT | TTGTAAGGCC | 780 |
| TAAATTTGA | TTCATCCCTG | TATTGTTAAC | TAATCCCTGA | TTTAGGTTAC | TGTAAGGATA | 840 |
| TCGAGAATAC | TGCCCTGAGT | TGTTTATAGT | AGGAGAGGGG | ACTGTCTGGC | TCCGAGAACT | 900 |
| AAAGTTAAGG | GTTTGCGGCC | TAACAGCCCC | TTGTTGGGGA | GGATTCGGGG | AGAATCTGGG | 960 |
| ACTGTGGGCA | ACGGATTCTC | CATGGAGAGC | AGTAGAGGGG | TGGTGATGGA | ACTGCTGCAC | 1020 |
| CGAGTGACGC | AAGGAAGGTG | CCATGCTGGG | ACTCTGCTGG | GGCACGTGGG | ACAAGTGGCC | 1080 |
| AGGTCCTGAG | GTGGCAATAA | AAGGATTTCC | CTGATTGAGG | CCCTCTTGGC | CTTGGGAAAA | 1140 |

-continued

```
CTGGCTCATC CTCTGCTGTG GCTGACCATG CTGCTGCATG GAAAAATCCC CACGTGCCAT      1200
ATAGCTGCCC ATCTGCTGCA TGTGCTGAGG GTGGCCCTGT GCAGGGGGCC CCGACGGAGC      1260
CGGCTGCGGT GGCTGCGGCT GTGGCTGCTG CTGCTGGTAG GGGGCTCGTA TCTGGTCTGG      1320
TACCTGAACA GCCCTGGGGC CCCACATGGA GCTGCTGTCC ACAAGGATT GCCCATGCCT       1380
CTCATTCTGC ATGCCAGGGT AGACACCCAT CTGACCGCCA CCACTGCCAC CATGGGGCAC      1440
CTGAGGAACG GGAGGGGTGT GATACTGCGA GTGCGGAGAC GCGAGTCCGT TCCCAGGGGT      1500
GTTGCTCATC ATTCTGTTCG GCTGATCCAT CAGATGCATC TTTTGTTGTT CATACTGATT      1560
ATAGTGATCA AAATGTGTCA GCTTGTTTG  ATTTTGATTA GTTGAAGGAT GATGAAGGGA      1620
TGGCTGTAAA GAGGCAAAGC CTTGGTCTAT TGGCATTTGC TGACCCATAG GATTTACTGG      1680
ATTTTCCGGG TAACCACATT CTCCGAGGCC TTCAAGACCT TCACTGAAAA TATTCCCATC      1740
CTCGCCAAAA AGACTCATCA TTCCTGGATC TGCCATCTTA TTCCAACACA CGGCTCCTCC      1800
AAACCACAGC TCAGGAGCTT GCCTGTGCTT CACTTCACTG AGGTGTTTGC CCTCAAAGCC      1860
TATATGACCA ATCCCTAATT GCTGTCCTGA TGATGA                                1896
```

(2) INFORMATION FOR SEQ ID NO:9:

(i) SEQUENCE CHARACTERISTICS:
       (A) LENGTH: 1647 base pairs
       (B) TYPE: nucleic acid
       (C) STRANDEDNESS: single
       (D) TOPOLOGY: linear (ii) MOLECULE TYPE: cDNA to mRNA
       (A) DESCRIPTION: human RAD9compB cDNA (iii) HYPOTHETICAL: NO (iv) ANTI-SENSE: NO (vi) ORIGINAL SOURCE:
       (A) ORGANISM: Homo sapiens (xi) SEQUENCE DESCRIPTION: SEQ ID NO:9:

```
ATTGCAGGTT CCGTAGCTTT CTAGTTTTTT TTTTTTTTC  ACTTGGATCA AATAGTTTTG       60
ATAGACAGAA AAAGATCTGT ACCATTATTT CCTTTCCTTA ACAGCTATTG TAATTTCCTG      120
GACTTGGTTG CTTTTCACTT GGGCAGTTAA GAAGACACAG CTTGTTTTCC CCATCAGTTT      180
TCTCTCTCTC TCCTTCGTGT GTGTGTGTGT GTGTGTGTGT GTGTGTGTGT GTGTGTGCGT      240
GCGTGCACAG GGCCAATCTT CAGGCTTATG GCTTTTGGAA CATTTTCTTA ATTTAATAGA      300
GAACAGAATT CAATGATTAG CAACATCACT AAAAATTTAC CCCATTTCTT CTCCATGAGT      360
CACTGACACC CGATGCGCAT GAACAGTCCA ACGTCCACCT CGTAAGATGT CATCGGGGTT      420
CAGGGTTCAG AAGCATCGAG GACTGGTGGC CGGCCCTCTG TGCTCGCCGT GTGACAATTC      480
CAGTGGCTTT CCTGGCACCA TCAGATGCCT GGTGCCACAA GCTTGGGTCT GCTCCTAGGG      540
GGACGAGGGG TTCCTCCTCC TCCTCAATTG CTTTATGTGC CTTCACTCAG TGAACCCCAA      600
TGGGATGGAC AACCTGACTT TTTAAACCTA AGGGTTGGGC CTGAACGATG ATTACTTTGC      660
CCACGTGCCT TCTAGGTGCC GAATGTGTGT TCCTGTGATA TTGACGTTGA CATCCCTGCG      720
GATTCAGCCA CAGGTTTCTG ACAAGCTGGA GGAAGCAATG GTAATTTTGG CTTTTTCGGT      780
TTTGTCTTCA GATAATGAAA AGCTTTTGTA AACAGCTGA  GTGTCAATAT GAGTTCTATG      840
GCTTCAATCT CCTTTAAAAA TAAAATTCTT AAGGGTCCAA AACAAAGAAG AGGGGGCAAA      900
TTAAAACCCA ATAAAAGGAA AAGAAAAGAA AGAAAACCAA ACCCCAAACA AGAAAAAAGA      960
```

-continued

| | | | | | |
|---|---|---|---|---|---|
| AAAAAAATTG | CTGATATTGC | CACAAATCAT | TAGAAATCTC | CTGACATGCT | GAAACCAAAT | 1020 |
| GGTCGTAAGT | TCAAAACAAA | TCAGTGACTT | GTTTTTAATT | TTTTGTGGTT | TCCTTTTGCT | 1080 |
| CTTTCTGCCC | CTTTGCCGTC | CGATTGGTGA | TGTTATTCAA | ACAGGACCGG | ATCCCTGCTA | 1140 |
| AGTGCAGGAG | GGACCCTGCC | GCTTCTTTCA | TCTCCTCATC | ATCGCTCTCG | GGGGCTTTT | 1200 |
| CGGTGCGTCT | CTTTTTGAGG | GGCAGTGTGT | CGCTGGGGAC | CTTCCTGGCC | TTGGCGAAGT | 1260 |
| GCTGGCGCTT | CTTGTGCTGG | GATGCGTACC | CGCTGTCCCC | CAGAGAATCC | TTGGGCTCCT | 1320 |
| TCTGGCTGTG | CTTCCTGTCG | TCCTCTTCCG | TGTCGCTGGG | GCTCTCGTGG | CTCCGGAAGC | 1380 |
| TCCCCTCGCT | GCCCTCGCTG | CCCTCCTGGC | TCCCCTTGGT | GGCAAACTCA | TAGTGGTCGT | 1440 |
| CGGCTGAGGA | GGAGGAGGAG | GAGATGGAGT | CGCTGGTGGG | CGAGGTGCTC | CGGGCGTTGG | 1500 |
| AGGACTTGGC | ACTGCTGTAG | TTGTGATCCT | CCTTGGGGTC | TCCGCTGACC | ACTGGGGAGC | 1560 |
| CACAAGATGG | CTCACTCTCA | GTCCGCATCC | GGCAGCTGGT | GATGCCATTC | CTCATGGCCG | 1620 |
| CTGTCACCCC | AATGGGAGTG | ATTGGCA | | | | 1647 |

(2) INFORMATION FOR SEQ ID NO:10:

(i) SEQUENCE CHARACTERISTICS:
        (A) LENGTH: 2150 base pairs
        (B) TYPE: nucleic acid
        (C) STRANDEDNESS: single
        (D) TOPOLOGY: linear (ii) MOLECULE TYPE: cDNA to mRNA
        (A) DESCRIPTION: yeast RAD17 cDNA (iii) HYPOTHETICAL: NO (iv) ANTI-SENSE: NO (vi) ORIGINAL SOURCE:
        (A) ORGANISM: Saccharomyces cerevisiae (ix) FEATURE:
        (A) NAME/KEY: CDS
        (B) LOCATION: 741..1947

(xi) SEQUENCE DESCRIPTION: SEQ ID NO:10:

| | | | | | |
|---|---|---|---|---|---|
| AGCAGGAATT | GGTAACGCCA | GGTTTTCCCG | ATCAGACGTT | GTAAACAGG | CCAGTGAATT | 60 |
| GTAATACGAC | TCACTATAGG | GCGAATTGGG | TACCGGGCCC | CCCCTCGAGG | TCGACGGTAT | 120 |
| CGATAAGCTT | GATATCGAAT | TCCTGCAGCC | CCTAAAATGC | CATTTGTTCA | AATGGATCAA | 180 |
| ATTTCCCAAT | TTTTATCATT | TTCGAGAAAA | TATGGTGTGC | CTGAAGATGA | ACTGTTTCAG | 240 |
| ACAATTGATC | TTTTTGAGAA | AAAGGATCCT | GCCATTGTTT | TCCAAACGTT | GAAGTCACTA | 300 |
| TCTCGTTACG | CCAACAAAAA | ACATACAGAT | AGATTTCCAG | TTCTAGGACC | ACAACTGTCA | 360 |
| ACAAAGAAGC | CAAGACCCCC | GGTTAAGTCT | AAACCAAAAC | ATCTACAAGA | TGGTACTGGA | 420 |
| TGGAGCACTT | TTGAATACGG | TTATATGAAA | GGTGCATCTC | AGGCTACTGA | AGGAGTGGTG | 480 |
| TTAGGACAAC | GGAGAGATAT | AGTTTAGAGA | ATTATTATTA | ACACTTTCTC | TGGCAGAAAT | 540 |
| TGATAAATAA | ACATTTAAGA | ACCCTATATA | CGCAACCAAA | GTTCCTTTGA | TATATTTTAG | 600 |
| TTTTCCATCA | AAGTTTTCCT | ACATAAACAC | TAAGGTGGCT | AGAGACGCGT | AACAAAAGTT | 660 |
| AACGTTACCG | GTAAAAATGT | GATTATACAA | ATCAATCTCA | CAGAACGGTG | TGGAAACAAA | 720 |

| | | | | | | | |
|---|---|---|---|---|---|---|---|
| GTAGTTGAAG GATTTCAACT | ATG | CGA ATC AAC AGT GAG CTA GCG AAC AAG | | | | | 770 |
| | Met | Arg Ile Asn Ser Glu Leu Ala Asn Lys | | | | | |
| | 1 | 5                     10 | | | | | |

| | | | | | | | | | | |
|---|---|---|---|---|---|---|---|---|---|---|
| TTT | TCT | GCC | TCA | ACG | GTG | CAC | TTA | GAA | CAT | ATC | ACA | ACT | GCT | TTA | AGT | 818 |
| Phe | Ser | Ala | Ser | Thr | Val | His | Leu | Glu | His | Ile | Thr | Thr | Ala | Leu | Ser |
| | | 15 | | | | 20 | | | | 25 | | | | | |

| | | | | | | | | | | | | | | | | |
|---|---|---|---|---|---|---|---|---|---|---|---|---|---|---|---|---|
| TGT | TTA | ACA | CCT | TTT | GGT | TCT | AAA | GAC | GAT | GTG | CTT | ATA | TTC | ATT | GAT | 866 |
| Cys | Leu | Thr | Pro 30 | Phe | Gly | Ser | Lys | Asp 35 | Asp | Val | Leu | Ile | Phe 40 | Ile | Asp | |
| GCT | GAT | GGG | CTG | TCA | TTT | GTC | AGG | GAG | AAT | AAT | CAT | GTG | ATA | AAA | ATC | 914 |
| Ala | Asp | Gly 45 | Leu | Ser | Phe | Val | Arg 50 | Glu | Asn | Asn | His | Val 55 | Ile | Lys | Ile | |
| CAA | CTA | CTG | TTA | TCT | CGG | GAG | CTA | TTT | ATG | TCT | TAT | TCG | TAT | AGA | AAT | 962 |
| Gln | Leu 60 | Leu | Leu | Ser | Arg | Glu 65 | Leu | Phe | Met | Ser | Tyr 70 | Ser | Tyr | Arg | Asn | |
| GAA | ACT | GAG | GAT | CAC | ATG | AAA | CTT | TGT | GTA | AAA | ATA | AAT | CAT | ATC | TTA | 1010 |
| Glu 75 | Thr | Glu | Asp | His | Met 80 | Lys | Leu | Cys | Val | Lys 85 | Ile | Asn | His | Ile | Leu 90 | |
| GAT | AGC | GTT | AGC | GTG | ATG | AAC | AGG | AAT | TCG | GAT | GAC | ATT | GTT | GAG | TGT | 1058 |
| Asp | Ser | Val | Ser 95 | Val | Met | Asn | Arg | Asn | Ser 100 | Asp | Asp | Ile | Val | Glu 105 | Cys | |
| ACT | TTA | TCT | TAT | GAT | GGA | CAT | GGA | TCA | CCA | TTT | GTA | CTA | ATA | TTT | GAA | 1106 |
| Thr | Leu | Ser | Tyr 110 | Asp | Gly | His | Gly | Ser 115 | Pro | Phe | Val | Leu | Ile 120 | Phe | Glu | |
| GAC | TCG | TTC | ATT | TCT | GAG | AGA | GTG | GAG | TAC | TCT | ACC | TAC | TTA | ATT | AAG | 1154 |
| Asp | Ser | Phe 125 | Ile | Ser | Glu | Arg | Val 130 | Glu | Tyr | Ser | Thr | Tyr 135 | Leu | Ile | Lys | |
| GAT | TTT | GAT | ACT | AAT | GGA | CTA | GAA | CTC | GAT | AGA | GAA | AGG | ATA | AGC | TTT | 1202 |
| Asp | Phe 140 | Asp | Thr | Asn | Gly | Leu 145 | Glu | Leu | Asp | Arg | Glu 150 | Arg | Ile | Ser | Phe | |
| GAG | GCA | ATT | ATT | AAG | GGC | GAA | GCC | CTT | CAT | TCA | GCC | TTA | AAG | GAT | CTA | 1250 |
| Glu 155 | Ala | Ile | Ile | Lys | Gly 160 | Glu | Ala | Leu | His | Ser 165 | Ala | Leu | Lys | Asp | Leu 170 | |
| AAA | GAA | ATC | GGA | TGC | AAA | GAG | TGC | TAT | GTA | TAT | GCA | AAG | ACC | GAG | GCG | 1298 |
| Lys | Glu | Ile | Gly | Cys 175 | Lys | Glu | Cys | Tyr | Val 180 | Tyr | Ala | Lys | Thr | Glu 185 | Ala | |
| AAT | GAT | GAG | AAT | GTA | TTT | GCC | CTG | ATA | TCT | AAA | TCT | CAG | CTA | GGA | TTT | 1346 |
| Asn | Asp | Glu | Asn 190 | Val | Phe | Ala | Leu | Ile 195 | Ser | Lys | Ser | Gln | Leu 200 | Gly | Phe | |
| TCT | AAA | ATA | AAA | TTA | CCC | AGT | AAC | AGA | TCC | ATA | CTA | GAG | AAG | TTA | CAA | 1394 |
| Ser | Lys | Ile 205 | Lys | Leu | Pro | Ser | Asn 210 | Arg | Ser | Ile | Leu | Glu 215 | Lys | Leu | Gln | |
| GTA | TTT | GAC | GGA | GAT | TCC | ACA | ACA | GTA | ATA | GAT | GGT | TTT | GCT | GTA | ATT | 1442 |
| Val | Phe 220 | Asp | Gly | Asp | Ser | Thr 225 | Thr | Val | Ile | Asp | Gly 230 | Phe | Ala | Val | Ile | |
| GGG | TTC | TTC | GAT | TTC | ACC | TCG | TTT | GAT | AAA | ATC | AGA | AAG | AGT | ACT | AAA | 1490 |
| Gly 235 | Phe | Phe | Asp | Phe | Thr 240 | Ser | Phe | Asp | Lys | Ile 245 | Arg | Lys | Ser | Thr | Lys 250 | |
| ATT | GCA | AGC | AAA | GTC | CTT | TTC | AGG | ATG | GAT | GTT | CAT | GGC | GTA | TTG | AGT | 1538 |
| Ile | Ala | Ser | Lys | Val 255 | Leu | Phe | Arg | Met | Asp 260 | Val | His | Gly | Val | Leu 265 | Ser | |
| GTA | AAT | ATT | CTA | AGT | CAA | ACA | GAC | GAT | GTC | ATT | ATC | ACT | GAT | ACT | ACA | 1586 |
| Val | Asn | Ile | Leu 270 | Ser | Gln | Thr | Asp | Asp 275 | Val | Ile | Ile | Thr | Asp 280 | Thr | Thr | |
| AGA | CCT | TCA | AAT | AAT | CGA | CCA | GGT | AGT | ATT | CGC | CAA | CTG | CAG | CTA | CCC | 1634 |
| Arg | Pro | Ser 285 | Asn | Asn | Arg | Pro | Gly 290 | Ser | Ile | Arg | Gln | Leu 295 | Gln | Leu | Pro | |
| AAG | GAT | TAT | CCC | GGT | ATA | GTA | ATT | GAG | GTT | TGC | ATG | CTA | GAA | AAA | GAA | 1682 |
| Lys | Asp | Tyr 300 | Pro | Gly | Ile | Val | Ile 305 | Glu | Val | Cys | Met | Leu 310 | Glu | Lys | Glu | |
| TCC | ATA | GAT | GAG | GCA | GCA | CAG | ACA | GAA | ATA | GAA | CTC | CTG | ATG | GAG | ACT | 1730 |
| Ser | Ile | Asp | Glu | Ala 315 | Ala | Gln | Thr 320 | Glu | Ile | Glu | Leu | Leu 325 | Met | Glu | Thr 330 | |
| AAT | GAA | CTT | GGC | AAT | CGT | AAT | AGT | TTT | AAA | AAA | TCA | ACT | ATA | AGA | AAA | 1778 |
| Asn | Glu | Leu | Gly | Asn 335 | Arg | Asn | Ser | Phe | Lys 340 | Lys | Ser | Thr | Ile | Arg 345 | Lys | |

```
AGA TAT GGT ACA GAT AAA GGC AAT GAA ACT TCA AAT GAC AAC TTG CTG      1826
Arg Tyr Gly Thr Asp Lys Gly Asn Glu Thr Ser Asn Asp Asn Leu Leu
            350                 355                 360

CAA TTG AAT GGG AAA AAA ATT AAA CTA CCA TCT GAA GAA GAA AAC AAT      1874
Gln Leu Asn Gly Lys Lys Ile Lys Leu Pro Ser Glu Glu Glu Asn Asn
        365                 370                 375

AAA AAC AGG GAA AGT GAG GAT GAA GAG AAT CAC TGC AAG TAT CCA ACA      1922
Lys Asn Arg Glu Ser Glu Asp Glu Glu Asn His Cys Lys Tyr Pro Thr
    380                 385                 390

AAG GAT ATT CCT ATA TTT TTT TAA G TCAATATCCA GCATCGCAGA              1967
Lys Asp Ile Pro Ile Phe Phe  *
395                 400

AAACGCAGAA CTTCATTCAG CATTTGGTAA TTTTATAACA TATAACTTAC AATTAAATAA    2027

AAGTTTAACT ATATATTATT ATGTGATCTA ACTCTAGAAA AAGTACTAAT GAACATCACA    2087

CCGTTTATTG TTGGGAGAAG TGTTCCATGG GGGATCCACT AGTTCTAGAG CGGCGCCACC    2147

GCG                                                                  2150
```

( 2 ) INFORMATION FOR SEQ ID NO:11:

( i ) SEQUENCE CHARACTERISTICS:
        ( A ) LENGTH: 401 amino acids
        ( B ) TYPE: amino acid
        ( D ) TOPOLOGY: linear ( i i ) MOLECULE TYPE: protein
        ( A ) DESCRIPTION: yeast RAD17 protein ( x i ) SEQUENCE DESCRIPTION: SEQ ID NO:11:

```
Met Arg Ile Asn Ser Glu Leu Ala Asn Lys Phe Ser Ala Ser Thr Val
 1               5                  10                  15

His Leu Glu His Ile Thr Thr Ala Leu Ser Cys Leu Thr Pro Phe Gly
            20                  25                  30

Ser Lys Asp Asp Val Leu Ile Phe Ile Asp Ala Asp Gly Leu Ser Phe
        35                  40                  45

Val Arg Glu Asn Asn His Val Ile Lys Ile Gln Leu Leu Ser Arg
    50                  55                  60

Glu Leu Phe Met Ser Tyr Ser Tyr Arg Asn Glu Thr Glu Asp His Met
65                  70                  75                  80

Lys Leu Cys Val Lys Ile Asn His Ile Leu Asp Ser Val Ser Val Met
                85                  90                  95

Asn Arg Asn Ser Asp Asp Ile Val Glu Cys Thr Leu Ser Tyr Asp Gly
            100                 105                 110

His Gly Ser Pro Phe Val Leu Ile Phe Glu Asp Ser Phe Ile Ser Glu
        115                 120                 125

Arg Val Glu Tyr Ser Thr Tyr Leu Ile Lys Asp Phe Asp Thr Asn Gly
    130                 135                 140

Leu Glu Leu Asp Arg Glu Arg Ile Ser Phe Glu Ala Ile Ile Lys Gly
145                 150                 155                 160

Glu Ala Leu His Ser Ala Leu Lys Asp Leu Lys Glu Ile Gly Cys Lys
                165                 170                 175

Glu Cys Tyr Val Tyr Ala Lys Thr Glu Ala Asn Asp Glu Asn Val Phe
            180                 185                 190

Ala Leu Ile Ser Lys Ser Gln Leu Gly Phe Ser Lys Ile Lys Leu Pro
        195                 200                 205

Ser Asn Arg Ser Ile Leu Glu Lys Leu Gln Val Phe Asp Gly Asp Ser
    210                 215                 220
```

| | | | | | | | | | | | | | | |
|---|---|---|---|---|---|---|---|---|---|---|---|---|---|---|
| Thr | Thr | Val | Ile | Asp | Gly | Phe | Ala | Val | Ile | Gly | Phe | Phe | Asp | Phe | Thr |
| 225 | | | | | 230 | | | | | 235 | | | | | 240 |
| Ser | Phe | Asp | Lys | Ile | Arg | Lys | Ser | Thr | Lys | Ile | Ala | Ser | Lys | Val | Leu |
| | | | | 245 | | | | | 250 | | | | | 255 | |
| Phe | Arg | Met | Asp | Val | His | Gly | Val | Leu | Ser | Val | Asn | Ile | Leu | Ser | Gln |
| | | | 260 | | | | | 265 | | | | | 270 | | |
| Thr | Asp | Asp | Val | Ile | Ile | Thr | Asp | Thr | Thr | Arg | Pro | Ser | Asn | Asn | Arg |
| | | 275 | | | | | 280 | | | | | 285 | | | |
| Pro | Gly | Ser | Ile | Arg | Gln | Leu | Gln | Leu | Pro | Lys | Asp | Tyr | Pro | Gly | Ile |
| | 290 | | | | 295 | | | | | 300 | | | | | |
| Val | Ile | Glu | Val | Cys | Met | Leu | Glu | Lys | Glu | Ser | Ile | Asp | Glu | Ala | Ala |
| 305 | | | | | 310 | | | | | 315 | | | | | 320 |
| Gln | Thr | Glu | Ile | Glu | Leu | Leu | Met | Glu | Thr | Asn | Glu | Leu | Gly | Asn | Arg |
| | | | | 325 | | | | | 330 | | | | | 335 | |
| Asn | Ser | Phe | Lys | Lys | Ser | Thr | Ile | Arg | Lys | Arg | Tyr | Gly | Thr | Asp | Lys |
| | | | 340 | | | | | 345 | | | | | 350 | | |
| Gly | Asn | Glu | Thr | Ser | Asn | Asp | Asn | Leu | Leu | Gln | Leu | Asn | Gly | Lys | Lys |
| | | 355 | | | | | 360 | | | | | 365 | | | |
| Ile | Lys | Leu | Pro | Ser | Glu | Glu | Asn | Asn | Lys | Asn | Arg | Glu | Ser | Glu | |
| | 370 | | | | | 375 | | | | | 380 | | | | |
| Asp | Glu | Glu | Asn | His | Cys | Lys | Tyr | Pro | Thr | Lys | Asp | Ile | Pro | Ile | Phe |
| 385 | | | | | 390 | | | | | 395 | | | | | 400 |
| Phe | | | | | | | | | | | | | | | |

( 2 ) INFORMATION FOR SEQ ID NO:12:

( i ) SEQUENCE CHARACTERISTICS:
        ( A ) LENGTH: 2762 base pairs
        ( B ) TYPE: nucleic acid
        ( C ) STRANDEDNESS: single
        ( D ) TOPOLOGY: linear ( i i ) MOLECULE TYPE: cDNA to mRNA
        ( A ) DESCRIPTION: yeast RAD24 cDNA ( i i i ) HYPOTHETICAL: NO ( i v ) ANTI-SENSE: NO ( v i ) ORIGINAL SOURCE:
        ( A ) ORGANISM: Saccharomyces cerevisiae ( i x ) FEATURE:
        ( A ) NAME/KEY: CDS
        ( B ) LOCATION: 3..1982

( x i ) SEQUENCE DESCRIPTION: SEQ ID NO:12:

| | | | | | | | | | | | | | | | |
|---|---|---|---|---|---|---|---|---|---|---|---|---|---|---|---|
| AT | ATG | GAT | AGT | ACG | AAT | TTG | AAC | AAA | CGG | CCC | TTA | TTA | CAA | TAT | AGT | 47 |
| | Met | Asp | Ser | Thr | Asn | Leu | Asn | Lys | Arg | Pro | Leu | Leu | Gln | Tyr | Ser | |
| | 1 | | | | 5 | | | | | 10 | | | | | 15 | |
| CTC | AGT | TCA | TTG | GGC | TCG | CAA | ATA | ACA | AAA | TGG | AGC | TCA | TCT | AGA | CCG | 95 |
| Leu | Ser | Ser | Leu | Gly | Ser | Gln | Ile | Thr | Lys | Trp | Ser | Ser | Ser | Arg | Pro | |
| | | | | 20 | | | | | 25 | | | | | 30 | | |
| ACT | TCG | CCA | GTT | CGT | AAG | GCG | AGA | AGC | ACT | GAA | AAT | GAC | TTT | CTT | TCC | 143 |
| Thr | Ser | Pro | Val | Arg | Lys | Ala | Arg | Ser | Thr | Glu | Asn | Asp | Phe | Leu | Ser | |
| | | | 35 | | | | | 40 | | | | | 45 | | | |
| AAG | CAA | GAT | ACG | TCT | AGT | ATC | CTC | CCA | AGT | ATC | AAC | GAC | GAC | GGC | GGT | 191 |
| Lys | Gln | Asp | Thr | Ser | Ser | Ile | Leu | Pro | Ser | Ile | Asn | Asp | Asp | Gly | Gly | |
| | | | 50 | | | | | 55 | | | | | 60 | | | |
| GAA | CAG | TGG | TAC | GAA | AAG | TTC | AAG | CCC | AAT | TGT | TTG | GAG | CAA | GTG | GCC | 239 |
| Glu | Gln | Trp | Tyr | Glu | Lys | Phe | Lys | Pro | Asn | Cys | Leu | Glu | Gln | Val | Ala | |
| | 65 | | | | 70 | | | | | 75 | | | | | | |

| | | | | | | | | | | | | | | | | |
|---|---|---|---|---|---|---|---|---|---|---|---|---|---|---|---|---|
| ATA | CAT | AAA | AGA | AAA | CTT | AAA | GAT | GTA | CAA | GAA | GCT | TTA | GAT | GCC | ATG | 287 |
| Ile | His | Lys | Arg | Lys | Leu | Lys | Asp | Val | Gln | Glu | Ala | Leu | Asp | Ala | Met | |
| 80 | | | | 85 | | | | | 90 | | | | | | 95 | |
| TTT | TTA | CCT | AAC | GCC | AAG | CAT | AGG | ATC | CTA | CTA | CTG | TCT | GGC | CCC | AGT | 335 |
| Phe | Leu | Pro | Asn | Ala | Lys | His | Arg | Ile | Leu | Leu | Leu | Ser | Gly | Pro | Ser | |
| | | | | 100 | | | | | 105 | | | | | 110 | | |
| GGA | TGC | TCT | AAA | AGT | ACG | GTC | ATA | AAA | GAA | CTC | TCA | AAA | ATC | TTA | GTT | 383 |
| Gly | Cys | Ser | Lys | Ser | Thr | Val | Ile | Lys | Glu | Leu | Ser | Lys | Ile | Leu | Val | |
| | | | | 115 | | | | | 120 | | | | | 125 | | |
| CCT | AAA | TAC | AGA | CAA | AAC | AGC | AAC | GGA | ACG | TCC | TTT | CGA | AGC | ACC | CCG | 431 |
| Pro | Lys | Tyr | Arg | Gln | Asn | Ser | Asn | Gly | Thr | Ser | Phe | Arg | Ser | Thr | Pro | |
| | | | 130 | | | | | 135 | | | | | 140 | | | |
| AAC | GAG | CAT | AAA | GTG | ACC | GAG | TTT | AGA | GGT | GAT | TGT | ATA | GTC | AAC | GAT | 479 |
| Asn | Glu | His | Lys | Val | Thr | Glu | Phe | Arg | Gly | Asp | Cys | Ile | Val | Asn | Asp | |
| 145 | | | | | 150 | | | | | 155 | | | | | | |
| CTT | CCT | CAG | ATG | GAA | AGC | TTT | AGT | GAG | TTC | TTA | AAA | GGC | GCA | CGG | TAT | 527 |
| Leu | Pro | Gln | Met | Glu | Ser | Phe | Ser | Glu | Phe | Leu | Lys | Gly | Ala | Arg | Tyr | |
| 160 | | | | | 165 | | | | | 170 | | | | | 175 | |
| CTT | GTG | ATG | TCC | AAC | CTG | TCA | TTA | ATA | CTT | ATC | GAG | GAC | CTT | CCC | AAC | 575 |
| Leu | Val | Met | Ser | Asn | Leu | Ser | Leu | Ile | Leu | Ile | Glu | Asp | Leu | Pro | Asn | |
| | | | | 180 | | | | | 185 | | | | | 190 | | |
| GTC | TTC | CAT | ATA | GAT | ACC | AGA | CGT | CGA | TTT | CAA | CAA | CTT | ATA | TTA | CAG | 623 |
| Val | Phe | His | Ile | Asp | Thr | Arg | Arg | Arg | Phe | Gln | Gln | Leu | Ile | Leu | Gln | |
| | | | 195 | | | | | 200 | | | | | 205 | | | |
| TGG | CTA | TAT | AGT | TCG | GAG | CCT | CTA | TTA | CCT | CCC | CTT | GTT | ATA | TGT | ATA | 671 |
| Trp | Leu | Tyr | Ser | Ser | Glu | Pro | Leu | Leu | Pro | Pro | Leu | Val | Ile | Cys | Ile | |
| | | 210 | | | | | 215 | | | | | 220 | | | | |
| ACT | GAA | TGT | GAA | ATT | CCA | GAG | AAC | GAT | AAT | AAT | TAT | CGC | AAA | TTT | GGT | 719 |
| Thr | Glu | Cys | Glu | Ile | Pro | Glu | Asn | Asp | Asn | Asn | Tyr | Arg | Lys | Phe | Gly | |
| | 225 | | | | | 230 | | | | | 235 | | | | | |
| ATT | GAT | TAT | ACA | TTT | AGT | GCA | GAA | ACC | ATA | ATG | AAC | AAA | GAA | ATA | TTG | 767 |
| Ile | Asp | Tyr | Thr | Phe | Ser | Ala | Glu | Thr | Ile | Met | Asn | Lys | Glu | Ile | Leu | |
| 240 | | | | | 245 | | | | | 250 | | | | | 255 | |
| ATG | CAT | CCA | AGG | TTG | AAA | AGA | ATT | AAG | TTT | AAT | CCA | ATT | AAC | AGC | ACT | 815 |
| Met | His | Pro | Arg | Leu | Lys | Arg | Ile | Lys | Phe | Asn | Pro | Ile | Asn | Ser | Thr | |
| | | | | 260 | | | | | 265 | | | | | 270 | | |
| TTA | TTA | AAA | AAG | CAC | TTG | AAA | TTT | ATT | TGT | GTA | CAG | AAT | ATG | AAA | ATG | 863 |
| Leu | Leu | Lys | Lys | His | Leu | Lys | Phe | Ile | Cys | Val | Gln | Asn | Met | Lys | Met | |
| | | | 275 | | | | | 280 | | | | | 285 | | | |
| TTG | AAG | GAG | AAA | AAT | AAA | TGG | AAT | AAA | AGA | CAG | GAA | GTC | ATA | GAT | TAT | 911 |
| Leu | Lys | Glu | Lys | Asn | Lys | Trp | Asn | Lys | Arg | Gln | Glu | Val | Ile | Asp | Tyr | |
| | | 290 | | | | | 295 | | | | | 300 | | | | |
| ATT | GCG | CAA | GAG | ACT | GGT | GAT | ATT | AGG | TCG | GCC | ATT | ACG | ACC | CTT | CAA | 959 |
| Ile | Ala | Gln | Glu | Thr | Gly | Asp | Ile | Arg | Ser | Ala | Ile | Thr | Thr | Leu | Gln | |
| | 305 | | | | | 310 | | | | | 315 | | | | | |
| TTT | TGG | GCG | ACA | TCA | AGT | GGA | AGT | TTG | CCG | ATT | TCA | ACC | CGA | GAA | TCC | 1007 |
| Phe | Trp | Ala | Thr | Ser | Ser | Gly | Ser | Leu | Pro | Ile | Ser | Thr | Arg | Glu | Ser | |
| 320 | | | | | 325 | | | | | 330 | | | | | 335 | |
| ACC | ATA | TCA | TAC | TTT | CAT | GCC | ATT | GGG | AAG | GTG | ATA | CAT | GGT | TCC | CAT | 1055 |
| Thr | Ile | Ser | Tyr | Phe | His | Ala | Ile | Gly | Lys | Val | Ile | His | Gly | Ser | His | |
| | | | | 340 | | | | | 345 | | | | | 350 | | |
| AGC | ACG | AAT | AAC | GAT | AAC | GAA | ATG | ATT | AAT | AAC | CTC | TTC | GAA | AAT | TCG | 1103 |
| Ser | Thr | Asn | Asn | Asp | Asn | Glu | Met | Ile | Asn | Asn | Leu | Phe | Glu | Asn | Ser | |
| | | | 355 | | | | | 360 | | | | | 365 | | | |
| AAC | AAT | TTG | TTA | TCG | AAA | GAG | GAT | TTC | AAA | TTA | GGA | ATA | TTA | GAG | AAC | 1151 |
| Asn | Asn | Leu | Leu | Ser | Lys | Glu | Asp | Phe | Lys | Leu | Gly | Ile | Leu | Glu | Asn | |
| | | 370 | | | | | 375 | | | | | 380 | | | | |
| TAT | AAC | ACA | TTT | AAT | AAA | GGC | GAA | TTC | AGC | ATT | TCT | GAT | GCA | TCA | TCA | 1199 |
| Tyr | Asn | Thr | Phe | Asn | Lys | Gly | Glu | Phe | Ser | Ile | Ser | Asp | Ala | Ser | Ser | |
| | 385 | | | | | 390 | | | | | 395 | | | | | |

```
ATT GTG GAT TGC CTG AGC GAG TGT GAT AAT ATG AAT GGT CTA CCA GAA    1247
Ile Val Asp Cys Leu Ser Glu Cys Asp Asn Met Asn Gly Leu Pro Glu
400             405             410             415

TCC AAT GAG TAT GGT TTA CGA GAA GTG CGC AAA ACC TTT CGT AAC ATC    1295
Ser Asn Glu Tyr Gly Leu Arg Glu Val Arg Lys Thr Phe Arg Asn Ile
            420             425             430

AGT AAA CAA GGC CAT AAT CAT GGA ACG GTT TAT TTT CCA AGA GAA TGG    1343
Ser Lys Gln Gly His Asn His Gly Thr Val Tyr Phe Pro Arg Glu Trp
                435             440             445

AAA GTA AGA AAA TTA CAA AAT TCA TTT AAA GTT CAA GCT GAA GAT TGG    1391
Lys Val Arg Lys Leu Gln Asn Ser Phe Lys Val Gln Ala Glu Asp Trp
        450             455             460

TTA AAT GTT AGT CTT TAT AAG TAC AAC GCG GTA CAT TCT TTC AGG AAT    1439
Leu Asn Val Ser Leu Tyr Lys Tyr Asn Ala Val His Ser Phe Arg Asn
465             470             475

ATA ACT CTA GAA TTT GGC TAC TAC GCA CCT CTA ATT AGA AAG TGT CAG    1487
Ile Thr Leu Glu Phe Gly Tyr Tyr Ala Pro Leu Ile Arg Lys Cys Gln
480             485             490             495

AGT TAT AAA AAA AAA TAC ATT CTC TAT TAT TTG AAG AAT CTT CCG AGT    1535
Ser Tyr Lys Lys Lys Tyr Ile Leu Tyr Tyr Leu Lys Asn Leu Pro Ser
            500             505             510

GGC TCC TCG GGG CCC AAA CAA ACC ATG GAC AAA TTT AGT GAT ATA ATG    1583
Gly Ser Ser Gly Pro Lys Gln Thr Met Asp Lys Phe Ser Asp Ile Met
                515             520             525

AAA GTT GAG AAC GGA ATC GAC GTT GTG GAT CGG ATA GGC GGG CCT ATC    1631
Lys Val Glu Asn Gly Ile Asp Val Val Asp Arg Ile Gly Gly Pro Ile
        530             535             540

GAA GCA CTA TCT GTG GAG GAT GGA CTA GCA CCA TTG ATG GAT AAT GAT    1679
Glu Ala Leu Ser Val Glu Asp Gly Leu Ala Pro Leu Met Asp Asn Asp
545             550             555

AGC AAT AAT TGT GAC CAT TTA GAG GAT CAA AAA AAG GAA AGG GAC AGA    1727
Ser Asn Asn Cys Asp His Leu Glu Asp Gln Lys Lys Glu Arg Asp Arg
560             565             570             575

AGG CTT CGC ATG TTG ATT GAC CAA TAT GAA AGA AAT GTG ATG ATG GCT    1775
Arg Leu Arg Met Leu Ile Asp Gln Tyr Glu Arg Asn Val Met Met Ala
            580             585             590

AAC GAC GAT CTT GAA GAC GAA GAA ACT TCT TTT AAT GAT GAC CCT ATT    1823
Asn Asp Asp Leu Glu Asp Glu Glu Thr Ser Phe Asn Asp Asp Pro Ile
                595             600             605

GTC GAT AGC GAT AGC GAT AAC AGC AAT AAT ATT GGC AAT GAA ACA TTT    1871
Val Asp Ser Asp Ser Asp Asn Ser Asn Asn Ile Gly Asn Glu Thr Phe
        610             615             620

GGT AGA AGC GAC GAA GAC GAG TCT CTA TGT GAA ATT CTG TCC CAG AGA    1919
Gly Arg Ser Asp Glu Asp Glu Ser Leu Cys Glu Ile Leu Ser Gln Arg
625             630             635

CAG CCG CGT AAA GCG CCA GTT ATC AGT GAG TCC CTT TCA GAT TCA GAT    1967
Gln Pro Arg Lys Ala Pro Val Ile Ser Glu Ser Leu Ser Asp Ser Asp
640             645             650             655

CTG GAA ATA CTC TAACTTTTTA CTCTTTAAAT TGACGAGAA AACCCCAGGA         2019
Leu Glu Ile Leu
            660

AATATTCCAC ACAAATCTAT GCACATTACA TTCTAGAATA AATTAATAAA TAAAAATATA  2079

TACATATATA TTAATATGTA TATATGTATG AATATAGTTT TCATTACAAA ATAAGGCTTA  2139

CTGTAGAGCA TGTTGGAAAT ATTCAGGATC TTCTTCTATA GATTCCTTGA TAATATCCAA  2199

ACCTCCCTGG AACTCCCCAT TGATATATAA CTGAGGAAAA GTAGGCCAAT CAGAAAACTT  2259

CTTCAAGCTT TGTCTAACGT TTTCGTCTCT TAATATATCA AAAAATCCGA ACCTTATTTG  2319

GTGTTCTCTG AGGATACCAA CTAACTGTCT AGAAAATCCG CATTTAGGTT CTGATGGGCT  2379
```

```
TCCTTTCATG AATAGCATCA CAGGTGCAGC TTGTACTAGC TTCACCAGCC TAGCATTTAT    2439

TTCTTCTTCA GTTTCGTCCT CTTCATCATC GGAAGACCCG CTGCTTTCCT CATCAGACGT    2499

AGATTTAGGA CCCTTGGCAT TGTTCGCTAG TGAGGCAGAA GCATTCGAAA GAATTTCTAA    2559

GCTTTTCACA AACTCCTTAG GATCTGCGGC TGATATTTCT TTTACAATAG TACCATTTTG    2619

AATGAAGACG AAGTATGGTA CGGCTGCAAT CTCAAAAAGG TCTGATATTT CTGGATGTTC    2679

GTCTGCATCT ATTGATAAAA ACCGGACATC CTCTTGCCTA ACTTTTTCAC TAACAGCTTC    2739

TAGCACCTGG CTCATAGTTT TGC                                            2762
```

( 2 ) INFORMATION FOR SEQ ID NO:13:

( i ) SEQUENCE CHARACTERISTICS:
    ( A ) LENGTH: 659 amino acids
    ( B ) TYPE: amino acid
    ( D ) TOPOLOGY: linear ( i i ) MOLECULE TYPE: protein
    ( A ) DESCRIPTION: yeast RAD24 protein ( x i ) SEQUENCE DESCRIPTION: SEQ ID NO:13:

```
Met Asp Ser Thr Asn Leu Asn Lys Arg Pro Leu Leu Gln Tyr Ser Leu
 1               5                  10                  15

Ser Ser Leu Gly Ser Gln Ile Thr Lys Trp Ser Ser Ser Arg Pro Thr
            20                  25                  30

Ser Pro Val Arg Lys Ala Arg Ser Thr Glu Asn Asp Phe Leu Ser Lys
        35                  40                  45

Gln Asp Thr Ser Ser Ile Leu Pro Ser Ile Asn Asp Gly Gly Glu
    50                  55                  60

Gln Trp Tyr Glu Lys Phe Lys Pro Asn Cys Leu Glu Gln Val Ala Ile
 65                  70                  75                  80

His Lys Arg Lys Leu Lys Asp Val Gln Glu Ala Leu Asp Ala Met Phe
                85                  90                  95

Leu Pro Asn Ala Lys His Arg Ile Leu Leu Ser Gly Pro Ser Gly
                100                 105                 110

Cys Ser Lys Ser Thr Val Ile Lys Glu Leu Ser Lys Ile Leu Val Pro
            115                 120                 125

Lys Tyr Arg Gln Asn Ser Asn Gly Thr Ser Phe Arg Ser Thr Pro Asn
130                 135                 140

Glu His Lys Val Thr Glu Phe Arg Gly Asp Cys Ile Val Asn Asp Leu
145                 150                 155                 160

Pro Gln Met Glu Ser Phe Ser Glu Phe Leu Lys Gly Ala Arg Tyr Leu
                165                 170                 175

Val Met Ser Asn Leu Ser Leu Ile Leu Ile Glu Asp Leu Pro Asn Val
                180                 185                 190

Phe His Ile Asp Thr Arg Arg Arg Phe Gln Gln Leu Ile Leu Gln Trp
        195                 200                 205

Leu Tyr Ser Ser Glu Pro Leu Leu Pro Pro Leu Val Ile Cys Ile Thr
210                 215                 220

Glu Cys Glu Ile Pro Glu Asn Asp Asn Asn Tyr Arg Lys Phe Gly Ile
225                 230                 235                 240

Asp Tyr Thr Phe Ser Ala Glu Thr Ile Met Asn Lys Glu Ile Leu Met
                245                 250                 255

His Pro Arg Leu Lys Arg Ile Lys Phe Asn Pro Ile Asn Ser Thr Leu
                260                 265                 270

Leu Lys Lys His Leu Lys Phe Ile Cys Val Gln Asn Met Lys Met Leu
            275                 280                 285
```

| | | | | | | | | | | | | | | |
|---|---|---|---|---|---|---|---|---|---|---|---|---|---|---|
| Lys | Glu | Lys | Asn | Lys | Trp | Asn | Lys | Arg | Gln | Glu | Val | Ile | Asp | Tyr | Ile |
| | 290 | | | | 295 | | | | | 300 | | | | |
| Ala | Gln | Glu | Thr | Gly | Asp | Ile | Arg | Ser | Ala | Ile | Thr | Thr | Leu | Gln | Phe |
| 305 | | | | | 310 | | | | 315 | | | | | 320 |
| Trp | Ala | Thr | Ser | Ser | Gly | Ser | Leu | Pro | Ile | Ser | Thr | Arg | Glu | Ser | Thr |
| | | | | 325 | | | | 330 | | | | | 335 | |
| Ile | Ser | Tyr | Phe | His | Ala | Ile | Gly | Lys | Val | Ile | His | Gly | Ser | His | Ser |
| | | | 340 | | | | | 345 | | | | | 350 | | |
| Thr | Asn | Asn | Asp | Asn | Glu | Met | Ile | Asn | Asn | Leu | Phe | Glu | Asn | Ser | Asn |
| | | 355 | | | | 360 | | | | | 365 | | | | |
| Asn | Leu | Leu | Ser | Lys | Glu | Asp | Phe | Lys | Leu | Gly | Ile | Leu | Glu | Asn | Tyr |
| | 370 | | | | 375 | | | | | 380 | | | | | |
| Asn | Thr | Phe | Asn | Lys | Gly | Glu | Phe | Ser | Ile | Ser | Asp | Ala | Ser | Ser | Ile |
| 385 | | | | | 390 | | | | 395 | | | | | | 400 |
| Val | Asp | Cys | Leu | Ser | Glu | Cys | Asp | Asn | Met | Asn | Gly | Leu | Pro | Glu | Ser |
| | | | | 405 | | | | | 410 | | | | | 415 | |
| Asn | Glu | Tyr | Gly | Leu | Arg | Glu | Val | Arg | Lys | Thr | Phe | Arg | Asn | Ile | Ser |
| | | | 420 | | | | | 425 | | | | | 430 | | |
| Lys | Gln | Gly | His | Asn | His | Gly | Thr | Val | Tyr | Phe | Pro | Arg | Glu | Trp | Lys |
| | | 435 | | | | | 440 | | | | | 445 | | | |
| Val | Arg | Lys | Leu | Gln | Asn | Ser | Phe | Lys | Val | Gln | Ala | Glu | Asp | Trp | Leu |
| | 450 | | | | | 455 | | | | | 460 | | | | |
| Asn | Val | Ser | Leu | Tyr | Lys | Tyr | Asn | Ala | Val | His | Ser | Phe | Arg | Asn | Ile |
| 465 | | | | | 470 | | | | | 475 | | | | | 480 |
| Thr | Leu | Glu | Phe | Gly | Tyr | Tyr | Ala | Pro | Leu | Ile | Arg | Lys | Cys | Gln | Ser |
| | | | | 485 | | | | | 490 | | | | | 495 | |
| Tyr | Lys | Lys | Lys | Tyr | Ile | Leu | Tyr | Tyr | Leu | Lys | Asn | Leu | Pro | Ser | Gly |
| | | | 500 | | | | | 505 | | | | | 510 | | |
| Ser | Ser | Gly | Pro | Lys | Gln | Thr | Met | Asp | Lys | Phe | Ser | Asp | Ile | Met | Lys |
| | | 515 | | | | | 520 | | | | | 525 | | | |
| Val | Glu | Asn | Gly | Ile | Asp | Val | Val | Asp | Arg | Ile | Gly | Gly | Pro | Ile | Glu |
| | 530 | | | | | 535 | | | | | 540 | | | | |
| Ala | Leu | Ser | Val | Glu | Asp | Gly | Leu | Ala | Pro | Leu | Met | Asp | Asn | Asp | Ser |
| 545 | | | | | 550 | | | | | 555 | | | | | 560 |
| Asn | Asn | Cys | Asp | His | Leu | Glu | Asp | Gln | Lys | Lys | Glu | Arg | Asp | Arg | Arg |
| | | | | 565 | | | | | 570 | | | | | 575 | |
| Leu | Arg | Met | Leu | Ile | Asp | Gln | Tyr | Glu | Arg | Asn | Val | Met | Met | Ala | Asn |
| | | | 580 | | | | | 585 | | | | | 590 | | |
| Asp | Asp | Leu | Glu | Asp | Glu | Glu | Thr | Ser | Phe | Asn | Asp | Pro | Ile | Val |
| | | 595 | | | | | 600 | | | | | 605 | | | |
| Asp | Ser | Asp | Ser | Asp | Asn | Ser | Asn | Asn | Ile | Gly | Asn | Glu | Thr | Phe | Gly |
| | 610 | | | | | 615 | | | | | 620 | | | | |
| Arg | Ser | Asp | Glu | Asp | Glu | Ser | Leu | Cys | Glu | Ile | Leu | Ser | Gln | Arg | Gln |
| 625 | | | | | 630 | | | | 635 | | | | | | 640 |
| Pro | Arg | Lys | Ala | Pro | Val | Ile | Ser | Glu | Ser | Leu | Ser | Asp | Ser | Asp | Leu |
| | | | | 645 | | | | | 650 | | | | | 655 | |
| Glu | Ile | Leu | | | | | | | | | | | | | |

( 2 ) INFORMATION FOR SEQ ID NO:14:

( i ) SEQUENCE CHARACTERISTICS:
( A ) LENGTH: 8351 base pairs
( B ) TYPE: nucleic acid
( C ) STRANDEDNESS: single
( D ) TOPOLOGY: linear ( i i ) MOLECULE TYPE: cDNA to mRNA
  ( A ) DESCRIPTION: yeast MEC1 cDNA ( i i i ) HYPOTHETICAL: NO ( i v ) ANTI-SENSE: NO ( v i ) ORIGINAL SOURCE:
  ( A ) ORGANISM: Saccharomyces cerevisiae ( i x ) FEATURE:
  ( A ) NAME/KEY: CDS
  ( B ) LOCATION: 784..7890

( x i ) SEQUENCE DESCRIPTION: SEQ ID NO:14:

```
ATAAGCTTAC TGACCAAGAA AGAGCACGCG TGTTGGAGTT TCAAGATTCC ATTCACTATT          60

CTCCGCGGTA CTCAGACGAT AACTATGAGT ACAGGCATGT GATGTTACCT AAGGCCATGC         120

TAAAAGTTAT CCCATCTGAT TACTTCAATT CGGAAGTGGG GACCCTGCGT ATATTAACAG         180

AAGACGAATG GAGAGGCCTC GGCATCACAC AGTCTTTGGG GTGGGAACAT TATGAATGCC         240

ATGCGCCAGA ACTACACATT TTGCTATTCA AAAGGCCGCT GAACTACGAG GCCGAGCTGA         300

GGGCAGCGAC CGCTGCTGCT CAACAGCAAC AGCAACAGCA GCAACAGCAG CAACAACAAC         360

AACAGCAACA TCAAACACAA TCGATTTCGA ACGATATGCA AGTTCCACCC CAAATCTCCT         420

AGCTTTGATA TACTCTAATT ACTGAAATTG AATTCCTTTT CAAGGCTCCA TAACTATATG         480

GAGCATACTA TGTACTTATC ATAATAAAGA ATAAACAAAC AAGCAAACAA AAAAAAAAA          540

AACTATGGAT CATAGTTTTC ACCAACAAGC ATTAGAATAC AAATAAAATT TATATAGTGA         600

ATATCCTTCA AATAAATTTC TTCTTTCCCT TATAAATCAA ATAGATGGAA CGCACGCTCC         660

AAAACTAGTC AACTAGAAAA AAATACCCGC CGACGGACAA TTTTGAAGAG AGATGATTAA         720

TGAAGACAAA GTGAGGCTGG ACAACAAGAA CGACATACAC CGCGTAAAGG CCCACAAGAC         780
```

| | | | | | | | | | | | | | | | |
|---|---|---|---|---|---|---|---|---|---|---|---|---|---|---|---|
| TGC | ATG | GAA | TCA | CAC | GTC | AAA | TAT | CTT | GAC | GAA | TTG | ATA | TTG | GCA | ATA | 828 |
| | Met | Glu | Ser | His | Val | Lys | Tyr | Leu | Asp | Glu | Leu | Ile | Leu | Ala | Ile | |
| | 1 | | | | 5 | | | | | 10 | | | | | 15 | |

| AAA | GAC | CTG | AAC | TCG | GGG | GTG | GAT | TCA | AAG | GTG | CAG | ATT | AAA | AAA | GTG | 876 |
|---|---|---|---|---|---|---|---|---|---|---|---|---|---|---|---|---|
| Lys | Asp | Leu | Asn | Ser | Gly | Val | Asp | Ser | Lys | Val | Gln | Ile | Lys | Lys | Val | |
| | | | | 20 | | | | | 25 | | | | | 30 | | |

| CCC | ACG | GAT | CCA | TCT | TCT | TCT | CAG | GAG | TAC | GCC | AAG | AGT | TTA | AAG | ATC | 924 |
|---|---|---|---|---|---|---|---|---|---|---|---|---|---|---|---|---|
| Pro | Thr | Asp | Pro | Ser | Ser | Ser | Gln | Glu | Tyr | Ala | Lys | Ser | Leu | Lys | Ile | |
| | | | 35 | | | | | 40 | | | | | 45 | | | |

| CTG | AAC | ACC | CTC | ATA | AGA | AAC | CTA | AAA | GAT | CAA | AGA | AGG | AAC | AAT | ATC | 972 |
|---|---|---|---|---|---|---|---|---|---|---|---|---|---|---|---|---|
| Leu | Asn | Thr | Leu | Ile | Arg | Asn | Leu | Lys | Asp | Gln | Arg | Arg | Asn | Asn | Ile | |
| | | | 50 | | | | | 55 | | | | | 60 | | | |

| ATG | AAA | AAT | GAT | ACT | ATA | TTT | TCG | AAA | ACA | GTT | TCC | GCC | CTT | GCC | TTA | 1020 |
|---|---|---|---|---|---|---|---|---|---|---|---|---|---|---|---|---|
| Met | Lys | Asn | Asp | Thr | Ile | Phe | Ser | Lys | Thr | Val | Ser | Ala | Leu | Ala | Leu | |
| | 65 | | | | | 70 | | | | | 75 | | | | | |

| TTG | TTG | GAG | TAC | AAC | CCC | TTC | TTG | CTT | GTT | ATG | AAG | GAT | TCC | AAC | GGG | 1068 |
|---|---|---|---|---|---|---|---|---|---|---|---|---|---|---|---|---|
| Leu | Leu | Glu | Tyr | Asn | Pro | Phe | Leu | Leu | Val | Met | Lys | Asp | Ser | Asn | Gly | |
| 80 | | | | | 85 | | | | | 90 | | | | | 95 | |

| AAC | TTT | GAG | ATA | CAA | AGG | CTG | ATA | GAT | GAT | TTC | CTC | AAC | ATA | TCC | GTT | 1116 |
|---|---|---|---|---|---|---|---|---|---|---|---|---|---|---|---|---|
| Asn | Phe | Glu | Ile | Gln | Arg | Leu | Ile | Asp | Asp | Phe | Leu | Asn | Ile | Ser | Val | |
| | | | | 100 | | | | | 105 | | | | | 110 | | |

| CTG | AAC | TAT | GAT | AAT | TAC | CAC | AGA | ATA | TGG | TTT | ATG | AGG | CGA | AAA | TTA | 1164 |
|---|---|---|---|---|---|---|---|---|---|---|---|---|---|---|---|---|
| Leu | Asn | Tyr | Asp | Asn | Tyr | His | Arg | Ile | Trp | Phe | Met | Arg | Arg | Lys | Leu | |
| | | | 115 | | | | | 120 | | | | | 125 | | | |

| GGC | AGC | TGG | TGC | AAA | GCA | TGT | GTC | GAA | TTT | TAC | GGA | AAA | CCT | GCT | AAG | 1212 |
|---|---|---|---|---|---|---|---|---|---|---|---|---|---|---|---|---|
| Gly | Ser | Trp | Cys | Lys | Ala | Cys | Val | Glu | Phe | Tyr | Gly | Lys | Pro | Ala | Lys | |
| | | 130 | | | | | 135 | | | | | 140 | | | | |

| TTT | CAG | CTT | ACT | GCA | CAT | TTT | GAG | AAC | ACC | ATG | AAT | CTT | TAC | GAA | CAG | 1260 |

```
        Phe Gln Leu Thr Ala His Phe Glu Asn Thr Met Asn Leu Tyr Glu Gln
            145                 150                 155

GCC TTG ACT GAA GTC TTG TTG GGC AAG ACT GAG CTT CTC AAA TTT TAT              1308
Ala Leu Thr Glu Val Leu Leu Gly Lys Thr Glu Leu Leu Lys Phe Tyr
160                 165                 170                 175

GAC ACC TTG AAG GGT CTA TAC ATT CTT TTA TAC TGG TTC ACT TCG GAG              1356
Asp Thr Leu Lys Gly Leu Tyr Ile Leu Leu Tyr Trp Phe Thr Ser Glu
                180                 185                 190

TAT AGT ACT TTT GGG AAC TCT ATA GCA TTC TTA GAT TCT TCT TTG GGG              1404
Tyr Ser Thr Phe Gly Asn Ser Ile Ala Phe Leu Asp Ser Ser Leu Gly
            195                 200                 205

TTC ACG AAA TTT GAC TTT AAC TTC CAA CGA TTA ATC AGG ATT GTT CTT              1452
Phe Thr Lys Phe Asp Phe Asn Phe Gln Arg Leu Ile Arg Ile Val Leu
        210                 215                 220

TAC GTC TTT GAT TCC TGC GAA CTA GCA GCA CTA GAA TAT GCC GAA ATC              1500
Tyr Val Phe Asp Ser Cys Glu Leu Ala Ala Leu Glu Tyr Ala Glu Ile
    225                 230                 235

CAA CTC AAA TAT ATT TCT CTA GTT GTG GAC TAT GTT TGC AAT AGA ACA              1548
Gln Leu Lys Tyr Ile Ser Leu Val Val Asp Tyr Val Cys Asn Arg Thr
240                 245                 250                 255

ATT TCC ACA GCC CTG GAT GCC CCA GCG TTA GTT TGT TGT GAA CAA TTA              1596
Ile Ser Thr Ala Leu Asp Ala Pro Ala Leu Val Cys Cys Glu Gln Leu
                260                 265                 270

AAG TTT GTA TTG ACT ACT ATG CAT CAT TTT TTG GAT AAC AAG TAT GGG              1644
Lys Phe Val Leu Thr Thr Met His His Phe Leu Asp Asn Lys Tyr Gly
            275                 280                 285

CTC TTG GAT AAT GAC CCC ACT ATG GCC AAA GGA ATT CTT CGA CTA TAT              1692
Leu Leu Asp Asn Asp Pro Thr Met Ala Lys Gly Ile Leu Arg Leu Tyr
        290                 295                 300

TCT CTT TGC ATT TCT AAC GAT TTC TCA AAA TGC TTT GTA GAC CAC TTC              1740
Ser Leu Cys Ile Ser Asn Asp Phe Ser Lys Cys Phe Val Asp His Phe
    305                 310                 315

CCA ATT GAC CAG TGG GCA GAT TTT TCA CAA AGT GAA CAT TTT CCG TTC              1788
Pro Ile Asp Gln Trp Ala Asp Phe Ser Gln Ser Glu His Phe Pro Phe
320                 325                 330                 335

ACG CAG TTG ACT AAT AAA GCT CTC TCG ATT GTA TAT TTT GAT TTG AAA              1836
Thr Gln Leu Thr Asn Lys Ala Leu Ser Ile Val Tyr Phe Asp Leu Lys
                340                 345                 350

AGA AGG TCC CTA CCT GTT GAA GCT TTA AAG TAC GAT AAT AAG TTC AAC              1884
Arg Arg Ser Leu Pro Val Glu Ala Leu Lys Tyr Asp Asn Lys Phe Asn
            355                 360                 365

ATC TGG GTA TAC CAA TCG GAG CCG GAC TCG AGC TTG AAA AAT GTC ACT              1932
Ile Trp Val Tyr Gln Ser Glu Pro Asp Ser Ser Leu Lys Asn Val Thr
        370                 375                 380

TCT CCC TTT GAT GAT CGA TAT AAG CAG CTG GAA AAG CTA AGG TTG CTA              1980
Ser Pro Phe Asp Asp Arg Tyr Lys Gln Leu Glu Lys Leu Arg Leu Leu
    385                 390                 395

GTA CTA AAG AAG TTT AAC AAG ACA GAA AGA GGA ACT TTG CTC AAA TAC              2028
Val Leu Lys Lys Phe Asn Lys Thr Glu Arg Gly Thr Leu Leu Lys Tyr
400                 405                 410                 415

CGC GTG AAC CAG CTA AGT CCT GGA TTT TTT CAA AGA GCT GGA AAC GAT              2076
Arg Val Asn Gln Leu Ser Pro Gly Phe Phe Gln Arg Ala Gly Asn Asp
                420                 425                 430

TTC AAG CTA ATT TTA AAT GAA GCA TCT GTA TCC ATT CAA ACT TGT TTC              2124
Phe Lys Leu Ile Leu Asn Glu Ala Ser Val Ser Ile Gln Thr Cys Phe
            435                 440                 445

AAG ACA AAC AAT ATA ACA AGG CTA ACA TCA TGG ACT GTA ATT CTC GGA              2172
Lys Thr Asn Asn Ile Thr Arg Leu Thr Ser Trp Thr Val Ile Leu Gly
        450                 455                 460

CGT CTA GCC TGT CTA GAA TCA GAG AAG TTT TCC GGC ACT CTG CCA AAT              2220
```

| | | | | | | | | | | | | | | | |
|---|---|---|---|---|---|---|---|---|---|---|---|---|---|---|---|
| Arg | Leu | Ala | Cys | Leu | Glu | Ser | Glu | Lys | Phe | Ser | Gly | Thr | Leu | Pro | Asn |
| 465 | | | | | 470 | | | | | 475 | | | | | |

| TCC | ACA | AAG | GAT | ATG | GAT | AAT | TGG | TAT | GTT | TGT | CAT | TTA | TGC | GAT | ATT | 2268 |
|---|---|---|---|---|---|---|---|---|---|---|---|---|---|---|---|---|
| Ser | Thr | Lys | Asp | Met | Asp | Asn | Trp | Tyr | Val | Cys | His | Leu | Cys | Asp | Ile | |
| 480 | | | | 485 | | | | | 490 | | | | | 495 | | |

| GAG | AAA | ACT | GGC | AAC | CCT | TTC | GTG | CGA | ATA | AAT | CCA | AAT | AGA | CCA | GAG | 2316 |
|---|---|---|---|---|---|---|---|---|---|---|---|---|---|---|---|---|
| Glu | Lys | Thr | Gly | Asn | Pro | Phe | Val | Arg | Ile | Asn | Pro | Asn | Arg | Pro | Glu | |
| | | | | 500 | | | | | 505 | | | | | 510 | | |

| GCT | GCG | GGT | AAA | TCA | GAA | ATC | TTC | AGG | ATA | CTT | CAT | TCA | AAC | TTT | CTA | 2364 |
|---|---|---|---|---|---|---|---|---|---|---|---|---|---|---|---|---|
| Ala | Ala | Gly | Lys | Ser | Glu | Ile | Phe | Arg | Ile | Leu | His | Ser | Asn | Phe | Leu | |
| | | | | 515 | | | | | 520 | | | | | 525 | | |

| TCT | CAC | CCA | AAT | ATA | GAT | GAA | TTT | AGC | GAA | TCT | TTG | TTA | AGT | GGC | ATC | 2412 |
|---|---|---|---|---|---|---|---|---|---|---|---|---|---|---|---|---|
| Ser | His | Pro | Asn | Ile | Asp | Glu | Phe | Ser | Glu | Ser | Leu | Leu | Ser | Gly | Ile | |
| | | 530 | | | | | 535 | | | | | 540 | | | | |

| TTA | TTT | TCT | CTA | CAT | AGG | ATA | TTT | TCA | CAC | TTT | CAA | CCT | CCA | AAA | CTT | 2460 |
|---|---|---|---|---|---|---|---|---|---|---|---|---|---|---|---|---|
| Leu | Phe | Ser | Leu | His | Arg | Ile | Phe | Ser | His | Phe | Gln | Pro | Pro | Lys | Leu | |
| | 545 | | | | | 550 | | | | | 555 | | | | | |

| ACA | GAT | GGA | AAC | GGT | CAA | ATC | AAT | AAG | AGC | TTT | AAA | CTG | GTA | CAA | AAG | 2508 |
|---|---|---|---|---|---|---|---|---|---|---|---|---|---|---|---|---|
| Thr | Asp | Gly | Asn | Gly | Gln | Ile | Asn | Lys | Ser | Phe | Lys | Leu | Val | Gln | Lys | |
| 560 | | | | | 565 | | | | | 570 | | | | | 575 | |

| TGC | TTT | ATG | AAT | TCT | AAC | AGA | TAC | CTA | CGT | TTA | TTA | AGT | ACT | AGA | ATT | 2556 |
|---|---|---|---|---|---|---|---|---|---|---|---|---|---|---|---|---|
| Cys | Phe | Met | Asn | Ser | Asn | Arg | Tyr | Leu | Arg | Leu | Leu | Ser | Thr | Arg | Ile | |
| | | | | 580 | | | | | 585 | | | | | 590 | | |

| ATA | CCT | TTA | TTC | AAT | ATA | TCA | GAC | TCT | CAT | AAT | TCC | GAA | GAT | GAA | CAC | 2604 |
|---|---|---|---|---|---|---|---|---|---|---|---|---|---|---|---|---|
| Ile | Pro | Leu | Phe | Asn | Ile | Ser | Asp | Ser | His | Asn | Ser | Glu | Asp | Glu | His | |
| | | | 595 | | | | | 600 | | | | | 605 | | | |

| ACT | GCC | ACG | CTG | ATA | AAG | TTT | CTA | CAA | TCT | CAA | AAA | TTG | CCA | GTG | GTG | 2652 |
|---|---|---|---|---|---|---|---|---|---|---|---|---|---|---|---|---|
| Thr | Ala | Thr | Leu | Ile | Lys | Phe | Leu | Gln | Ser | Gln | Lys | Leu | Pro | Val | Val | |
| | | 610 | | | | | 615 | | | | | 620 | | | | |

| AAA | GAA | AAT | TTA | GTC | ATT | GCT | TGG | ACA | CAA | TTA | ACA | TTG | ACG | ACT | TCT | 2700 |
|---|---|---|---|---|---|---|---|---|---|---|---|---|---|---|---|---|
| Lys | Glu | Asn | Leu | Val | Ile | Ala | Trp | Thr | Gln | Leu | Thr | Leu | Thr | Thr | Ser | |
| 625 | | | | | 630 | | | | | 635 | | | | | | |

| AAT | GAT | GTA | TTT | GAT | ACA | CTA | CTT | TTG | AAA | CTG | ATT | GAT | ATT | TTC | AAT | 2748 |
|---|---|---|---|---|---|---|---|---|---|---|---|---|---|---|---|---|
| Asn | Asp | Val | Phe | Asp | Thr | Leu | Leu | Leu | Lys | Leu | Ile | Asp | Ile | Phe | Asn | |
| 640 | | | | | 645 | | | | | 650 | | | | | 655 | |

| TCT | GAT | GAT | TAT | AGT | TTA | CGA | ATA | ATG | ATG | ACT | TTG | CAA | ATT | AAA | AAT | 2796 |
|---|---|---|---|---|---|---|---|---|---|---|---|---|---|---|---|---|
| Ser | Asp | Asp | Tyr | Ser | Leu | Arg | Ile | Met | Met | Thr | Leu | Gln | Ile | Lys | Asn | |
| | | | | 660 | | | | | 665 | | | | | 670 | | |

| ATG | GCC | AAA | ATT | TTA | AAG | AAA | ACA | CCA | TAT | CAA | TTA | CTA | TCG | CCT | ATT | 2844 |
|---|---|---|---|---|---|---|---|---|---|---|---|---|---|---|---|---|
| Met | Ala | Lys | Ile | Leu | Lys | Lys | Thr | Pro | Tyr | Gln | Leu | Leu | Ser | Pro | Ile | |
| | | | 675 | | | | | 680 | | | | | 685 | | | |

| TTA | CCT | GTA | TTA | CTA | AGA | CAG | TTG | GGA | AAA | AAC | CTC | GTG | GAA | AGA | AAA | 2892 |
|---|---|---|---|---|---|---|---|---|---|---|---|---|---|---|---|---|
| Leu | Pro | Val | Leu | Leu | Arg | Gln | Leu | Gly | Lys | Asn | Leu | Val | Glu | Arg | Lys | |
| | | 690 | | | | | 695 | | | | | 700 | | | | |

| GTT | GGC | TTT | CAA | AAT | TTA | ATA | GAA | TTA | TTG | GGA | TAT | CCT | TCA | AAA | ACA | 2940 |
|---|---|---|---|---|---|---|---|---|---|---|---|---|---|---|---|---|
| Val | Gly | Phe | Gln | Asn | Leu | Ile | Glu | Leu | Leu | Gly | Tyr | Pro | Ser | Lys | Thr | |
| | 705 | | | | | 710 | | | | | 715 | | | | | |

| ATT | CTC | GAT | ATT | TTC | CAG | AGA | TAT | ATC | ATC | CCT | TAT | GCA | ATT | ATT | CAA | 2988 |
|---|---|---|---|---|---|---|---|---|---|---|---|---|---|---|---|---|
| Ile | Leu | Asp | Ile | Phe | Gln | Arg | Tyr | Ile | Ile | Pro | Tyr | Ala | Ile | Ile | Gln | |
| 720 | | | | | 725 | | | | | 730 | | | | | 735 | |

| TAT | AAG | AGC | GAT | GTG | CTA | AGT | GAA | ATT | GCT | AAG | ATT | ATG | TGT | GAT | GGC | 3036 |
|---|---|---|---|---|---|---|---|---|---|---|---|---|---|---|---|---|
| Tyr | Lys | Ser | Asp | Val | Leu | Ser | Glu | Ile | Ala | Lys | Ile | Met | Cys | Asp | Gly | |
| | | | | 740 | | | | | 745 | | | | | 750 | | |

| GAT | ACA | AGT | TTA | ATT | AAC | CAA | ATG | AAG | GTT | AAT | TTA | CTG | AAA | AAA | AAC | 3084 |
|---|---|---|---|---|---|---|---|---|---|---|---|---|---|---|---|---|
| Asp | Thr | Ser | Leu | Ile | Asn | Gln | Met | Lys | Val | Asn | Leu | Leu | Lys | Lys | Asn | |
| | | | 755 | | | | | 760 | | | | | 765 | | | |

| AGT | AGG | CAA | ATA | TTT | GCC | GTA | GCT | TTG | GTA | AAA | CAC | GGA | TTA | TTT | TCT | 3132 |
|---|---|---|---|---|---|---|---|---|---|---|---|---|---|---|---|---|
| Ser | Arg | Gln | Ile | Phe | Ala | Val | Ala | Leu | Val | Lys | His | Gly | Leu | Phe | Ser | |
| | | 770 | | | | | 775 | | | | | 780 | | | | |

| TTG | GAT | ATC | TTG | GAA | ACC | CTT | TTT | TTA | AAT | AGG | GCT | CCA | ACT | TTT | GAC | 3180 |
|---|---|---|---|---|---|---|---|---|---|---|---|---|---|---|---|---|

```
Leu Asp Ile Leu Glu Thr Leu Phe Leu Asn Arg Ala Pro Thr Phe Asp
785                 790                 795

AAA GGA TAT ATA ACT GCA TAC CTT CCC GAT TAT AAA ACT TTA GCT GAA    3228
Lys Gly Tyr Ile Thr Ala Tyr Leu Pro Asp Tyr Lys Thr Leu Ala Glu
800                 805                 810                 815

ATA ACG AAG CTC TAC AAA AAC AGC GTT ACT AAA GAT GCA AGT GAC AGC    3276
Ile Thr Lys Leu Tyr Lys Asn Ser Val Thr Lys Asp Ala Ser Asp Ser
                820                 825                 830

GAG AAT GCT AAT ATG ATT TTA TGC TCT TTG CGA TTT TTA ATC ACC AAT    3324
Glu Asn Ala Asn Met Ile Leu Cys Ser Leu Arg Phe Leu Ile Thr Asn
            835                 840                 845

TTT GAA AAA GAC AAA AGG CAT GGT TCG AAG TAC AAA AAT ATC AAT AAC    3372
Phe Glu Lys Asp Lys Arg His Gly Ser Lys Tyr Lys Asn Ile Asn Asn
        850                 855                 860

TGG ACG GAT GAT CAG GAA CAA GCG TTC CAA AAG AAA CTA CAG GAT AAT    3420
Trp Thr Asp Asp Gln Glu Gln Ala Phe Gln Lys Lys Leu Gln Asp Asn
    865                 870                 875

ATC TTA GGT ATT TTC CAA GTT TTT TCG AGT GAC ATA CAT GAT GTT GAA    3468
Ile Leu Gly Ile Phe Gln Val Phe Ser Ser Asp Ile His Asp Val Glu
880                 885                 890                 895

GGC CGC ACC ACT TAC TAC GAA AAG TTA AGG GTT ATC AAT GGC ATT TCT    3516
Gly Arg Thr Thr Tyr Tyr Glu Lys Leu Arg Val Ile Asn Gly Ile Ser
                900                 905                 910

TTT CTT ATC ATA TAT GCC CCC AAA AAA TCA ATA ATT TCC GCA TTA GCC    3564
Phe Leu Ile Ile Tyr Ala Pro Lys Lys Ser Ile Ile Ser Ala Leu Ala
            915                 920                 925

CAG ATT AGT ATT TGT TTG CAA ACA GGA CTT GGG CTT AAG GAA GTT CGA    3612
Gln Ile Ser Ile Cys Leu Gln Thr Gly Leu Gly Leu Lys Glu Val Arg
        930                 935                 940

TAC GAG GCC TTT AGA TGT TGG CAT CTG TTA GTT CGC CAT CTA AAT GAT    3660
Tyr Glu Ala Phe Arg Cys Trp His Leu Leu Val Arg His Leu Asn Asp
    945                 950                 955

GAA GAA CTC TCT ACT GTT ATA GAT AGC TTA ATT GCA TTC ATA CTT CAA    3708
Glu Glu Leu Ser Thr Val Ile Asp Ser Leu Ile Ala Phe Ile Leu Gln
960                 965                 970                 975

AAG TGG TCT GAG TTC AAC GGA AAA CTT CGA AAT ATA GTG TAC AGT ATA    3756
Lys Trp Ser Glu Phe Asn Gly Lys Leu Arg Asn Ile Val Tyr Ser Ile
                980                 985                 990

CTG GAT ACC TTA ATC AAA GAG AAA TCG GAC CTG ATT TTG AAA TTA AAA    3804
Leu Asp Thr Leu Ile Lys Glu Lys Ser Asp Leu Ile Leu Lys Leu Lys
            995                 1000                1005

CCT TAC ACT ACT TTG GCT TTA GTA GGC AAG CCT GAA TTA GGT ATT TTA    3852
Pro Tyr Thr Thr Leu Ala Leu Val Gly Lys Pro Glu Leu Gly Ile Leu
        1010                1015                1020

GCT CGT GAT GGC CAA TTT GCA AGA ATG GTG AAT AAA ATA AGA AGT ACC    3900
Ala Arg Asp Gly Gln Phe Ala Arg Met Val Asn Lys Ile Arg Ser Thr
    1025                1030                1035

ACG GAC CTT ATA CCC ATA TTT GCT AAT AAC TTG AAA AGT AGT AAC AAG    3948
Thr Asp Leu Ile Pro Ile Phe Ala Asn Asn Leu Lys Ser Ser Asn Lys
1040                1045                1050                1055

TAT GTC ATA AAC CAA AAT TTA GAC GAT ATA GAG GTA TAT CTT CGG AGA    3996
Tyr Val Ile Asn Gln Asn Leu Asp Asp Ile Glu Val Tyr Leu Arg Arg
                1060                1065                1070

AAG CAG ACA GAA AGA TCG ATT GAT TTT ACA CCA AAG AAG GTT GGG CAA    4044
Lys Gln Thr Glu Arg Ser Ile Asp Phe Thr Pro Lys Lys Val Gly Gln
            1075                1080                1085

ACT TCT GAT ATA ACA TTA GTT TTG GGT GCT TTA TTA GAC ACT TCT CAT    4092
Thr Ser Asp Ile Thr Leu Val Leu Gly Ala Leu Leu Asp Thr Ser His
        1090                1095                1100

AAG TTT AGA AAT TTA GAC AAG GAC CTA TGC GAG AAG TGC GCC AAA TGT    4140
```

|     |     |     |     |     |     |     |     |     |     |     |     |     |     |     |      |
| --- | --- | --- | --- | --- | --- | --- | --- | --- | --- | --- | --- | --- | --- | --- | ---- |
| Lys | Phe | Arg | Asn | Leu | Asp | Lys | Asp | Leu | Cys | Glu | Lys | Cys | Ala | Lys | Cys  |
| 1105 |    |     |     |     | 1110 |   |     |     |     | 1115 |   |     |     |     |      |

| ATC | AGT | ATG | ATT | GGT | GTT | TTA | GAC | GTT | ACA | AAG | CAT | GAG | TTT | AAA | AGA | 4188 |
|---|---|---|---|---|---|---|---|---|---|---|---|---|---|---|---|---|
| Ile | Ser | Met | Ile | Gly | Val | Leu | Asp | Val | Thr | Lys | His | Glu | Phe | Lys | Arg | |
| 1120 | | | | | 1125 | | | | | 1130 | | | | | 1135 | |

| ACA | ACA | TAT | TCA | GAA | AAC | GAA | GTT | TAT | GAT | TTG | AAT | GAT | AGT | GTT | CAA | 4236 |
|---|---|---|---|---|---|---|---|---|---|---|---|---|---|---|---|---|
| Thr | Thr | Tyr | Ser | Glu | Asn | Glu | Val | Tyr | Asp | Leu | Asn | Asp | Ser | Val | Gln | |
| | | | | | 1140 | | | | | 1145 | | | | | 1150 | |

| ACT | ATT | AAG | TTC | TTG | ATA | TGG | GTC | ATA | AAT | GAT | ATC | CTC | GTT | CCT | GCG | 4284 |
|---|---|---|---|---|---|---|---|---|---|---|---|---|---|---|---|---|
| Thr | Ile | Lys | Phe | Leu | Ile | Trp | Val | Ile | Asn | Asp | Ile | Leu | Val | Pro | Ala | |
| | | | 1155 | | | | | 1160 | | | | | 1165 | | | |

| TTT | TGG | CAA | AGT | GAG | AAT | CCC | AGC | AAG | CAA | TTG | TTT | GTT | GCC | CTT | GTC | 4332 |
|---|---|---|---|---|---|---|---|---|---|---|---|---|---|---|---|---|
| Phe | Trp | Gln | Ser | Glu | Asn | Pro | Ser | Lys | Gln | Leu | Phe | Val | Ala | Leu | Val | |
| | | | 1170 | | | | | 1175 | | | | | 1180 | | | |

| ATA | CAG | GAA | TCA | TTA | AAA | TAT | TGC | GGG | CTA | AGT | TCA | GAG | TCA | TGG | GAT | 4380 |
|---|---|---|---|---|---|---|---|---|---|---|---|---|---|---|---|---|
| Ile | Gln | Glu | Ser | Leu | Lys | Tyr | Cys | Gly | Leu | Ser | Ser | Glu | Ser | Trp | Asp | |
| | | 1185 | | | | | 1190 | | | | | 1195 | | | | |

| ATG | AAC | CAT | AAA | GAA | TTA | TAT | CCA | AAT | GAA | GCC | AAA | CTA | TGG | GAA | AAG | 4428 |
|---|---|---|---|---|---|---|---|---|---|---|---|---|---|---|---|---|
| Met | Asn | His | Lys | Glu | Leu | Tyr | Pro | Asn | Glu | Ala | Lys | Leu | Trp | Glu | Lys | |
| 1200 | | | | | 1205 | | | | | 1210 | | | | | 1215 | |

| TTT | AAC | TCT | GTC | TCC | AAG | ACA | ACC | ATC | TAT | CCG | CTT | TTA | TCT | TCC | TTG | 4476 |
|---|---|---|---|---|---|---|---|---|---|---|---|---|---|---|---|---|
| Phe | Asn | Ser | Val | Ser | Lys | Thr | Thr | Ile | Tyr | Pro | Leu | Leu | Ser | Ser | Leu | |
| | | | | 1220 | | | | | 1225 | | | | | 1230 | | |

| TAT | CTT | GCG | CAA | TCA | TGG | AAA | GAA | TAT | GTC | CCG | CTA | AAA | TAT | CCT | TCT | 4524 |
|---|---|---|---|---|---|---|---|---|---|---|---|---|---|---|---|---|
| Tyr | Leu | Ala | Gln | Ser | Trp | Lys | Glu | Tyr | Val | Pro | Leu | Lys | Tyr | Pro | Ser | |
| | | | 1235 | | | | | 1240 | | | | | 1245 | | | |

| AAT | AAC | TTC | AAG | GAA | GGA | TAC | CAA | ATT | TGG | GTG | AAA | AGG | TTT | ACA | TTG | 4572 |
|---|---|---|---|---|---|---|---|---|---|---|---|---|---|---|---|---|
| Asn | Asn | Phe | Lys | Glu | Gly | Tyr | Gln | Ile | Trp | Val | Lys | Arg | Phe | Thr | Leu | |
| | | | 1250 | | | | | 1255 | | | | | 1260 | | | |

| GAT | TTA | TTG | AAA | ACA | GGT | ACA | ACA | GAA | AAT | CAT | CCA | GGA | CAC | GTG | TTT | 4620 |
|---|---|---|---|---|---|---|---|---|---|---|---|---|---|---|---|---|
| Asp | Leu | Leu | Lys | Thr | Gly | Thr | Thr | Glu | Asn | His | Pro | Gly | His | Val | Phe | |
| | | | 1265 | | | | | 1270 | | | | | 1275 | | | |

| TCC | TCT | TTG | ATT | AGG | GAA | GAT | GAT | GGC | TCA | CTA | TCA | AAT | TTT | TTG | CTA | 4668 |
|---|---|---|---|---|---|---|---|---|---|---|---|---|---|---|---|---|
| Ser | Ser | Leu | Ile | Arg | Glu | Asp | Asp | Gly | Ser | Leu | Ser | Asn | Phe | Leu | Leu | |
| 1280 | | | | | 1285 | | | | | 1290 | | | | | 1295 | |

| CCT | TAT | ATT | TCT | CTG | GAC | ATT | ATT | ATC | AAG | GCA | GAA | AAA | GGA | ACT | CCA | 4716 |
|---|---|---|---|---|---|---|---|---|---|---|---|---|---|---|---|---|
| Pro | Tyr | Ile | Ser | Leu | Asp | Ile | Ile | Ile | Lys | Ala | Glu | Lys | Gly | Thr | Pro | |
| | | | | 1300 | | | | | 1305 | | | | | 1310 | | |

| TAC | GCT | GAT | ATT | TTA | AAC | GGG | ATT | ATT | ATT | GAA | TTT | GAC | AGC | ATT | TTC | 4764 |
|---|---|---|---|---|---|---|---|---|---|---|---|---|---|---|---|---|
| Tyr | Ala | Asp | Ile | Leu | Asn | Gly | Ile | Ile | Ile | Glu | Phe | Asp | Ser | Ile | Phe | |
| | | | 1315 | | | | | 1320 | | | | | 1325 | | | |

| ACG | TGC | AAT | CTG | GAA | GGA | ATG | AAT | AAC | TTG | CAA | GTG | GAT | TCG | TTA | AGA | 4812 |
|---|---|---|---|---|---|---|---|---|---|---|---|---|---|---|---|---|
| Thr | Cys | Asn | Leu | Glu | Gly | Met | Asn | Asn | Leu | Gln | Val | Asp | Ser | Leu | Arg | |
| | | 1330 | | | | | 1335 | | | | | 1340 | | | | |

| ATG | TGC | TAT | GAA | TCC | ATC | TTC | AGA | GTT | TTC | GAA | TAT | TGC | AAA | AAA | TGG | 4860 |
|---|---|---|---|---|---|---|---|---|---|---|---|---|---|---|---|---|
| Met | Cys | Tyr | Glu | Ser | Ile | Phe | Arg | Val | Phe | Glu | Tyr | Cys | Lys | Lys | Trp | |
| | | | 1345 | | | | | 1350 | | | | | 1355 | | | |

| GCA | ACT | GAG | TTT | AAA | CAA | AAT | TAC | AGT | AAA | CTA | CAC | GGC | ACT | TTT | ATC | 4908 |
|---|---|---|---|---|---|---|---|---|---|---|---|---|---|---|---|---|
| Ala | Thr | Glu | Phe | Lys | Gln | Asn | Tyr | Ser | Lys | Leu | His | Gly | Thr | Phe | Ile | |
| 1360 | | | | | 1365 | | | | | 1370 | | | | | 1375 | |

| ATT | AAA | GAT | ACG | AAA | ACA | ACT | AAC | ATG | CTT | TTG | AGA | ATA | GAT | GAG | TTT | 4956 |
|---|---|---|---|---|---|---|---|---|---|---|---|---|---|---|---|---|
| Ile | Lys | Asp | Thr | Lys | Thr | Thr | Asn | Met | Leu | Leu | Arg | Ile | Asp | Glu | Phe | |
| | | | | 1380 | | | | | 1385 | | | | | 1390 | | |

| TTG | CGA | ACA | ACC | CCT | TCA | GAT | TTG | CTA | GCT | CAA | CGC | TCC | TTA | GAG | ACG | 5004 |
|---|---|---|---|---|---|---|---|---|---|---|---|---|---|---|---|---|
| Leu | Arg | Thr | Thr | Pro | Ser | Asp | Leu | Leu | Ala | Gln | Arg | Ser | Leu | Glu | Thr | |
| | | | 1395 | | | | | 1400 | | | | | 1405 | | | |

| GAT | TCT | TTT | GAA | AGG | TCT | GCT | CTA | TAC | CTT | GAA | CAG | TGC | TAT | CGA | CAG | 5052 |
|---|---|---|---|---|---|---|---|---|---|---|---|---|---|---|---|---|
| Asp | Ser | Phe | Glu | Arg | Ser | Ala | Leu | Tyr | Leu | Glu | Gln | Cys | Tyr | Arg | Gln | |
| | | | 1410 | | | | | 1415 | | | | | 1420 | | | |

| AAT | CCT | CAC | GAT | AAG | AAC | CAA | AAT | GGA | CAA | CTA | CTG | AAA | AAT | TTA | CAA | 5100 |

|  |  |
|---|---|
| Asn Pro His Asp Lys Asn Gln Asn Gly Gln Leu Leu Lys Asn Leu Gln<br>1425                        1430                       1435 |  |
| ATC ACA TAC GAA GAA ATA GGA GAC ATT GAC TCA CTC GAT GGT GTA CTG<br>Ile Thr Tyr Glu Glu Ile Gly Asp Ile Asp Ser Leu Asp Gly Val Leu<br>1440                       1445                      1450                      1455 | 5148 |
| AGA ACC TTT GCT ACA GGA AAC TTG GTT TCT AAA ATT GAA GAA TTG CAA<br>Arg Thr Phe Ala Thr Gly Asn Leu Val Ser Lys Ile Glu Glu Leu Gln<br>                   1460                      1465                      1470 | 5196 |
| TAT TCT GAA AAC TGG AAA CTC GCA CAA GAC TGC TTT AAT GTC CTC GGC<br>Tyr Ser Glu Asn Trp Lys Leu Ala Gln Asp Cys Phe Asn Val Leu Gly<br>               1475                    1480                    1485 | 5244 |
| AAA TTT TCA GAT GAC CCC AAA ACT ACA ACC AGG ATG CTA AAG TCT ATG<br>Lys Phe Ser Asp Asp Pro Lys Thr Thr Thr Arg Met Leu Lys Ser Met<br>               1490                    1495                    1500 | 5292 |
| TAT GAC CAC CAA TTG TAT TCT CAA ATA ATA TCG AAC TCT TCG TTC CAT<br>Tyr Asp His Gln Leu Tyr Ser Gln Ile Ile Ser Asn Ser Ser Phe His<br>               1505                    1510                    1515 | 5340 |
| TCT TCA GAC GGA AAA ATT TCT TTG TCT CCA GAT GTG AAG GAA TGG TAC<br>Ser Ser Asp Gly Lys Ile Ser Leu Ser Pro Asp Val Lys Glu Trp Tyr<br>1520                        1525                      1530                      1535 | 5388 |
| AGC ATA GGT CTT GAA GCT GCA AAT CTA GAA GGC AAT GTT CAA ACT TTG<br>Ser Ile Gly Leu Glu Ala Ala Asn Leu Glu Gly Asn Val Gln Thr Leu<br>               1540                    1545                    1550 | 5436 |
| AAA AAT TGG GTA GAA CAA ATA GAG AGT TTA AGA AAT ATT GAC GAT AGA<br>Lys Asn Trp Val Glu Gln Ile Glu Ser Leu Arg Asn Ile Asp Asp Arg<br>               1555                    1560                    1565 | 5484 |
| GAA GTA CTT TTG CAG TAC AAT ATT GCG AAA GCT TTA ATT GCC ATC TCA<br>Glu Val Leu Leu Gln Tyr Asn Ile Ala Lys Ala Leu Ile Ala Ile Ser<br>               1570                    1575                    1580 | 5532 |
| AAC GAG GAT CCA TTA AGG ACT CAA AAA TAC ATC CAC AAT TCC TTT AGG<br>Asn Glu Asp Pro Leu Arg Thr Gln Lys Tyr Ile His Asn Ser Phe Arg<br>1585                        1590                      1595 | 5580 |
| CTT ATC GGA ACA AAT TTT ATA ACG TCA TCT AAA GAG ACG ACG CTG CTA<br>Leu Ile Gly Thr Asn Phe Ile Thr Ser Ser Lys Glu Thr Thr Leu Leu<br>1600                        1605                      1610                    1615 | 5628 |
| AAG AAA CAG AAT TTA TTG ATG AAA TTA CAC AGT TTA TAT GAC CTC AGT<br>Lys Lys Gln Asn Leu Leu Met Lys Leu His Ser Leu Tyr Asp Leu Ser<br>               1620                    1625                    1630 | 5676 |
| TTT TTA TCT TCT GCG AAA GAT AAG TTT GAA TAC AAA AGT AAC ACT ACC<br>Phe Leu Ser Ser Ala Lys Asp Lys Phe Glu Tyr Lys Ser Asn Thr Thr<br>                     1635                      1640                    1645 | 5724 |
| ATA CTC GAT TAT CGA ATG GAA CGT ATT GGG GCT GAC TTC GTG CCA AAT<br>Ile Leu Asp Tyr Arg Met Glu Arg Ile Gly Ala Asp Phe Val Pro Asn<br>               1650                    1655                    1660 | 5772 |
| CAT TAC ATA TTG TCA ATG AGA AAG TCA TTT GAC CAA TTG AAA ATG AAT<br>His Tyr Ile Leu Ser Met Arg Lys Ser Phe Asp Gln Leu Lys Met Asn<br>1665                        1670                      1675 | 5820 |
| GAA CAA GCA GAC GCT GAC TTA GGA AAA ACA TTC TTC ACT TTA GCC CAA<br>Glu Gln Ala Asp Ala Asp Leu Gly Lys Thr Phe Phe Thr Leu Ala Gln<br>1680                        1685                      1690                    1695 | 5868 |
| TTG GCG AGA AAC AAC GCT AGG CTA GAT ATA GCC TCC GAA TCA TTA ATG<br>Leu Ala Arg Asn Asn Ala Arg Leu Asp Ile Ala Ser Glu Ser Leu Met<br>                     1700                      1705                    1710 | 5916 |
| CAT TGT TTG GAA AGG CGG TTG CCT CAG GCA GAG TTG GAG TTT GCT GAA<br>His Cys Leu Glu Arg Arg Leu Pro Gln Ala Glu Leu Glu Phe Ala Glu<br>               1715                    1720                    1725 | 5964 |
| ATA CTA TGG AAG CAA GGT GAG AAT GAT AGA GCC TTA AAG ATA GTG CAA<br>Ile Leu Trp Lys Gln Gly Glu Asn Asp Arg Ala Leu Lys Ile Val Gln<br>               1730                    1735                    1740 | 6012 |
| GAA ATA CAT GAA AAG TAT CAA GAA AAT TCC TCG GTT AAT GCT CGC GAT | 6060 |

| | | | | | | | | | | | | | | | |
|---|---|---|---|---|---|---|---|---|---|---|---|---|---|---|---|
| Glu | Ile | His | Glu | Lys | Tyr | Gln | Glu | Asn | Ser | Ser | Val | Asn | Ala | Arg | Asp |
| | 1745 | | | | 1750 | | | | | 1755 | | | | | |

| CGT | GCC | GCC | GTG | CTA | TTA | AAG | TTT | ACT | GAA | TGG | TTA | GAC | CTT | TCG | AAC | 6108 |
|---|---|---|---|---|---|---|---|---|---|---|---|---|---|---|---|---|
| Arg | Ala | Ala | Val | Leu | Leu | Lys | Phe | Thr | Glu | Trp | Leu | Asp | Leu | Ser | Asn | |
| 1760 | | | | | 1765 | | | | | 1770 | | | | | 1775 | |

| AAT | TCA | GCG | TCC | GAA | CAA | ATT | ATT | AAA | CAA | TAT | CAG | GAT | ATT | TTT | CAG | 6156 |
|---|---|---|---|---|---|---|---|---|---|---|---|---|---|---|---|---|
| Asn | Ser | Ala | Ser | Glu | Gln | Ile | Ile | Lys | Gln | Tyr | Gln | Asp | Ile | Phe | Gln | |
| | | | | 1780 | | | | | 1785 | | | | | 1790 | | |

| ATT | GAT | TCT | AAA | TGG | GAT | AAA | CCA | TAT | TAC | TCT | ATT | GGC | TTA | TAC | TAT | 6204 |
|---|---|---|---|---|---|---|---|---|---|---|---|---|---|---|---|---|
| Ile | Asp | Ser | Lys | Trp | Asp | Lys | Pro | Tyr | Tyr | Ser | Ile | Gly | Leu | Tyr | Tyr | |
| | | | 1795 | | | | | 1800 | | | | | 1805 | | | |

| AGT | AGA | CTA | CTT | GAG | CGC | AAA | AAA | GCA | GAG | GGT | TAT | ATT | ACT | AAT | GGT | 6252 |
|---|---|---|---|---|---|---|---|---|---|---|---|---|---|---|---|---|
| Ser | Arg | Leu | Leu | Glu | Arg | Lys | Lys | Ala | Glu | Gly | Tyr | Ile | Thr | Asn | Gly | |
| | | 1810 | | | | | 1815 | | | | | 1820 | | | | |

| CGT | TTT | GAG | TAC | AGG | GCA | ATA | TCT | TAC | TTT | TTA | TTG | GCA | TTT | GAA | AAG | 6300 |
|---|---|---|---|---|---|---|---|---|---|---|---|---|---|---|---|---|
| Arg | Phe | Glu | Tyr | Arg | Ala | Ile | Ser | Tyr | Phe | Leu | Leu | Ala | Phe | Glu | Lys | |
| | 1825 | | | | | 1830 | | | | | 1835 | | | | | |

| AAC | ACT | GCT | AAA | GTA | AGA | GAA | AAT | TTG | CCC | AAA | GTT | ATC | ACG | TTT | TGG | 6348 |
|---|---|---|---|---|---|---|---|---|---|---|---|---|---|---|---|---|
| Asn | Thr | Ala | Lys | Val | Arg | Glu | Asn | Leu | Pro | Lys | Val | Ile | Thr | Phe | Trp | |
| 1840 | | | | | 1845 | | | | | 1850 | | | | | 1855 | |

| CTA | GAT | ATT | GCG | GCC | GCA | TCA | ATT | TCT | GAA | GCT | CCT | GGA | AAC | AGG | AAG | 6396 |
|---|---|---|---|---|---|---|---|---|---|---|---|---|---|---|---|---|
| Leu | Asp | Ile | Ala | Ala | Ala | Ser | Ile | Ser | Glu | Ala | Pro | Gly | Asn | Arg | Lys | |
| | | | | 1860 | | | | | 1865 | | | | | 1870 | | |

| GAA | ATG | CTG | AGT | AAG | GCT | ACG | GAA | GAT | ATA | TGT | AGT | CAT | GTT | GAA | GAA | 6444 |
|---|---|---|---|---|---|---|---|---|---|---|---|---|---|---|---|---|
| Glu | Met | Leu | Ser | Lys | Ala | Thr | Glu | Asp | Ile | Cys | Ser | His | Val | Glu | Glu | |
| | | | 1875 | | | | | 1880 | | | | | 1885 | | | |

| GCG | CTG | CAG | CAT | TGT | CCC | ACT | TAT | ATT | TGG | TAC | TTT | GTT | TTG | ACT | CAG | 6492 |
|---|---|---|---|---|---|---|---|---|---|---|---|---|---|---|---|---|
| Ala | Leu | Gln | His | Cys | Pro | Thr | Tyr | Ile | Trp | Tyr | Phe | Val | Leu | Thr | Gln | |
| | | 1890 | | | | | 1895 | | | | | 1900 | | | | |

| TTG | TTA | TCT | AGG | TTA | TTA | CAT | TCT | CAT | CAA | TCA | TCG | GCC | CAG | ATA | ATA | 6540 |
|---|---|---|---|---|---|---|---|---|---|---|---|---|---|---|---|---|
| Leu | Leu | Ser | Arg | Leu | Leu | His | Ser | His | Gln | Ser | Ser | Ala | Gln | Ile | Ile | |
| | 1905 | | | | | 1910 | | | | | 1915 | | | | | |

| ATG | CAC | ATA | CTG | CTA | AGT | TTG | GCT | GTT | GAA | TAC | CCC | TCT | CAT | ATT | TTA | 6588 |
|---|---|---|---|---|---|---|---|---|---|---|---|---|---|---|---|---|
| Met | His | Ile | Leu | Leu | Ser | Leu | Ala | Val | Glu | Tyr | Pro | Ser | His | Ile | Leu | |
| 1920 | | | | | 1925 | | | | | 1930 | | | | | 1935 | |

| TGG | TAT | ATC | ACA | GCC | CTT | GTA | AAT | TCC | AAT | TCT | TCA | AAA | AGA | GTT | CTT | 6636 |
|---|---|---|---|---|---|---|---|---|---|---|---|---|---|---|---|---|
| Trp | Tyr | Ile | Thr | Ala | Leu | Val | Asn | Ser | Asn | Ser | Ser | Lys | Arg | Val | Leu | |
| | | | | 1940 | | | | | 1945 | | | | | 1950 | | |

| CGT | GGT | AAG | CAT | ATT | TTA | GAA | AAG | TAT | AGA | CAA | CAT | TCG | CAA | AAT | CCT | 6684 |
|---|---|---|---|---|---|---|---|---|---|---|---|---|---|---|---|---|
| Arg | Gly | Lys | His | Ile | Leu | Glu | Lys | Tyr | Arg | Gln | His | Ser | Gln | Asn | Pro | |
| | | | 1955 | | | | | 1960 | | | | | 1965 | | | |

| CAT | GAT | CTA | GTT | TCT | AGT | GCA | TTG | GAT | TTA | ACG | AAA | GCA | TTA | ACT | CGT | 6732 |
|---|---|---|---|---|---|---|---|---|---|---|---|---|---|---|---|---|
| His | Asp | Leu | Val | Ser | Ser | Ala | Leu | Asp | Leu | Thr | Lys | Ala | Leu | Thr | Arg | |
| | | 1970 | | | | | 1975 | | | | | 1980 | | | | |

| GTC | TGT | TTG | CAA | GAT | GTC | AAA | AGC | ATT | ACA | AGT | AGA | TCA | GGC | AAA | TCT | 6780 |
|---|---|---|---|---|---|---|---|---|---|---|---|---|---|---|---|---|
| Val | Cys | Leu | Gln | Asp | Val | Lys | Ser | Ile | Thr | Ser | Arg | Ser | Gly | Lys | Ser | |
| | 1985 | | | | | 1990 | | | | | 1995 | | | | | |

| TTA | GAA | AAA | GAC | TTC | AAA | TTT | GAC | ATG | AAC | GTG | GCC | CCA | TCT | GCA | ATG | 6828 |
|---|---|---|---|---|---|---|---|---|---|---|---|---|---|---|---|---|
| Leu | Glu | Lys | Asp | Phe | Lys | Phe | Asp | Met | Asn | Val | Ala | Pro | Ser | Ala | Met | |
| 2000 | | | | | 2005 | | | | | 2010 | | | | | 2015 | |

| GTT | GTT | CCA | GTA | AGA | AAA | AAT | TTA | GAC | ATC | ATT | TCA | CCA | CTA | GAG | TCT | 6876 |
|---|---|---|---|---|---|---|---|---|---|---|---|---|---|---|---|---|
| Val | Val | Pro | Val | Arg | Lys | Asn | Leu | Asp | Ile | Ile | Ser | Pro | Leu | Glu | Ser | |
| | | | | 2020 | | | | | 2025 | | | | | 2030 | | |

| AAC | TCA | ATG | AGG | GGC | TAT | CAA | CCA | TTT | AGG | CCG | GTT | GTT | TCT | ATA | ATT | 6924 |
|---|---|---|---|---|---|---|---|---|---|---|---|---|---|---|---|---|
| Asn | Ser | Met | Arg | Gly | Tyr | Gln | Pro | Phe | Arg | Pro | Val | Val | Ser | Ile | Ile | |
| | | | 2035 | | | | | 2040 | | | | | 2045 | | | |

| AGA | TTC | GGA | TCA | TCT | TAT | AAA | GTG | TTT | TCT | TCA | TTA | AAG | AAG | CCA | AAA | 6972 |
|---|---|---|---|---|---|---|---|---|---|---|---|---|---|---|---|---|
| Arg | Phe | Gly | Ser | Ser | Tyr | Lys | Val | Phe | Ser | Ser | Leu | Lys | Lys | Pro | Lys | |
| | | 2050 | | | | | 2055 | | | | | 2060 | | | | |

| CAA | TTG | AAC | ATA | ATA | GGT | TCA | GAT | GGC | AAC | ATT | TAT | GGG | ATC | ATG | TGT | 7020 |

```
Gln Leu Asn Ile Ile Gly Ser Asp Gly Asn Ile Tyr Gly Ile Met Cys
    2065                2070                    2075

AAG AAG GAA GAT GTC CGA CAA GAT AAC CAA TAT ATG CAG TTC GCC ACA        7068
Lys Lys Glu Asp Val Arg Gln Asp Asn Gln Tyr Met Gln Phe Ala Thr
2080                2085                    2090                2095

ACA ATG GAT TTT CTT CTG AGT AAG GAC ATA GCT TCA AGA AAA AGA AGC        7116
Thr Met Asp Phe Leu Leu Ser Lys Asp Ile Ala Ser Arg Lys Arg Ser
                2100                    2105                2110

CTG GGC ATA AAT ATT TAC TAC CGT ACT ATC TCT TCG AGA AGA CTG TGG        7164
Leu Gly Ile Asn Ile Tyr Tyr Arg Thr Ile Ser Ser Arg Arg Leu Trp
            2115                    2120                2125

GAT ATT GGA AAT GGT ACC GAA TGT TGT AAC TTT AAG ATC TAT TCT TTC        7212
Asp Ile Gly Asn Gly Thr Glu Cys Cys Asn Phe Lys Ile Tyr Ser Phe
        2130                    2135                2140

TAC AAG TAC GAA AGT CTG AAA ATT AAG TAT AGC CTG AAA AGT CTA CAT        7260
Tyr Lys Tyr Glu Ser Leu Lys Ile Lys Tyr Ser Leu Lys Ser Leu His
    2145                    2150                2155

GAT AGG TGG CAG CAC ACC GCA GTA GAT GGA AAA CTC GAG TTT TAC ATG        7308
Asp Arg Trp Gln His Thr Ala Val Asp Gly Lys Leu Glu Phe Tyr Met
2160                    2165                2170                2175

GAA CAG GTA GAT AAA TTT CCT CCA ATC TTG TAC CAA TGG TTT TTA GAA        7356
Glu Gln Val Asp Lys Phe Pro Pro Ile Leu Tyr Gln Trp Phe Leu Glu
                2180                    2185                2190

AAC TTT CCT GAT CCA ATC AAT TGG TTC AAC GCC AGG AAT ACG TAT GCC        7404
Asn Phe Pro Asp Pro Ile Asn Trp Phe Asn Ala Arg Asn Thr Tyr Ala
            2195                    2200                2205

AGA TCT TAC GCC GTC ATG GCA ATG GTT GGC CAT ATA TTA GGT CTA GGT        7452
Arg Ser Tyr Ala Val Met Ala Met Val Gly His Ile Leu Gly Leu Gly
        2210                    2215                    2220

GAT AGG CAC TGT GAA AAC ATA TTA CTA GAT ATA CAG ACG GGT AAA GTT        7500
Asp Arg His Cys Glu Asn Ile Leu Leu Asp Ile Gln Thr Gly Lys Val
    2225                    2230                    2235

CTT CAT GTA GAC TTC GAC TGT TTA TTT GAG AAA GGC AAA AGG TTA CCT        7548
Leu His Val Asp Phe Asp Cys Leu Phe Glu Lys Gly Lys Arg Leu Pro
2240                    2245                    2250                2255

GTC CCA GAA ATT GTT CCC TTC AGA CTA ACA CCA AAT TTA TTG GAT GCG        7596
Val Pro Glu Ile Val Pro Phe Arg Leu Thr Pro Asn Leu Leu Asp Ala
                2260                    2265                2270

TTG GGC ATA ATT GGG ACA GAA GGA ACA TTT AAG AAG TCT AGT GAA GTC        7644
Leu Gly Ile Ile Gly Thr Glu Gly Thr Phe Lys Lys Ser Ser Glu Val
            2275                    2280                2285

ACG TTG GCT TTA ATG AGA AAA AAT GAA GTA GCG TTG ATG AAT GTG ATC        7692
Thr Leu Ala Leu Met Arg Lys Asn Glu Val Ala Leu Met Asn Val Ile
        2290                    2295                2300

GAA ACA ATT ATG TAC GAT AGA AAC ATG GAC CAC TCA ATT CAA AAA GCG        7740
Glu Thr Ile Met Tyr Asp Arg Asn Met Asp His Ser Ile Gln Lys Ala
    2305                    2310                    2315

CTA AAG GTC TTA AGA AAC AAA ATC CGC GGT ATA GAT CCG CAG GAT GGC        7788
Leu Lys Val Leu Arg Asn Lys Ile Arg Gly Ile Asp Pro Gln Asp Gly
2320                    2325                    2330                2335

CTG GTA TTG AGT GTT GCT GGC CAA ACA GAA ACA TTG ATC CAA GAA GCA        7836
Leu Val Leu Ser Val Ala Gly Gln Thr Glu Thr Leu Ile Gln Glu Ala
                2340                    2345                2350

ACA TCA GAA GAC AAT CTA AGC AAG ATG TAT ATT GGT TGG CTT CCA TTT        7884
Thr Ser Glu Asp Asn Leu Ser Lys Met Tyr Ile Gly Trp Leu Pro Phe
            2355                    2360                2365

TGG TAACGACTTT CCACCATTTT CGGCAACAGA CGAACTTCCT CTTGATCTAA             7937
Trp

CCATCACTGC AGGTGCTTTT CTCCGGCGGA GTTAATAGAT ACTTATCCCC GCTTCATGTC      7997
```

| ATACTATCTC | TCTTAACAGG | GATGTTGACA | CCATATAAGT | TAACATAACA | TATACGTACG | 8057 |
| TAATAATATT | AAGGACTATC | TCCGATTTCA | AAAGAGAAAC | AACCTAATCA | AGCCTTATTA | 8117 |
| TAAGAGCAAA | TTATTCAAAA | AAAGTCTACG | GAGAAAATTA | TTATGGTGGT | TTTAGACAAG | 8177 |
| AAGTTATTGG | AAAGATTGAC | TTCTCGTAAG | GTTCCTTAGA | AGAGCTCGAA | GATATGGAAA | 8237 |
| ACGATGCTTG | TTGTCTACTT | TACATAACAA | GATGCCTTGA | TTGGGACTTA | CATAAGAAAT | 8297 |
| GCGTTAAGAA | TTTCCCGAAC | AGTTGCATGT | ATATCTCTTC | CAAATGGCTC | GTGT | 8351 |

( 2 ) INFORMATION FOR SEQ ID NO:15:

( i ) SEQUENCE CHARACTERISTICS:
        ( A ) LENGTH: 2368 amino acids
        ( B ) TYPE: amino acid
        ( D ) TOPOLOGY: linear ( i i ) MOLECULE TYPE: protein
        ( A ) DESCRIPTION: yeast MEC1 protein ( x i ) SEQUENCE DESCRIPTION: SEQ ID NO:15:

```
Met Glu Ser His Val Lys Tyr Leu Asp Glu Leu Ile Leu Ala Ile Lys
  1               5                  10                  15

Asp Leu Asn Ser Gly Val Asp Ser Lys Val Gln Ile Lys Lys Val Pro
             20                  25                  30

Thr Asp Pro Ser Ser Ser Gln Glu Tyr Ala Lys Ser Leu Lys Ile Leu
         35                  40                  45

Asn Thr Leu Ile Arg Asn Leu Lys Asp Gln Arg Arg Asn Asn Ile Met
     50                  55                  60

Lys Asn Asp Thr Ile Phe Ser Lys Thr Val Ser Ala Leu Ala Leu Leu
 65                  70                  75                  80

Leu Glu Tyr Asn Pro Phe Leu Leu Val Met Lys Asp Ser Asn Gly Asn
                 85                  90                  95

Phe Glu Ile Gln Arg Leu Ile Asp Asp Phe Leu Asn Ile Ser Val Leu
                100                 105                 110

Asn Tyr Asp Asn Tyr His Arg Ile Trp Phe Met Arg Arg Lys Leu Gly
            115                 120                 125

Ser Trp Cys Lys Ala Cys Val Glu Phe Tyr Gly Lys Pro Ala Lys Phe
        130                 135                 140

Gln Leu Thr Ala His Phe Glu Asn Thr Met Asn Leu Tyr Glu Gln Ala
145                 150                 155                 160

Leu Thr Glu Val Leu Leu Gly Lys Thr Glu Leu Leu Lys Phe Tyr Asp
                165                 170                 175

Thr Leu Lys Gly Leu Tyr Ile Leu Leu Tyr Trp Phe Thr Ser Glu Tyr
            180                 185                 190

Ser Thr Phe Gly Asn Ser Ile Ala Phe Leu Asp Ser Ser Leu Gly Phe
        195                 200                 205

Thr Lys Phe Asp Phe Asn Phe Gln Arg Leu Ile Arg Ile Val Leu Tyr
    210                 215                 220

Val Phe Asp Ser Cys Glu Leu Ala Ala Leu Glu Tyr Ala Glu Ile Gln
225                 230                 235                 240

Leu Lys Tyr Ile Ser Leu Val Val Asp Tyr Val Cys Asn Arg Thr Ile
                245                 250                 255

Ser Thr Ala Leu Asp Ala Pro Ala Leu Val Cys Cys Glu Gln Leu Lys
            260                 265                 270

Phe Val Leu Thr Thr Met His His Phe Leu Asp Asn Lys Tyr Gly Leu
        275                 280                 285

Leu Asp Asn Asp Pro Thr Met Ala Lys Gly Ile Leu Arg Leu Tyr Ser
```

```
              290                      295                      300
Leu  Cys  Ile  Ser  Asn  Asp  Phe  Ser  Lys  Cys  Phe  Val  Asp  His  Phe  Pro
305                      310                      315                      320

Ile  Asp  Gln  Trp  Ala  Asp  Phe  Ser  Gln  Ser  Glu  His  Phe  Pro  Phe  Thr
                    325                      330                      335

Gln  Leu  Thr  Asn  Lys  Ala  Leu  Ser  Ile  Val  Tyr  Phe  Asp  Leu  Lys  Arg
               340                      345                      350

Arg  Ser  Leu  Pro  Val  Glu  Ala  Leu  Lys  Tyr  Asp  Asn  Lys  Phe  Asn  Ile
          355                      360                      365

Trp  Val  Tyr  Gln  Ser  Glu  Pro  Asp  Ser  Ser  Leu  Lys  Asn  Val  Thr  Ser
     370                      375                      380

Pro  Phe  Asp  Asp  Arg  Tyr  Lys  Gln  Leu  Glu  Lys  Leu  Arg  Leu  Leu  Val
385                      390                      395                      400

Leu  Lys  Lys  Phe  Asn  Lys  Thr  Glu  Arg  Gly  Thr  Leu  Leu  Lys  Tyr  Arg
                    405                      410                      415

Val  Asn  Gln  Leu  Ser  Pro  Gly  Phe  Phe  Gln  Arg  Ala  Gly  Asn  Asp  Phe
               420                      425                      430

Lys  Leu  Ile  Leu  Asn  Glu  Ala  Ser  Val  Ser  Ile  Gln  Thr  Cys  Phe  Lys
          435                      440                      445

Thr  Asn  Asn  Ile  Thr  Arg  Leu  Thr  Ser  Trp  Thr  Val  Ile  Leu  Gly  Arg
     450                      455                      460

Leu  Ala  Cys  Leu  Glu  Ser  Glu  Lys  Phe  Ser  Gly  Thr  Leu  Pro  Asn  Ser
465                      470                      475                      480

Thr  Lys  Asp  Met  Asp  Asn  Trp  Tyr  Val  Cys  His  Leu  Cys  Asp  Ile  Glu
                    485                      490                      495

Lys  Thr  Gly  Asn  Pro  Phe  Val  Arg  Ile  Asn  Pro  Asn  Arg  Pro  Glu  Ala
               500                      505                      510

Ala  Gly  Lys  Ser  Glu  Ile  Phe  Arg  Ile  Leu  His  Ser  Asn  Phe  Leu  Ser
          515                      520                      525

His  Pro  Asn  Ile  Asp  Glu  Phe  Ser  Glu  Ser  Leu  Leu  Ser  Gly  Ile  Leu
     530                      535                      540

Phe  Ser  Leu  His  Arg  Ile  Phe  Ser  His  Phe  Gln  Pro  Pro  Lys  Leu  Thr
545                      550                      555                      560

Asp  Gly  Asn  Gly  Gln  Ile  Asn  Lys  Ser  Phe  Lys  Leu  Val  Gln  Lys  Cys
                    565                      570                      575

Phe  Met  Asn  Ser  Asn  Arg  Tyr  Leu  Arg  Leu  Leu  Ser  Thr  Arg  Ile  Ile
               580                      585                      590

Pro  Leu  Phe  Asn  Ile  Ser  Asp  Ser  His  Asn  Ser  Glu  Asp  Glu  His  Thr
          595                      600                      605

Ala  Thr  Leu  Ile  Lys  Phe  Leu  Gln  Ser  Gln  Lys  Leu  Pro  Val  Val  Lys
     610                      615                      620

Glu  Asn  Leu  Val  Ile  Ala  Trp  Thr  Gln  Leu  Thr  Leu  Thr  Thr  Ser  Asn
625                      630                      635                      640

Asp  Val  Phe  Asp  Thr  Leu  Leu  Leu  Lys  Leu  Ile  Asp  Ile  Phe  Asn  Ser
                    645                      650                      655

Asp  Asp  Tyr  Ser  Leu  Arg  Ile  Met  Met  Thr  Leu  Gln  Ile  Lys  Asn  Met
               660                      665                      670

Ala  Lys  Ile  Leu  Lys  Lys  Thr  Pro  Tyr  Gln  Leu  Leu  Ser  Pro  Ile  Leu
          675                      680                      685

Pro  Val  Leu  Leu  Arg  Gln  Leu  Gly  Lys  Asn  Leu  Val  Glu  Arg  Lys  Val
     690                      695                      700

Gly  Phe  Gln  Asn  Leu  Ile  Glu  Leu  Leu  Gly  Tyr  Pro  Ser  Lys  Thr  Ile
705                      710                      715                      720
```

-continued

```
Leu Asp Ile Phe Gln Arg Tyr Ile Ile Pro Tyr Ala Ile Ile Gln Tyr
            725             730                  735

Lys Ser Asp Val Leu Ser Glu Ile Ala Lys Ile Met Cys Asp Gly Asp
            740             745             750

Thr Ser Leu Ile Asn Gln Met Lys Val Asn Leu Leu Lys Lys Asn Ser
            755             760             765

Arg Gln Ile Phe Ala Val Ala Leu Val Lys His Gly Leu Phe Ser Leu
            770             775             780

Asp Ile Leu Glu Thr Leu Phe Leu Asn Arg Ala Pro Thr Phe Asp Lys
785             790             795                             800

Gly Tyr Ile Thr Ala Tyr Leu Pro Asp Tyr Lys Thr Leu Ala Glu Ile
                805             810                  815

Thr Lys Leu Tyr Lys Asn Ser Val Thr Lys Asp Ala Ser Asp Ser Glu
            820             825             830

Asn Ala Asn Met Ile Leu Cys Ser Leu Arg Phe Leu Ile Thr Asn Phe
            835             840             845

Glu Lys Asp Lys Arg His Gly Ser Lys Tyr Lys Asn Ile Asn Asn Trp
    850             855             860

Thr Asp Asp Gln Glu Gln Ala Phe Gln Lys Lys Leu Gln Asp Asn Ile
865             870             875                             880

Leu Gly Ile Phe Gln Val Phe Ser Ser Asp Ile His Asp Val Glu Gly
            885             890             895

Arg Thr Thr Tyr Tyr Glu Lys Leu Arg Val Ile Asn Gly Ile Ser Phe
            900             905             910

Leu Ile Ile Tyr Ala Pro Lys Lys Ser Ile Ile Ser Ala Leu Ala Gln
            915             920             925

Ile Ser Ile Cys Leu Gln Thr Gly Leu Gly Leu Lys Glu Val Arg Tyr
    930             935             940

Glu Ala Phe Arg Cys Trp His Leu Leu Val Arg His Leu Asn Asp Glu
945             950             955                             960

Glu Leu Ser Thr Val Ile Asp Ser Leu Ile Ala Phe Ile Leu Gln Lys
            965             970             975

Trp Ser Glu Phe Asn Gly Lys Leu Arg Asn Ile Val Tyr Ser Ile Leu
            980             985             990

Asp Thr Leu Ile Lys Glu Lys Ser Asp Leu Ile Leu Lys Leu Lys Pro
            995             1000            1005

Tyr Thr Thr Leu Ala Leu Val Gly Lys Pro Glu Leu Gly Ile Leu Ala
    1010            1015            1020

Arg Asp Gly Gln Phe Ala Arg Met Val Asn Lys Ile Arg Ser Thr Thr
1025            1030            1035            1040

Asp Leu Ile Pro Ile Phe Ala Asn Asn Leu Lys Ser Ser Asn Lys Tyr
                1045            1050            1055

Val Ile Asn Gln Asn Leu Asp Asp Ile Glu Val Tyr Leu Arg Arg Lys
            1060            1065            1070

Gln Thr Glu Arg Ser Ile Asp Phe Thr Pro Lys Lys Val Gly Gln Thr
    1075            1080            1085

Ser Asp Ile Thr Leu Val Leu Gly Ala Leu Leu Asp Thr Ser His Lys
    1090            1095            1100

Phe Arg Asn Leu Asp Lys Asp Leu Cys Glu Lys Cys Ala Lys Cys Ile
1105            1110            1115            1120

Ser Met Ile Gly Val Leu Asp Val Thr Lys His Glu Phe Lys Arg Thr
            1125            1130            1135

Thr Tyr Ser Glu Asn Glu Val Tyr Asp Leu Asn Asp Ser Val Gln Thr
            1140            1145            1150
```

```
Ile Lys Phe Leu Ile Trp Val Ile Asn Asp Ile Leu Val Pro Ala Phe
        1155                1160                1165
Trp Gln Ser Glu Asn Pro Ser Lys Gln Leu Phe Val Ala Leu Val Ile
    1170                1175                1180
Gln Glu Ser Leu Lys Tyr Cys Gly Leu Ser Ser Glu Ser Trp Asp Met
1185                1190                1195                1200
Asn His Lys Glu Leu Tyr Pro Asn Glu Ala Lys Leu Trp Glu Lys Phe
                1205                1210                1215
Asn Ser Val Ser Lys Thr Thr Ile Tyr Pro Leu Leu Ser Ser Leu Tyr
            1220                1225                1230
Leu Ala Gln Ser Trp Lys Glu Tyr Val Pro Leu Lys Tyr Pro Ser Asn
            1235                1240                1245
Asn Phe Lys Glu Gly Tyr Gln Ile Trp Val Lys Arg Phe Thr Leu Asp
            1250                1255                1260
Leu Leu Lys Thr Gly Thr Thr Glu Asn His Pro Gly His Val Phe Ser
1265                1270                1275                1280
Ser Leu Ile Arg Glu Asp Asp Gly Ser Leu Ser Asn Phe Leu Leu Pro
                1285                1290                1295
Tyr Ile Ser Leu Asp Ile Ile Ile Lys Ala Glu Lys Gly Thr Pro Tyr
            1300                1305                1310
Ala Asp Ile Leu Asn Gly Ile Ile Ile Glu Phe Asp Ser Ile Phe Thr
            1315                1320                1325
Cys Asn Leu Glu Gly Met Asn Asn Leu Gln Val Asp Ser Leu Arg Met
        1330                1335                1340
Cys Tyr Glu Ser Ile Phe Arg Val Phe Glu Tyr Cys Lys Lys Trp Ala
1345                1350                1355                1360
Thr Glu Phe Lys Gln Asn Tyr Ser Lys Leu His Gly Thr Phe Ile Ile
            1365                1370                1375
Lys Asp Thr Lys Thr Thr Asn Met Leu Leu Arg Ile Asp Glu Phe Leu
        1380                1385                1390
Arg Thr Thr Pro Ser Asp Leu Leu Ala Gln Arg Ser Leu Glu Thr Asp
        1395                1400                1405
Ser Phe Glu Arg Ser Ala Leu Tyr Leu Glu Gln Cys Tyr Arg Gln Asn
        1410                1415                1420
Pro His Asp Lys Asn Gln Asn Gly Gln Leu Leu Lys Asn Leu Gln Ile
1425                1430                1435                1440
Thr Tyr Glu Glu Ile Gly Asp Ile Asp Ser Leu Asp Gly Val Leu Arg
                1445                1450                1455
Thr Phe Ala Thr Gly Asn Leu Val Ser Lys Ile Glu Glu Leu Gln Tyr
            1460                1465                1470
Ser Glu Asn Trp Lys Leu Ala Gln Asp Cys Phe Asn Val Leu Gly Lys
            1475                1480                1485
Phe Ser Asp Asp Pro Lys Thr Thr Arg Met Leu Lys Ser Met Tyr
            1490                1495                1500
Asp His Gln Leu Tyr Ser Gln Ile Ile Ser Asn Ser Ser Phe His Ser
1505                1510                1515                1520
Ser Asp Gly Lys Ile Ser Leu Ser Pro Asp Val Lys Glu Trp Tyr Ser
                1525                1530                1535
Ile Gly Leu Glu Ala Ala Asn Leu Glu Gly Asn Val Gln Thr Leu Lys
            1540                1545                1550
Asn Trp Val Glu Gln Ile Glu Ser Leu Arg Asn Ile Asp Asp Arg Glu
            1555                1560                1565
Val Leu Leu Gln Tyr Asn Ile Ala Lys Ala Leu Ile Ala Ile Ser Asn
```

```
                    1570                      1575                      1580
Glu Asp Pro Leu Arg Thr Gln Lys Tyr Ile His Asn Ser Phe Arg Leu
1585                      1590                      1595                      1600

Ile Gly Thr Asn Phe Ile Thr Ser Ser Lys Glu Thr Thr Leu Leu Lys
                    1605                      1610                      1615

Lys Gln Asn Leu Leu Met Lys Leu His Ser Leu Tyr Asp Leu Ser Phe
                    1620                      1625                      1630

Leu Ser Ser Ala Lys Asp Lys Phe Glu Tyr Lys Ser Asn Thr Thr Ile
                    1635                      1640                      1645

Leu Asp Tyr Arg Met Glu Arg Ile Gly Ala Asp Phe Val Pro Asn His
                    1650                      1655                      1660

Tyr Ile Leu Ser Met Arg Lys Ser Phe Asp Gln Leu Lys Met Asn Glu
1665                      1670                      1675                      1680

Gln Ala Asp Ala Asp Leu Gly Lys Thr Phe Phe Thr Leu Ala Gln Leu
                    1685                      1690                      1695

Ala Arg Asn Asn Ala Arg Leu Asp Ile Ala Ser Glu Ser Leu Met His
                    1700                      1705                      1710

Cys Leu Glu Arg Arg Leu Pro Gln Ala Glu Leu Glu Phe Ala Glu Ile
                    1715                      1720                      1725

Leu Trp Lys Gln Gly Glu Asn Asp Arg Ala Leu Lys Ile Val Gln Glu
                    1730                      1735                      1740

Ile His Glu Lys Tyr Gln Glu Asn Ser Ser Val Asn Ala Arg Asp Arg
1745                      1750                      1755                      1760

Ala Ala Val Leu Leu Lys Phe Thr Glu Trp Leu Asp Leu Ser Asn Asn
                    1765                      1770                      1775

Ser Ala Ser Glu Gln Ile Ile Lys Gln Tyr Gln Asp Ile Phe Gln Ile
                    1780                      1785                      1790

Asp Ser Lys Trp Asp Lys Pro Tyr Tyr Ser Ile Gly Leu Tyr Tyr Ser
                    1795                      1800                      1805

Arg Leu Leu Glu Arg Lys Lys Ala Glu Gly Tyr Ile Thr Asn Gly Arg
                    1810                      1815                      1820

Phe Glu Tyr Arg Ala Ile Ser Tyr Phe Leu Leu Ala Phe Glu Lys Asn
1825                      1830                      1835                      1840

Thr Ala Lys Val Arg Glu Asn Leu Pro Lys Val Ile Thr Phe Trp Leu
                    1845                      1850                      1855

Asp Ile Ala Ala Ala Ser Ile Ser Glu Ala Pro Gly Asn Arg Lys Glu
                    1860                      1865                      1870

Met Leu Ser Lys Ala Thr Glu Asp Ile Cys Ser His Val Glu Glu Ala
                    1875                      1880                      1885

Leu Gln His Cys Pro Thr Tyr Ile Trp Tyr Phe Val Leu Thr Gln Leu
                    1890                      1895                      1900

Leu Ser Arg Leu Leu His Ser His Gln Ser Ser Ala Gln Ile Ile Met
1905                      1910                      1915                      1920

His Ile Leu Leu Ser Leu Ala Val Glu Tyr Pro Ser His Ile Leu Trp
                    1925                      1930                      1935

Tyr Ile Thr Ala Leu Val Asn Ser Asn Ser Ser Lys Arg Val Leu Arg
                    1940                      1945                      1950

Gly Lys His Ile Leu Glu Lys Tyr Arg Gln His Ser Gln Asn Pro His
                    1955                      1960                      1965

Asp Leu Val Ser Ser Ala Leu Asp Leu Thr Lys Ala Leu Thr Arg Val
                    1970                      1975                      1980

Cys Leu Gln Asp Val Lys Ser Ile Thr Ser Arg Ser Gly Lys Ser Leu
1985                      1990                      1995                      2000
```

| Glu | Lys | Asp | Phe | Lys | Phe | Asp | Met | Asn | Val | Ala | Pro | Ser | Ala | Met | Val |
|---|---|---|---|---|---|---|---|---|---|---|---|---|---|---|---|
| | | | | 2005 | | | | 2010 | | | | | | 2015 | |

| Val | Pro | Val | Arg | Lys | Asn | Leu | Asp | Ile | Ile | Ser | Pro | Leu | Glu | Ser | Asn |
|---|---|---|---|---|---|---|---|---|---|---|---|---|---|---|---|
| | | | | 2020 | | | | 2025 | | | | 2030 | | | |

| Ser | Met | Arg | Gly | Tyr | Gln | Pro | Phe | Arg | Pro | Val | Val | Ser | Ile | Ile | Arg |
|---|---|---|---|---|---|---|---|---|---|---|---|---|---|---|---|
| | | | 2035 | | | | 2040 | | | | | 2045 | | | |

| Phe | Gly | Ser | Ser | Tyr | Lys | Val | Phe | Ser | Ser | Leu | Lys | Lys | Pro | Lys | Gln |
|---|---|---|---|---|---|---|---|---|---|---|---|---|---|---|---|
| | | 2050 | | | | | 2055 | | | | | 2060 | | | |

| Leu | Asn | Ile | Ile | Gly | Ser | Asp | Gly | Asn | Ile | Tyr | Gly | Ile | Met | Cys | Lys |
|---|---|---|---|---|---|---|---|---|---|---|---|---|---|---|---|
| 2065 | | | | | 2070 | | | | 2075 | | | | | 2080 | |

| Lys | Glu | Asp | Val | Arg | Gln | Asp | Asn | Gln | Tyr | Met | Gln | Phe | Ala | Thr | Thr |
|---|---|---|---|---|---|---|---|---|---|---|---|---|---|---|---|
| | | | | 2085 | | | | 2090 | | | | | 2095 | | |

| Met | Asp | Phe | Leu | Leu | Ser | Lys | Asp | Ile | Ala | Ser | Arg | Lys | Arg | Ser | Leu |
|---|---|---|---|---|---|---|---|---|---|---|---|---|---|---|---|
| | | | 2100 | | | | | 2105 | | | | 2110 | | | |

| Gly | Ile | Asn | Ile | Tyr | Tyr | Arg | Thr | Ile | Ser | Ser | Arg | Arg | Leu | Trp | Asp |
|---|---|---|---|---|---|---|---|---|---|---|---|---|---|---|---|
| | | 2115 | | | | 2120 | | | | | 2125 | | | | |

| Ile | Gly | Asn | Gly | Thr | Glu | Cys | Cys | Asn | Phe | Lys | Ile | Tyr | Ser | Phe | Tyr |
|---|---|---|---|---|---|---|---|---|---|---|---|---|---|---|---|
| | | 2130 | | | | 2135 | | | | 2140 | | | | | |

| Lys | Tyr | Glu | Ser | Leu | Lys | Ile | Lys | Tyr | Ser | Leu | Lys | Ser | Leu | His | Asp |
|---|---|---|---|---|---|---|---|---|---|---|---|---|---|---|---|
| 2145 | | | | | 2150 | | | | 2155 | | | | | 2160 | |

| Arg | Trp | Gln | His | Thr | Ala | Val | Asp | Gly | Lys | Leu | Glu | Phe | Tyr | Met | Glu |
|---|---|---|---|---|---|---|---|---|---|---|---|---|---|---|---|
| | | | | 2165 | | | | 2170 | | | | | 2175 | | |

| Gln | Val | Asp | Lys | Phe | Pro | Pro | Ile | Leu | Tyr | Gln | Trp | Phe | Leu | Glu | Asn |
|---|---|---|---|---|---|---|---|---|---|---|---|---|---|---|---|
| | | | 2180 | | | | | 2185 | | | | | 2190 | | |

| Phe | Pro | Asp | Pro | Ile | Asn | Trp | Phe | Asn | Ala | Arg | Asn | Thr | Tyr | Ala | Arg |
|---|---|---|---|---|---|---|---|---|---|---|---|---|---|---|---|
| | | | 2195 | | | | 2200 | | | | | 2205 | | | |

| Ser | Tyr | Ala | Val | Met | Ala | Met | Val | Gly | His | Ile | Leu | Gly | Leu | Gly | Asp |
|---|---|---|---|---|---|---|---|---|---|---|---|---|---|---|---|
| | 2210 | | | | | 2215 | | | | | 2220 | | | | |

| Arg | His | Cys | Glu | Asn | Ile | Leu | Leu | Asp | Ile | Gln | Thr | Gly | Lys | Val | Leu |
|---|---|---|---|---|---|---|---|---|---|---|---|---|---|---|---|
| 2225 | | | | | 2230 | | | | 2235 | | | | | | 2240 |

| His | Val | Asp | Phe | Asp | Cys | Leu | Phe | Glu | Lys | Gly | Lys | Arg | Leu | Pro | Val |
|---|---|---|---|---|---|---|---|---|---|---|---|---|---|---|---|
| | | | | 2245 | | | | 2250 | | | | | 2255 | | |

| Pro | Glu | Ile | Val | Pro | Phe | Arg | Leu | Thr | Pro | Asn | Leu | Leu | Asp | Ala | Leu |
|---|---|---|---|---|---|---|---|---|---|---|---|---|---|---|---|
| | | | 2260 | | | | | 2265 | | | | | 2270 | | |

| Gly | Ile | Ile | Gly | Thr | Glu | Gly | Thr | Phe | Lys | Lys | Ser | Ser | Glu | Val | Thr |
|---|---|---|---|---|---|---|---|---|---|---|---|---|---|---|---|
| | | 2275 | | | | | 2280 | | | | | 2285 | | | |

| Leu | Ala | Leu | Met | Arg | Lys | Asn | Glu | Val | Ala | Leu | Met | Asn | Val | Ile | Glu |
|---|---|---|---|---|---|---|---|---|---|---|---|---|---|---|---|
| | 2290 | | | | | 2295 | | | | | 2300 | | | | |

| Thr | Ile | Met | Tyr | Asp | Arg | Asn | Met | Asp | His | Ser | Ile | Gln | Lys | Ala | Leu |
|---|---|---|---|---|---|---|---|---|---|---|---|---|---|---|---|
| 2305 | | | | | 2310 | | | | 2315 | | | | | | 2320 |

| Lys | Val | Leu | Arg | Asn | Lys | Ile | Arg | Gly | Ile | Asp | Pro | Gln | Asp | Gly | Leu |
|---|---|---|---|---|---|---|---|---|---|---|---|---|---|---|---|
| | | | | 2325 | | | | 2330 | | | | | 2335 | | |

| Val | Leu | Ser | Val | Ala | Gly | Gln | Thr | Glu | Thr | Leu | Ile | Gln | Glu | Ala | Thr |
|---|---|---|---|---|---|---|---|---|---|---|---|---|---|---|---|
| | | | 2340 | | | | | 2345 | | | | | 2350 | | |

| Ser | Glu | Asp | Asn | Leu | Ser | Lys | Met | Tyr | Ile | Gly | Trp | Leu | Pro | Phe | Trp |
|---|---|---|---|---|---|---|---|---|---|---|---|---|---|---|---|
| | | 2355 | | | | | 2360 | | | | | 2365 | | | |

( 2 ) INFORMATION FOR SEQ ID NO:16:

( i ) SEQUENCE CHARACTERISTICS:
        ( A ) LENGTH: 2934 base pairs
        ( B ) TYPE: nucleic acid
        ( C ) STRANDEDNESS: single
        ( D ) TOPOLOGY: linear ( i i ) MOLECULE TYPE: cDNA to mRNA
        ( A ) DESCRIPTION: yeast MEC2 cDNA ( i i i ) HYPOTHETICAL: NO ( i v ) ANTI-SENSE: NO ( v i ) ORIGINAL SOURCE:
    ( A ) ORGANISM: Saccharomyces cerevisiae ( i x ) FEATURE:
    ( A ) NAME/KEY: CDS
    ( B ) LOCATION: 395..2724

( x i ) SEQUENCE DESCRIPTION: SEQ ID NO:16:

```
ATTAATAGCC TGCTTCCTTT TAATTAAGCC GGAAAGTGTT TGTCACAGAT GTCAATGAAA          60

CGTGCATCTA TTAACATATT TATTTTCATT TCGAGGGTGA GGTGGTGTGG ACGCGTTGAT         120

ACGGCAACGG GAGTGACGCG TAAAATTGGC AGAAAAATCA TCACCGTGGG TAGACTTGGA         180

AATGAAAACA TTTATAGAAT AAAGGTACAG GTTGAGAAGA TAAAGGGTAC CAAAGTTACC         240

ATTTTGAAAT CTCTGATCAA GAAAAGGTAA GAAAGCAGAA AAGGACGGTA GAGATTATTG         300

GAAGACAAAC TAATTTTGTA TATGCATTCG ATTTCTTAA GCTTTAAAAG AGAGAATAGT          360

GAGAAAAGAT AGTGTTACAC AACATCAACT AAAA ATG GAA AAT ATT ACA CAA             412
                                      Met Glu Asn Ile Thr Gln
                                        1               5

CCC ACA CAG CAA TCC ACG CAG GCT ACT CAA AGG TTT TTG ATT GAG AAG           460
Pro Thr Gln Gln Ser Thr Gln Ala Thr Gln Arg Phe Leu Ile Glu Lys
             10                  15                  20

TTT TCT CAA GAA CAG ATC GGC GAA AAC ATT GTG TGC AGG GTC ATT TGT           508
Phe Ser Gln Glu Gln Ile Gly Glu Asn Ile Val Cys Arg Val Ile Cys
         25                  30                  35

ACC ACG GGT CAA ATT CCC ATC CGA GAT TTG TCA GCT GAT ATT TCA CAA           556
Thr Thr Gly Gln Ile Pro Ile Arg Asp Leu Ser Ala Asp Ile Ser Gln
     40                  45                  50

GTG CTT AAG GAA AAA CGA TCC ATA AAG AAA GTT TGG ACA TTT GGT AGA           604
Val Leu Lys Glu Lys Arg Ser Ile Lys Lys Val Trp Thr Phe Gly Arg
 55                  60                  65                  70

AAC CCA GCC TGT GAC TAT CAT TTA GGA AAC ATT TCA AGA CTG TCA AAT           652
Asn Pro Ala Cys Asp Tyr His Leu Gly Asn Ile Ser Arg Leu Ser Asn
                 75                  80                  85

AAG CAT TTC CAA ATA CTA CTA GGA GAA GAC GGT AAC CTT TTA TTG AAT           700
Lys His Phe Gln Ile Leu Leu Gly Glu Asp Gly Asn Leu Leu Leu Asn
             90                  95                 100

GAC ATT TCC ACT AAT GGG ACC TGG TTA AAT GGG CAA AAA GTC GAG AAG           748
Asp Ile Ser Thr Asn Gly Thr Trp Leu Asn Gly Gln Lys Val Glu Lys
        105                 110                 115

AAC AGC AAT CAG TTA CTG TCT CAA GGT GAT GAA ATA ACC GTT GGT GTA           796
Asn Ser Asn Gln Leu Leu Ser Gln Gly Asp Glu Ile Thr Val Gly Val
    120                 125                 130

GGC GTG GAA TCA GAT ATT TTA TCT CTG GTC ATT TTC ATA AAC GAC AAA           844
Gly Val Glu Ser Asp Ile Leu Ser Leu Val Ile Phe Ile Asn Asp Lys
135                 140                 145                 150

TTT AAG CAG TGC CTC GAG CAG AAC AAA GTT GAT CGC ATA AGA TCT AAC           892
Phe Lys Gln Cys Leu Glu Gln Asn Lys Val Asp Arg Ile Arg Ser Asn
                155                 160                 165

CTG AAA AAT ACC TCT AAA ATA GCT TCT CCT GGT CTT ACA TCA TCT ACT           940
Leu Lys Asn Thr Ser Lys Ile Ala Ser Pro Gly Leu Thr Ser Ser Thr
            170                 175                 180

GCA TCA TCA ATG GTG GCC AAC AAG ACT GGT ATT TTT AAG GAT TTT TCG           988
Ala Ser Ser Met Val Ala Asn Lys Thr Gly Ile Phe Lys Asp Phe Ser
        185                 190                 195

ATT ATT GAC GAA GTG GTG GGC CAG GGT GCA TTT GCC ACA GTA AAG AAA          1036
Ile Ile Asp Glu Val Val Gly Gln Gly Ala Phe Ala Thr Val Lys Lys
```

```
                    200                       205                          210
GCC  ATT  GAA  AGA  ACT  ACT  GGG  AAA  ACA  TTC  GCG  GTG  AAG  ATT  ATA  AGT    1084
Ala  Ile  Glu  Arg  Thr  Thr  Gly  Lys  Thr  Phe  Ala  Val  Lys  Ile  Ile  Ser
215                      220                      225                      230

AAA  CGC  AAA  GTA  ATA  GGC  AAT  ATG  GAT  GGT  GTG  ACA  AGA  GAG  TTA  GAA    1132
Lys  Arg  Lys  Val  Ile  Gly  Asn  Met  Asp  Gly  Val  Thr  Arg  Glu  Leu  Glu
                    235                      240                      245

GTA  TTG  CAA  AAG  CTC  AAT  CAT  CCA  AGG  ATA  GTA  CGA  TTG  AAA  GGA  TTT    1180
Val  Leu  Gln  Lys  Leu  Asn  His  Pro  Arg  Ile  Val  Arg  Leu  Lys  Gly  Phe
               250                      255                      260

TAT  GAA  GAT  ACT  GAG  AGT  TAT  TAT  ATG  GTG  ATG  GAG  TTC  GTT  TCT  GGT    1228
Tyr  Glu  Asp  Thr  Glu  Ser  Tyr  Tyr  Met  Val  Met  Glu  Phe  Val  Ser  Gly
          265                      270                      275

GGT  GAC  TTA  ATG  GAT  TTT  GTT  GCT  GCT  CAT  GGT  GCG  GTT  GGA  GAA  GAT    1276
Gly  Asp  Leu  Met  Asp  Phe  Val  Ala  Ala  His  Gly  Ala  Val  Gly  Glu  Asp
     280                      285                      290

GCT  GGG  AGG  GAG  ATA  TCC  AGG  CAG  ATA  CTC  ACA  GCA  ATA  AAA  TAC  ATT    1324
Ala  Gly  Arg  Glu  Ile  Ser  Arg  Gln  Ile  Leu  Thr  Ala  Ile  Lys  Tyr  Ile
295                      300                      305                      310

CAC  TCT  ATG  GGC  ATC  AGC  CAT  CGT  GAC  CTA  AAG  CCC  GAT  AAT  ATT  CTT    1372
His  Ser  Met  Gly  Ile  Ser  His  Arg  Asp  Leu  Lys  Pro  Asp  Asn  Ile  Leu
                    315                      320                      325

ATT  GAA  CAA  GAC  GAT  CCT  GTA  TTG  GTA  AAG  ATA  ACC  GAC  TTT  GGT  CTG    1420
Ile  Glu  Gln  Asp  Asp  Pro  Val  Leu  Val  Lys  Ile  Thr  Asp  Phe  Gly  Leu
               330                      335                      340

GCA  AAA  GTA  CAA  GGA  AAT  GGG  TCT  TTT  ATG  AAA  ACC  TTC  TGT  GGC  ACT    1468
Ala  Lys  Val  Gln  Gly  Asn  Gly  Ser  Phe  Met  Lys  Thr  Phe  Cys  Gly  Thr
          345                      350                      355

TTG  GCA  TAT  GTG  GCA  CCT  GAA  GTC  ATC  AGA  GGT  AAA  GAT  ACA  TCC  GTA    1516
Leu  Ala  Tyr  Val  Ala  Pro  Glu  Val  Ile  Arg  Gly  Lys  Asp  Thr  Ser  Val
     360                      365                      370

TCT  CCT  GAT  GAA  TAC  GAA  GAA  AGG  AAT  GAG  TAC  TCT  TCG  TTA  GTG  GAT    1564
Ser  Pro  Asp  Glu  Tyr  Glu  Glu  Arg  Asn  Glu  Tyr  Ser  Ser  Leu  Val  Asp
375                      380                      385                      390

ATG  TGG  TCA  ATG  GGA  TGT  CTT  GTG  TAT  GTT  ATC  CTA  ACG  GGC  CAC  TTA    1612
Met  Trp  Ser  Met  Gly  Cys  Leu  Val  Tyr  Val  Ile  Leu  Thr  Gly  His  Leu
                    395                      400                      405

CCT  TTT  AGT  GGT  AGC  ACA  CAG  GAC  CAA  TTA  TAT  AAA  CAG  ATT  GGA  AGA    1660
Pro  Phe  Ser  Gly  Ser  Thr  Gln  Asp  Gln  Leu  Tyr  Lys  Gln  Ile  Gly  Arg
               410                      415                      420

GGC  TCA  TAT  CAT  GAA  GGG  CCC  CTC  AAA  GAT  TTC  CGG  ATA  TCT  GAA  GAA    1708
Gly  Ser  Tyr  His  Glu  Gly  Pro  Leu  Lys  Asp  Phe  Arg  Ile  Ser  Glu  Glu
          425                      430                      435

GCA  AGA  GAT  TTC  ATA  GAT  TCA  TTG  TTA  CAG  GTG  GAT  CCA  AAT  AAT  AGG    1756
Ala  Arg  Asp  Phe  Ile  Asp  Ser  Leu  Leu  Gln  Val  Asp  Pro  Asn  Asn  Arg
     440                      445                      450

TCG  ACA  GCT  GCA  AAA  GCC  TTG  AAT  CAT  CCC  TGG  ATC  AAG  ATG  AGT  CCA    1804
Ser  Thr  Ala  Ala  Lys  Ala  Leu  Asn  His  Pro  Trp  Ile  Lys  Met  Ser  Pro
455                      460                      465                      470

TTG  GGC  TCA  CAA  TCA  TAT  GGT  GAT  TTT  TCA  CAA  ATA  TCC  TTA  TCA  CAA    1852
Leu  Gly  Ser  Gln  Ser  Tyr  Gly  Asp  Phe  Ser  Gln  Ile  Ser  Leu  Ser  Gln
                    475                      480                      485

TCG  TTG  TCG  CAG  CAG  AAA  TTA  TTA  GAA  AAT  ATG  GAC  GAT  GCT  CAA  TAC    1900
Ser  Leu  Ser  Gln  Gln  Lys  Leu  Leu  Glu  Asn  Met  Asp  Asp  Ala  Gln  Tyr
               490                      495                      500

GAA  TTT  GTC  AAA  GCG  CAA  AGG  AAA  TTA  CAA  ATG  GAG  CAA  CAA  CTT  CAA    1948
Glu  Phe  Val  Lys  Ala  Gln  Arg  Lys  Leu  Gln  Met  Glu  Gln  Gln  Leu  Gln
          505                      510                      515

GAA  CAG  GAT  CAG  GAA  GAC  CAA  GAT  GGA  AAA  ATT  CAA  GGA  TTT  AAA  ATA    1996
Glu  Gln  Asp  Gln  Glu  Asp  Gln  Asp  Gly  Lys  Ile  Gln  Gly  Phe  Lys  Ile
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 520 |     |     |     |     | 525 |     |     |     |     | 530 |     |     |     |      |
| CCC | GCA | CAC | GCC | CCT | ATT | CGA | TAT | ACA | CAG | CCC | AAA | AGC | ATT | GAA | GCA | 2044 |
| Pro | Ala | His | Ala | Pro | Ile | Arg | Tyr | Thr | Gln | Pro | Lys | Ser | Ile | Glu | Ala |      |
| 535 |     |     |     |     | 540 |     |     |     |     | 545 |     |     |     |     | 550 |      |
| GAA | ACT | AGA | GAA | CAA | AAA | CTT | TTA | CAT | TCC | AAT | AAT | ACT | GAG | AAT | GTC | 2092 |
| Glu | Thr | Arg | Glu | Gln | Lys | Leu | Leu | His | Ser | Asn | Asn | Thr | Glu | Asn | Val |      |
|     |     |     |     | 555 |     |     |     |     | 560 |     |     |     |     | 565 |     |      |
| AAG | AGC | TCA | AAG | AAA | AAG | GGT | AAT | GGT | AGG | TTT | TTA | ACT | TTA | AAA | CCA | 2140 |
| Lys | Ser | Ser | Lys | Lys | Lys | Gly | Asn | Gly | Arg | Phe | Leu | Thr | Leu | Lys | Pro |      |
|     |     |     | 570 |     |     |     |     | 575 |     |     |     |     | 580 |     |     |      |
| TTG | CCT | GAC | AGC | ATT | ATT | CAA | GAA | AGC | CTG | GAG | ATT | CAG | CAA | GGT | GTG | 2188 |
| Leu | Pro | Asp | Ser | Ile | Ile | Gln | Glu | Ser | Leu | Glu | Ile | Gln | Gln | Gly | Val |      |
|     |     | 585 |     |     |     |     | 590 |     |     |     |     | 595 |     |     |     |      |
| AAT | CCA | TTT | TTC | ATT | GGT | AGA | TCC | GAG | GAT | TGC | AAT | TGT | AAA | ATT | GAA | 2236 |
| Asn | Pro | Phe | Phe | Ile | Gly | Arg | Ser | Glu | Asp | Cys | Asn | Cys | Lys | Ile | Glu |      |
|     | 600 |     |     |     |     | 605 |     |     |     |     | 610 |     |     |     |     |      |
| GAC | AAT | AGG | TTG | TCT | CGA | GTT | CAT | TGC | TTC | ATT | TTC | AAA | AAG | AGG | CAT | 2284 |
| Asp | Asn | Arg | Leu | Ser | Arg | Val | His | Cys | Phe | Ile | Phe | Lys | Lys | Arg | His |      |
| 615 |     |     |     |     | 620 |     |     |     |     | 625 |     |     |     |     | 630 |      |
| GCT | GTA | GGC | AAA | AGC | ATG | TAT | GAA | TCT | CCG | GCA | CAA | GGT | TTA | GAT | GAT | 2332 |
| Ala | Val | Gly | Lys | Ser | Met | Tyr | Glu | Ser | Pro | Ala | Gln | Gly | Leu | Asp | Asp |      |
|     |     |     |     | 635 |     |     |     |     | 640 |     |     |     |     | 645 |     |      |
| ATT | TGG | TAT | TGC | CAC | ACC | GGA | ACT | AAC | GTG | AGC | TAT | TTA | AAT | AAT | AAC | 2380 |
| Ile | Trp | Tyr | Cys | His | Thr | Gly | Thr | Asn | Val | Ser | Tyr | Leu | Asn | Asn | Asn |      |
|     |     |     | 650 |     |     |     |     | 655 |     |     |     |     | 660 |     |     |      |
| CGC | ATG | ATA | CAG | GGT | ACG | AAA | TTC | CTT | TTA | CAA | GAC | GGA | GAT | GAA | ATC | 2428 |
| Arg | Met | Ile | Gln | Gly | Thr | Lys | Phe | Leu | Leu | Gln | Asp | Gly | Asp | Glu | Ile |      |
|     |     | 665 |     |     |     |     | 670 |     |     |     |     | 675 |     |     |     |      |
| AAG | ATC | ATT | TGG | GAT | AAA | AAC | AAT | AAA | TTT | GTC | ATT | GGC | TTT | AAA | GTG | 2476 |
| Lys | Ile | Ile | Trp | Asp | Lys | Asn | Asn | Lys | Phe | Val | Ile | Gly | Phe | Lys | Val |      |
|     | 680 |     |     |     |     | 685 |     |     |     |     | 690 |     |     |     |     |      |
| GAA | ATT | AAC | GAT | ACT | ACA | GGT | CTG | TTT | AAC | GAG | GGA | TTA | GGT | ATG | TTA | 2524 |
| Glu | Ile | Asn | Asp | Thr | Thr | Gly | Leu | Phe | Asn | Glu | Gly | Leu | Gly | Met | Leu |      |
| 695 |     |     |     |     | 700 |     |     |     |     | 705 |     |     |     |     | 710 |      |
| CAA | GAA | CAA | AGA | GTA | GTA | CTT | AAG | CAA | ACA | GCC | GAA | GAA | AAA | GAT | TTG | 2572 |
| Gln | Glu | Gln | Arg | Val | Val | Leu | Lys | Gln | Thr | Ala | Glu | Glu | Lys | Asp | Leu |      |
|     |     |     |     | 715 |     |     |     |     | 720 |     |     |     |     | 725 |     |      |
| GTG | AAA | AAG | TTA | ACC | CAG | ATG | ATG | GCA | GCT | CAA | CGT | GCA | AAT | CAA | CCC | 2620 |
| Val | Lys | Lys | Leu | Thr | Gln | Met | Met | Ala | Ala | Gln | Arg | Ala | Asn | Gln | Pro |      |
|     |     |     | 730 |     |     |     |     | 735 |     |     |     |     | 740 |     |     |      |
| TCG | GCT | TCT | TCT | TCA | TCA | ATG | TCG | GCT | AAG | AAG | CCG | CCA | GTT | AGC | GAT | 2668 |
| Ser | Ala | Ser | Ser | Ser | Ser | Met | Ser | Ala | Lys | Lys | Pro | Pro | Val | Ser | Asp |      |
|     |     | 745 |     |     |     |     | 750 |     |     |     |     | 755 |     |     |     |      |
| ACA | AAT | AAT | AAC | GGC | AAT | AAT | TCG | GTA | CTA | AAC | GAC | TTG | GTA | GAG | TCA | 2716 |
| Thr | Asn | Asn | Asn | Gly | Asn | Asn | Ser | Val | Leu | Asn | Asp | Leu | Val | Glu | Ser |      |
|     | 760 |     |     |     |     | 765 |     |     |     |     | 770 |     |     |     |     |      |
| CCG | ATT | AA TGCGAATACG GGGAACATTT TGAAGAGAAT ACATTCGGTA AGTTTATCGC | | | | | | | | | | | | | 2774 |
| Pro | Ile |     |     |     |     |     |     |     |     |     |     |     |     |     |     |      |
| 775 |     |     |     |     |     |     |     |     |     |     |     |     |     |     |     |      |

AATCACAAAT TGATCCTAGT AAGAAGGTTA AAAGGGCAAA ATTGGACCAA ACCTCAAAAG  2834

GCCCCGAGAA TTTGCAATTT TCGTAACCAA GGACAAATAC CCATAGAAAA TGCTGCCCCT  2894

TTTTAAGAGA GAAGATGGTA GATACCAATA CTCAGAATTC  2934

( 2 ) INFORMATION FOR SEQ ID NO:17:

( i ) SEQUENCE CHARACTERISTICS:
        ( A ) LENGTH: 776 amino acids
        ( B ) TYPE: amino acid
        ( D ) TOPOLOGY: linear ( i i ) MOLECULE TYPE: protein
  ( A ) DESCRIPTION: yeast MEC2 protein ( x i ) SEQUENCE DESCRIPTION: SEQ ID NO:17:

```
Met Glu Asn Ile Thr Gln Pro Thr Gln Gln Ser Thr Gln Ala Thr Gln
 1               5                  10                  15

Arg Phe Leu Ile Glu Lys Phe Ser Gln Glu Gln Ile Gly Glu Asn Ile
                20                  25                  30

Val Cys Arg Val Ile Cys Thr Thr Gly Gln Ile Pro Ile Arg Asp Leu
            35                  40                  45

Ser Ala Asp Ile Ser Gln Val Leu Lys Glu Lys Arg Ser Ile Lys Lys
        50                  55                  60

Val Trp Thr Phe Gly Arg Asn Pro Ala Cys Asp Tyr His Leu Gly Asn
 65                  70                  75                  80

Ile Ser Arg Leu Ser Asn Lys His Phe Gln Ile Leu Leu Gly Glu Asp
                85                  90                  95

Gly Asn Leu Leu Leu Asn Asp Ile Ser Thr Asn Gly Thr Trp Leu Asn
               100                 105                 110

Gly Gln Lys Val Glu Lys Asn Ser Asn Gln Leu Leu Ser Gln Gly Asp
           115                 120                 125

Glu Ile Thr Val Gly Val Gly Val Glu Ser Asp Ile Leu Ser Leu Val
       130                 135                 140

Ile Phe Ile Asn Asp Lys Phe Lys Gln Cys Leu Glu Gln Asn Lys Val
145                 150                 155                 160

Asp Arg Ile Arg Ser Asn Leu Lys Asn Thr Ser Lys Ile Ala Ser Pro
               165                 170                 175

Gly Leu Thr Ser Ser Thr Ala Ser Ser Met Val Ala Asn Lys Thr Gly
           180                 185                 190

Ile Phe Lys Asp Phe Ser Ile Ile Asp Glu Val Val Gly Gln Gly Ala
       195                 200                 205

Phe Ala Thr Val Lys Lys Ala Ile Glu Arg Thr Thr Gly Lys Thr Phe
   210                 215                 220

Ala Val Lys Ile Ile Ser Lys Arg Lys Val Ile Gly Asn Met Asp Gly
225                 230                 235                 240

Val Thr Arg Glu Leu Glu Val Leu Gln Lys Leu Asn His Pro Arg Ile
               245                 250                 255

Val Arg Leu Lys Gly Phe Tyr Glu Asp Thr Glu Ser Tyr Tyr Met Val
           260                 265                 270

Met Glu Phe Val Ser Gly Gly Asp Leu Met Asp Phe Val Ala Ala His
       275                 280                 285

Gly Ala Val Gly Glu Asp Ala Gly Arg Glu Ile Ser Arg Gln Ile Leu
   290                 295                 300

Thr Ala Ile Lys Tyr Ile His Ser Met Gly Ile Ser His Arg Asp Leu
305                 310                 315                 320

Lys Pro Asp Asn Ile Leu Ile Glu Gln Asp Asp Pro Val Leu Val Lys
               325                 330                 335

Ile Thr Asp Phe Gly Leu Ala Lys Val Gln Gly Asn Gly Ser Phe Met
           340                 345                 350

Lys Thr Phe Cys Gly Thr Leu Ala Tyr Val Ala Pro Glu Val Ile Arg
       355                 360                 365

Gly Lys Asp Thr Ser Val Ser Pro Asp Glu Tyr Glu Glu Arg Asn Glu
   370                 375                 380

Tyr Ser Ser Leu Val Asp Met Trp Ser Met Gly Cys Leu Val Tyr Val
385                 390                 395                 400
```

```
Ile Leu Thr Gly His Leu Pro Phe Ser Gly Ser Thr Gln Asp Gln Leu
            405                 410                 415
Tyr Lys Gln Ile Gly Arg Gly Ser Tyr His Glu Gly Pro Leu Lys Asp
            420                 425                 430
Phe Arg Ile Ser Glu Glu Ala Arg Asp Phe Ile Asp Ser Leu Leu Gln
        435                 440                 445
Val Asp Pro Asn Asn Arg Ser Thr Ala Ala Lys Ala Leu Asn His Pro
    450                 455                 460
Trp Ile Lys Met Ser Pro Leu Gly Ser Gln Ser Tyr Gly Asp Phe Ser
465                 470                 475                 480
Gln Ile Ser Leu Ser Gln Ser Leu Ser Gln Gln Lys Leu Leu Glu Asn
                485                 490                 495
Met Asp Asp Ala Gln Tyr Glu Phe Val Lys Ala Gln Arg Lys Leu Gln
            500                 505                 510
Met Glu Gln Gln Leu Gln Glu Gln Asp Gln Glu Asp Gln Asp Gly Lys
        515                 520                 525
Ile Gln Gly Phe Lys Ile Pro Ala His Ala Pro Ile Arg Tyr Thr Gln
    530                 535                 540
Pro Lys Ser Ile Glu Ala Glu Thr Arg Glu Gln Lys Leu Leu His Ser
545                 550                 555                 560
Asn Asn Thr Glu Asn Val Lys Ser Ser Lys Lys Lys Gly Asn Gly Arg
                565                 570                 575
Phe Leu Thr Leu Lys Pro Leu Pro Asp Ser Ile Ile Gln Glu Ser Leu
            580                 585                 590
Glu Ile Gln Gln Gly Val Asn Pro Phe Phe Ile Gly Arg Ser Glu Asp
        595                 600                 605
Cys Asn Cys Lys Ile Glu Asp Asn Arg Leu Ser Arg Val His Cys Phe
    610                 615                 620
Ile Phe Lys Lys Arg His Ala Val Gly Lys Ser Met Tyr Glu Ser Pro
625                 630                 635                 640
Ala Gln Gly Leu Asp Asp Ile Trp Tyr Cys His Thr Gly Thr Asn Val
            645                 650                 655
Ser Tyr Leu Asn Asn Asn Arg Met Ile Gln Gly Thr Lys Phe Leu Leu
        660                 665                 670
Gln Asp Gly Asp Glu Ile Lys Ile Ile Trp Asp Lys Asn Asn Lys Phe
    675                 680                 685
Val Ile Gly Phe Lys Val Glu Ile Asn Asp Thr Thr Gly Leu Phe Asn
    690                 695                 700
Glu Gly Leu Gly Met Leu Gln Glu Gln Arg Val Val Leu Lys Gln Thr
705                 710                 715                 720
Ala Glu Glu Lys Asp Leu Val Lys Lys Leu Thr Gln Met Met Ala Ala
            725                 730                 735
Gln Arg Ala Asn Gln Pro Ser Ala Ser Ser Ser Ser Met Ser Ala Lys
        740                 745                 750
Lys Pro Pro Val Ser Asp Thr Asn Asn Gly Asn Asn Ser Val Leu
    755                 760                 765
Asn Asp Leu Val Glu Ser Pro Ile
    770                 775
```

( 2 ) INFORMATION FOR SEQ ID NO:18:

( i ) SEQUENCE CHARACTERISTICS:
        ( A ) LENGTH: 3551 base pairs
        ( B ) TYPE: nucleic acid
        ( C ) STRANDEDNESS: single
        ( D ) TOPOLOGY: linear ( i i ) MOLECULE TYPE: cDNA to mRNA
   ( A ) DESCRIPTION: yeast MEC3 cDNA ( v i ) ORIGINAL SOURCE:
   ( A ) ORGANISM: Saccharomyces cerevisiae ( i x ) FEATURE:
   ( A ) NAME/KEY: CDS
   ( B ) LOCATION: 1467..3227

( x i ) SEQUENCE DESCRIPTION: SEQ ID NO:18:

```
AACTTCTTCA AATGCAGCGA TAGCTTGGAA CACACCTTCC AAGTCTTTGC AAGGGATGAC      60
CACTTCATGT GTCGACGAAC TTTCCTGTTC AGCCTTTTCC ACCATAACGG ATATGTCATT     120
AAATTCAGTA TCACCGCTAG TATCAGCTGT GTAAATGTTT CCCCGCGTAT CTGCGATCGA     180
GCTATCCTCA ATTCTTAATA AATCTTCATC GTAGCGGATA TTCTCTTCCA TCTCTCGATC     240
TCTAGTATTG GTATATAGTG AAGACATCGG TTTATCCGCT TCGATAATCG GAAGAGATCC     300
TTCCTCCTGC CGGCCGTCTG TGTCGATGTG CTGGTTTTGG GAAGGATTGT CAGTGAGCCC     360
TTCTTGGCGT TGTATCACAG AATCTAAGGG TCCATTCCAA CATATTTCCA AATGCCAATC     420
TAATTCATTC ACAATTATCT TGAGTTCTAC ATCATCACCT TCATTCCAT GCTCCTTTTT     480
TTTGACTCCC ATTAAATGAA TGTGGTTGAC ATTGCTGTAC CGTTCAACAC GTCTAATGAA     540
CCCGTGGAAG CGGAGCCAAA CTCACCCGAT ATTGGTGGTA GCTTGTACAT CATCAGTTGA     600
ATATAGTTAA TCATTGGCTC TTGTATTCGC GTATGCTTGT GCTCGGAATA ATAGTTTGAC     660
AGGTACTTTG AACGAATGAT ATAACCTTAT TGCTTGCTAG TAGATTTCCT GTGCCTACTG     720
TGGTTGGTAA ACCATTGTGC TCATCCACTC CCCCATCCAT AACTATAGCG TCATTTGGGC     780
CGCTGGTATG TACAATTTCT TCGAATGTTA TACCTAAAGC ACAAATGGGG TTCGGTTTTG     840
AGGTTGTATC TACGCCTCCT GCTGTTCCTC CTGAAAGTGT TCCGTTATTT GTATTCCATT     900
CTGGCATTGA CTGTAGTTTT ATAATCATAT TAGAGAAGAT CCTTGGTTCA TTACTCGATC     960
ATATCTTTTA AACACACTCA ATAAACAATC ACAATTGACA CTCCATTGTT ATTGTATTAA    1020
GCTCGCGAGC TGATATAACT GTTATATAAT CTGAATACAT CATGAGGAAT GGTACACCAA    1080
AGCTGACCAG TATCCCCTCG TAATATTGTA CCGTTGTTAC TGCTGTTGAG TGATGATTTT    1140
GGAGTGGATA TTATTGTCAA TCTTTCACTA TTAAATCTTA AGATAGCCGT CTTTCGTAGC    1200
GAACGAACTG TATTGATAGT AGTTCTTAGC AATTTATAAT CATCAGGTGC TTCACAACCA    1260
TTTACTATCA ATTTTAATTT CATTTAACTG AATTAAGACA CACCTTTTGT CTTCTTTTTT    1320
CTCTCATCAT CTCCGTATGT TTATCTTGCT ATTTGATGT AAATAAAAAA GTTGAATAAT    1380
AGACGAGGGC AAGTATAACT CGCCTATATT GTAGCCGCAA CCATTGAAAA AAAGCCATGA    1440
ATATGAGAAA ATAGTTGCAC ATAAAA ATG CTG AAA TTT AGA ATT AGG CCA AAT     1493
                              Met Leu Lys Phe Arg Ile Arg Pro Asn
                                1               5

AGA CAT ATA CGG TGT TAT AAA CGA CAC GCA TAT TTC TTA CGA TAT AAC      1541
Arg His Ile Arg Cys Tyr Lys Arg His Ala Tyr Phe Leu Arg Tyr Asn
 10              15                  20                  25

CAT ACG ACT ACC CCT GCA CAG AAG TTA CAA GCA CAG ATC GAG CAA ATA      1589
His Thr Thr Thr Pro Ala Gln Lys Leu Gln Ala Gln Ile Glu Gln Ile
                 30                  35                  40

CCT CTC GAA AAT TAC AGA AAT TTT TCT ATA GTT GCC CAT GTT GAC CAT      1637
Pro Leu Glu Asn Tyr Arg Asn Phe Ser Ile Val Ala His Val Asp His
             45                  50                  55

GGG AAG TCA ACC TTA AGT GAC AGA CTG CTG GAA ATA ACG CAT GTC ATC      1685
Gly Lys Ser Thr Leu Ser Asp Arg Leu Leu Glu Ile Thr His Val Ile
 60              65                  70
```

| | | | | | | | | | | | | | | | | |
|---|---|---|---|---|---|---|---|---|---|---|---|---|---|---|---|---|
| GAT | CCC | AAT | GCG | AGA | AAT | AAA | CAA | GTT | TTG | GAT | AAA | TTG | GAA | GTC | GAA | 1733 |
| Asp | Pro | Asn | Ala | Arg | Asn | Lys | Gln | Val | Leu | Asp | Lys | Leu | Glu | Val | Glu | |
| | 75 | | | | | 80 | | | | | 85 | | | | | |
| AGA | GAA | AGA | GGT | ATT | ACT | ATA | AAG | GCG | CAA | ACA | TGT | TCG | ATG | TTT | TAT | 1781 |
| Arg | Glu | Arg | Gly | Ile | Thr | Ile | Lys | Ala | Gln | Thr | Cys | Ser | Met | Phe | Tyr | |
| 90 | | | | | 95 | | | | | 100 | | | | | 105 | |
| AAA | GAT | AAG | AGG | ACC | GGA | AAA | AAC | TAT | CTT | TTA | CAT | TTA | ATT | GAC | ACG | 1829 |
| Lys | Asp | Lys | Arg | Thr | Gly | Lys | Asn | Tyr | Leu | His | Leu | Ile | Asp | Thr | |
| | | | | 110 | | | | | 115 | | | | | 120 | | |
| CCA | GGA | CAT | GTG | GAC | TTC | AGA | GGT | GAA | GTT | TCA | CGG | TCA | TAT | GCG | TCT | 1877 |
| Pro | Gly | His | Val | Asp | Phe | Arg | Gly | Glu | Val | Ser | Arg | Ser | Tyr | Ala | Ser | |
| | | | 125 | | | | | 130 | | | | | 135 | | | |
| TGT | GGG | GGA | GCA | ATT | CTT | TTG | GTT | GAT | GCA | TCA | CAA | GGC | ATA | CAA | GCA | 1925 |
| Cys | Gly | Gly | Ala | Ile | Leu | Leu | Val | Asp | Ala | Ser | Gln | Gly | Ile | Gln | Ala | |
| | | 140 | | | | | 145 | | | | | 150 | | | | |
| CAG | ACG | GTT | GCT | AAT | TTT | TAT | TTA | GCC | TTC | AGT | TTA | GGA | TTG | AAA | TTG | 1973 |
| Gln | Thr | Val | Ala | Asn | Phe | Tyr | Leu | Ala | Phe | Ser | Leu | Gly | Leu | Lys | Leu | |
| | 155 | | | | | 160 | | | | | 165 | | | | | |
| ATT | CCA | GTA | ATA | AAC | AAA | ATT | GAT | CTC | AAT | TTT | ACA | GAT | GTT | AAA | CAG | 2021 |
| Ile | Pro | Val | Ile | Asn | Lys | Ile | Asp | Leu | Asn | Phe | Thr | Asp | Val | Lys | Gln | |
| 170 | | | | | 175 | | | | | 180 | | | | | 185 | |
| GTA | AAG | GAT | CAG | ATA | GTG | AAT | AAC | TTT | GAG | CTC | CCC | GAG | GAA | GAT | ATA | 2069 |
| Val | Lys | Asp | Gln | Ile | Val | Asn | Asn | Phe | Glu | Leu | Pro | Glu | Glu | Asp | Ile | |
| | | | | 190 | | | | | 195 | | | | | 200 | | |
| ATC | GGA | GTA | AGT | CGT | AAA | ACA | GCA | TTA | AAT | GTA | GAG | GAA | CTG | TTA | CTA | 2117 |
| Ile | Gly | Val | Ser | Arg | Lys | Thr | Ala | Leu | Asn | Val | Glu | Glu | Leu | Leu | Leu | |
| | | | 205 | | | | | 210 | | | | | 215 | | | |
| CCG | GCT | ATA | ATT | GAT | CGT | ATA | CCA | CCA | CCA | ACT | GGG | AGG | CCT | GAT | AAA | 2165 |
| Pro | Ala | Ile | Ile | Asp | Arg | Ile | Pro | Pro | Pro | Thr | Gly | Arg | Pro | Asp | Lys | |
| | | | 220 | | | | | 225 | | | | | 230 | | | |
| CCC | TTC | AGA | GCA | TTA | TTA | GTG | GAT | TCT | TGG | TAC | GAC | GCA | TAC | TTA | GGA | 2213 |
| Pro | Phe | Arg | Ala | Leu | Leu | Val | Asp | Ser | Trp | Tyr | Asp | Ala | Tyr | Leu | Gly | |
| | 235 | | | | | 240 | | | | | 245 | | | | | |
| GCG | GTT | CTT | CTA | GTG | AAT | ATT | GTT | GAT | GGT | TTT | GTA | CGT | AAA | AAT | GAC | 2261 |
| Ala | Val | Leu | Leu | Val | Asn | Ile | Val | Asp | Gly | Phe | Val | Arg | Lys | Asn | Asp | |
| 250 | | | | | 255 | | | | | 260 | | | | | 265 | |
| AAA | GTT | ATT | TGT | GCT | CAG | ACA | AAA | GAA | AAA | TAC | GAA | GTC | AAA | GAT | ATT | 2309 |
| Lys | Val | Ile | Cys | Ala | Gln | Thr | Lys | Glu | Lys | Tyr | Glu | Val | Lys | Asp | Ile | |
| | | | 270 | | | | | 275 | | | | | 280 | | | |
| GGA | ATC | ATG | TAT | CCT | GAC | AGA | ACT | TCT | ACA | GGT | ACG | CTA | AAG | ACA | GGA | 2357 |
| Gly | Ile | Met | Tyr | Pro | Asp | Arg | Thr | Ser | Thr | Gly | Thr | Leu | Lys | Thr | Gly | |
| | | | 285 | | | | | 290 | | | | | 295 | | | |
| CAA | GTT | GGC | TAT | CTA | GTG | CTG | GGA | ATG | AAG | GAT | TCT | AAA | GAA | GCA | AAA | 2405 |
| Gln | Val | Gly | Tyr | Leu | Val | Leu | Gly | Met | Lys | Asp | Ser | Lys | Glu | Ala | Lys | |
| | | 300 | | | | | 305 | | | | | 310 | | | | |
| ATT | GGA | GAT | ACT | ATA | ATG | CAT | TTA | AGT | AAA | GTA | AAT | GAA | ACG | GAA | GTA | 2453 |
| Ile | Gly | Asp | Thr | Ile | Met | His | Leu | Ser | Lys | Val | Asn | Glu | Thr | Glu | Val | |
| | 315 | | | | | 320 | | | | | 325 | | | | | |
| CTT | CCC | GGA | TTT | GAA | GAA | CAA | AAA | CCC | ATG | GTA | TTT | GTG | GGT | GCT | TTC | 2501 |
| Leu | Pro | Gly | Phe | Glu | Glu | Gln | Lys | Pro | Met | Val | Phe | Val | Gly | Ala | Phe | |
| 330 | | | | | 335 | | | | | 340 | | | | | 345 | |
| CCG | GCT | GAT | GGG | ATT | GAA | TTC | AAA | CCC | ATG | GAT | GAT | GAT | ATG | AGT | AGA | 2549 |
| Pro | Ala | Asp | Gly | Ile | Glu | Phe | Lys | Pro | Met | Asp | Asp | Asp | Met | Ser | Arg | |
| | | | 350 | | | | | 355 | | | | | 360 | | | |
| CTT | GTT | CTC | AAC | GAT | AGG | TCA | GTT | ACT | TTG | GAA | CGT | CAG | ACC | TCC | AAT | 2597 |
| Leu | Val | Leu | Asn | Asp | Arg | Ser | Val | Thr | Leu | Glu | Arg | Gln | Thr | Ser | Asn | |
| | | | 365 | | | | | 370 | | | | | 375 | | | |
| GCT | TTG | GGT | CAA | GGT | TGG | AGA | TTG | GGC | TTT | TTA | GGA | TCT | TTA | CAT | GCA | 2645 |
| Ala | Leu | Gly | Gln | Gly | Trp | Arg | Leu | Gly | Phe | Leu | Gly | Ser | Leu | His | Ala | |
| | | 380 | | | | | 385 | | | | | 390 | | | | |

```
TCT GTT TTT CGT GAA CGA CTA GAA AAA GAG TAT GGT TCG AAA TTG ATC         2693
Ser Val Phe Arg Glu Arg Leu Glu Lys Glu Tyr Gly Ser Lys Leu Ile
    395             400             405

ATT ACT CAA CCC ACA GTT CCT TAT TTG GTG GAG TTT ACC GAT GGT AAG         2741
Ile Thr Gln Pro Thr Val Pro Tyr Leu Val Glu Phe Thr Asp Gly Lys
410             415             420                         425

AAA AAA CTT ATA ACA AAT CCG GAT GAG TTT CCA GAC GGA GCA ACA AAG         2789
Lys Lys Leu Ile Thr Asn Pro Asp Glu Phe Pro Asp Gly Ala Thr Lys
                430             435                         440

AGG GTG AAC GTT GCT GCT TTC CAT GAA CCG TTT ATA GAG GCA GTT ATG         2837
Arg Val Asn Val Ala Ala Phe His Glu Pro Phe Ile Glu Ala Val Met
            445             450             455

ACA TTG CCC CAG GAA TAT TTA GGT AGT GTC ATA CGC TTA TGC GAT AGT         2885
Thr Leu Pro Gln Glu Tyr Leu Gly Ser Val Ile Arg Leu Cys Asp Ser
        460             465             470

AAT AGA GGA GAA CAA ATT GAT ATA ACA TAC CTA AAC ACC AAT GGA CAA         2933
Asn Arg Gly Glu Gln Ile Asp Ile Thr Tyr Leu Asn Thr Asn Gly Gln
    475             480             485

GTG ATG TTA AAA TAT TAC CTT CCG CTA TCG CAT CTA GTC GAT GAC TTT         2981
Val Met Leu Lys Tyr Tyr Leu Pro Leu Ser His Leu Val Asp Asp Phe
490             495             500                         505

TTT GGT AAA TTA AAA TCG GTG TCC AGA GGA TTT GCC TCT TTA GAT TAT         3029
Phe Gly Lys Leu Lys Ser Val Ser Arg Gly Phe Ala Ser Leu Asp Tyr
                510             515                         520

GAG GAT GCT GGC TAT AGA ATT TCT GAT GTT GTA AAA CTG CAA CTC TTG         3077
Glu Asp Ala Gly Tyr Arg Ile Ser Asp Val Val Lys Leu Gln Leu Leu
            525             530             535

GTT AAT GGA AAT GCG ATT GAT GCC TTG TCA AGA GTA CTT CAT AAA TCG         3125
Val Asn Gly Asn Ala Ile Asp Ala Leu Ser Arg Val Leu His Lys Ser
        540             545             550

GAA GTA GAG AGA GTG CGT AGA GAA TGG GTA AAG AAG TTT AAA GAG TAT         3173
Glu Val Glu Arg Val Arg Arg Glu Trp Val Lys Lys Phe Lys Glu Tyr
    555             560             565

GTT AAA TCA CAA TTA TAT GAG GTC TTA TAC AGG CCC GAG CTA ATA ACA         3221
Val Lys Ser Gln Leu Tyr Glu Val Leu Tyr Arg Pro Glu Leu Ile Thr
570             575             580             585

AGA TAATCGCTAG AGAAACAATT AAGGCAAGAA GAAAGATGT TCTCCAAAAG              3274
Arg

CTGCATGCTT CTGATGTCTC ACGAAGGAAA AAACTTTTGG CGAAACAGAA AGAGGGAAAA      3334

AGCATATGAA AACTGTAGGT AATATTCAAA TCAACCAAGA GGCATATCAG GCTTTTTTGC      3394

GCCGTTAGCA TTGCATATTA TTGTTATTAC CATTTAAAA TTATACCAAG CTGTACATAG       3454

TTAAGTACTT TTCATTTGTA AATAAAGAG AAAAATAGAT TAATAAATAT TATAATGACA       3514

TAACATTATG CTTTAAGTAT TTCTCAAGTG TAACTAC                              3551
```

( 2 ) INFORMATION FOR SEQ ID NO:19:

( i ) SEQUENCE CHARACTERISTICS:
        ( A ) LENGTH: 586 amino acids
        ( B ) TYPE: amino acid
        ( D ) TOPOLOGY: linear ( i i ) MOLECULE TYPE: protein
        ( A ) DESCRIPTION: yeast MEC3 protein ( x i ) SEQUENCE DESCRIPTION: SEQ ID NO:19:

```
Met Leu Lys Phe Arg Ile Arg Pro Asn Arg His Ile Arg Cys Tyr Lys
1               5               10                          15

Arg His Ala Tyr Phe Leu Arg Tyr Asn His Thr Thr Thr Pro Ala Gln
            20              25              30
```

```
Lys Leu Gln Ala Gln Ile Glu Gln Ile Pro Leu Glu Asn Tyr Arg Asn
         35                  40                  45

Phe Ser Ile Val Ala His Val Asp His Gly Lys Ser Thr Leu Ser Asp
     50                  55                  60

Arg Leu Leu Glu Ile Thr His Val Ile Asp Pro Asn Ala Arg Asn Lys
 65              70                  75                      80

Gln Val Leu Asp Lys Leu Glu Val Glu Arg Glu Arg Gly Ile Thr Ile
             85                  90                  95

Lys Ala Gln Thr Cys Ser Met Phe Tyr Lys Asp Lys Arg Thr Gly Lys
            100                 105                 110

Asn Tyr Leu Leu His Leu Ile Asp Thr Pro Gly His Val Asp Phe Arg
        115                 120                 125

Gly Glu Val Ser Arg Ser Tyr Ala Ser Cys Gly Gly Ala Ile Leu Leu
    130                 135                 140

Val Asp Ala Ser Gln Gly Ile Gln Ala Gln Thr Val Ala Asn Phe Tyr
145                 150                 155                 160

Leu Ala Phe Ser Leu Gly Leu Lys Leu Ile Pro Val Ile Asn Lys Ile
                165                 170                 175

Asp Leu Asn Phe Thr Asp Val Lys Gln Val Lys Asp Gln Ile Val Asn
            180                 185                 190

Asn Phe Glu Leu Pro Glu Glu Asp Ile Ile Gly Val Ser Arg Lys Thr
        195                 200                 205

Ala Leu Asn Val Glu Glu Leu Leu Pro Ala Ile Ile Asp Arg Ile
    210                 215                 220

Pro Pro Pro Thr Gly Arg Pro Asp Lys Pro Phe Arg Ala Leu Leu Val
225                 230                 235                 240

Asp Ser Trp Tyr Asp Ala Tyr Leu Gly Ala Val Leu Leu Val Asn Ile
                245                 250                 255

Val Asp Gly Phe Val Arg Lys Asn Asp Lys Val Ile Cys Ala Gln Thr
            260                 265                 270

Lys Glu Lys Tyr Glu Val Lys Asp Ile Gly Ile Met Tyr Pro Asp Arg
        275                 280                 285

Thr Ser Thr Gly Thr Leu Lys Thr Gly Gln Val Gly Tyr Leu Val Leu
    290                 295                 300

Gly Met Lys Asp Ser Lys Glu Ala Lys Ile Gly Asp Thr Ile Met His
305                 310                 315                 320

Leu Ser Lys Val Asn Glu Thr Glu Val Leu Pro Gly Phe Glu Glu Gln
                325                 330                 335

Lys Pro Met Val Phe Val Gly Ala Phe Pro Ala Asp Gly Ile Glu Phe
            340                 345                 350

Lys Pro Met Asp Asp Met Ser Arg Leu Val Leu Asn Asp Arg Ser
        355                 360                 365

Val Thr Leu Glu Arg Gln Thr Ser Asn Ala Leu Gly Gln Gly Trp Arg
    370                 375                 380

Leu Gly Phe Leu Gly Ser Leu His Ala Ser Val Phe Arg Glu Arg Leu
385                 390                 395                 400

Glu Lys Glu Tyr Gly Ser Lys Leu Ile Ile Thr Gln Pro Thr Val Pro
                405                 410                 415

Tyr Leu Val Glu Phe Thr Asp Gly Lys Lys Lys Leu Ile Thr Asn Pro
            420                 425                 430

Asp Glu Phe Pro Asp Gly Ala Thr Lys Arg Val Asn Val Ala Ala Phe
        435                 440                 445

His Glu Pro Phe Ile Glu Ala Val Met Thr Leu Pro Gln Glu Tyr Leu
```

-continued

|   | 450 |   |   |   |   | 455 |   |   |   |   | 460 |   |   |   |   |
|---|---|---|---|---|---|---|---|---|---|---|---|---|---|---|---|
| Gly 465 | Ser | Val | Ile | Arg | Leu 470 | Cys | Asp | Ser | Asn | Arg 475 | Gly | Glu | Gln | Ile | Asp 480 |
| Ile | Thr | Tyr | Leu | Asn 485 | Thr | Asn | Gly | Gln | Val 490 | Met | Leu | Lys | Tyr | Tyr 495 | Leu |
| Pro | Leu | Ser | His 500 | Leu | Val | Asp | Asp | Phe 505 | Phe | Gly | Lys | Leu | Lys 510 | Ser | Val |
| Ser | Arg | Gly 515 | Phe | Ala | Ser | Leu | Asp 520 | Tyr | Glu | Asp | Ala | Gly 525 | Tyr | Arg | Ile |
| Ser | Asp 530 | Val | Val | Lys | Leu | Gln 535 | Leu | Leu | Val | Asn | Gly 540 | Asn | Ala | Ile | Asp |
| Ala 545 | Leu | Ser | Arg | Val | Leu 550 | His | Lys | Ser | Glu | Val 555 | Glu | Arg | Val | Arg | Arg 560 |
| Glu | Trp | Val | Lys | Lys 565 | Phe | Lys | Glu | Tyr | Val 570 | Lys | Ser | Gln | Leu | Tyr 575 | Glu |
| Val | Leu | Tyr | Arg 580 | Pro | Glu | Leu | Ile | Thr 585 | Arg |   |   |   |   |   |   |